(12) United States Patent
Janjic et al.

(10) Patent No.: US 6,177,557 B1
(45) Date of Patent: *Jan. 23, 2001

(54) HIGH AFFINITY LIGANDS OF BASIC FIBROBLAST GROWTH FACTOR AND THROMBIN

(75) Inventors: Nebojsa Janjic; Larry Gold; Diane Tasset, all of Boulder, CO (US)

(73) Assignee: NeXstar Pharmaceuticals, Inc., Boulder, CO (US)

( * ) Notice: Under 35 U.S.C. 154(b), the term of this patent shall be extended for 0 days.

This patent is subject to a terminal disclaimer.

(21) Appl. No.: 08/687,421

(22) Filed: Aug. 5, 1996

Related U.S. Application Data

(63) Continuation-in-part of application No. 08/195,005, filed on Feb. 10, 1994, now Pat. No. 5,459,015, and a continuation-in-part of application No. 08/219,012, filed on Mar. 28, 1994, now Pat. No. 5,543,293, which is a continuation-in-part of application No. 07/973,333, filed on Nov. 6, 1992, now Pat. No. 5,476,766, which is a continuation-in-part of application No. 07/714,131, filed on Jun. 10, 1991, now Pat. No. 5,475,096, and a continuation-in-part of application No. 07/536,428, filed on Jun. 11, 1990, now abandoned, said application No. 07/214,131, is a continuation-in-part of application No. 07/536,428, said application No. 08/195,005, is a continuation-in-part of application No. 08/061,691, filed on Apr. 22, 1993, now abandoned, and a continuation-in-part of application No. 07/714,131.

(51) Int. Cl.[7] ............................ C07H 21/02; C07H 21/04; C12Q 1/68
(52) U.S. Cl. ......................... 536/24.31; 435/6; 536/23.1; 536/25.4; 935/77; 935/78
(58) Field of Search ..................... 435/6, 91.2; 536/23.1, 536/24.31, 25.4; 514/44; 935/72, 78

(56) References Cited

U.S. PATENT DOCUMENTS

| | | | |
|---|---|---|---|
| 4,833,092 | 5/1989 | Gevsen | 435/6 |
| 5,118,672 | 6/1992 | Schinazi | 435/6 |
| 5,133,866 | 7/1992 | Kauvar | 435/6 |
| 5,270,163 | 12/1993 | Gold et al. | 435/6 |
| 5,459,015 | 10/1995 | Janjic et al. | 435/6 |
| 5,472,841 | 12/1995 | Jayasena et al. | 435/6 |
| 5,475,096 | 12/1995 | Gold et al. | 435/6 |
| 5,476,766 | 12/1995 | Gold et al. | 435/6 |
| 5,496,938 | 3/1996 | Gold et al. | 435/6 |
| 5,503,978 | 4/1996 | Schneider et al. | 435/6 |
| 5,527,894 | 6/1996 | Gold et al. | 435/6 |
| 5,543,293 | 8/1996 | Gold et al. | 435/6 |
| 5,567,588 | 10/1996 | Gold et al. | 435/6 |
| 5,580,737 | 12/1996 | Polisky et al. | 435/6 |
| 5,587,468 | 12/1996 | Allen et al. | 435/6 |
| 5,595,877 | 1/1997 | Gold et al. | 435/6 |

FOREIGN PATENT DOCUMENTS

| | | |
|---|---|---|
| 2 183 661 | 6/1985 | (GB) . |
| WO89/06694 | 7/1989 | (WO) . |
| WO 92/03568 | 3/1992 | (WO) . |
| WO92/14843 | 9/1992 | (WO) . |

OTHER PUBLICATIONS

Joyce (1989) Gene 82:83.
Joyce & Inoue (1989) Nucleic Acids Research 17:711.
Ellington & Szostak (1990) Abstract of papers presented at the 1990 meeting on RNA Processing, Cold Spring Harbor Laboratory, Cold Spring Harbor, NY, p. 84.
Kinzler & Vogelstein (1989) Nucleic Acids Research 17:3645.
Kramer et al. (1974) J. Mol. Biol. 89:719.
Levisohn & Spiegelman (1969) PNAS USA 63:805.
Levisohn & Spiegelman (1968) PNAS USA 60:866.
Oliphant et al. (1989) Mol. Cell. Biol. 9:2944.
Oliphant & Struhl (1988) Nucleic Acids Research 16:7673.
Oliphant & Struhl (1987) Methods in Enzymology 155:568.
Oliphant et al. (1986) Gene 44:177.
Robertson & Joyce (1990) Nature 344:467.
Thiesen & Bach (1990) Nucleic Acids Research 18:3203.
Carey et al. (1983) Biochemistry 22:2601.
Uhlenbeck et al. (1983) J. Biomol. Structure Dynamics 1:539.
Witherell and Uhlenbeck (1989) Biochemistry 28:71.
Joyce (1988) in *RNA: Catalysis, Splicing, Evolution*, Belfort and Shub, eds., Elsevier Amsterdam pp. 83–87.
Koch et al. (1992) Science 258:1798.
Tuerk and Gold (1990) Science 249:505.
Romaniuk et al. (1987) Biochemistry 26:1563.
Kramer et al. (1974) J. Mol. Biol. 89:719.
Bass and Cech (1984) Nature 308:820.
Yarus (1988) Science 240:1751.
Rich et al. (1984) Ann. Rev. Biochem. 53:791.
Schimmel (1989) Cell 58:9.
Tuerk et al. (1988) Proc. Natl. Acad. Sci. USA 85:1364.
Mills et al. (1967) Proc. Natl. Acad. Sci. USA 58:217.
Baird and Bohlen (1991) in *Peptide Growth Factors and Their Receptors* (Sporn, M.B. and Roberts, A.B., eds.) pp. 369–418, Springer NY: Fibroblast Growth Factors.
Jaye et al. (1986) Science 233:541.
Abraham et al. (1986) Science 233:545.
Moore et al. (1986) Embo. J. 5:919.
Delli Bovi et al. (1987) Cell 50:729.

(List continued on next page.)

Primary Examiner—Stephanie W. Zitomer
(74) Attorney, Agent, or Firm—Swanson & Bratschun LLC

(57) ABSTRACT

The present invention utilizes the SELEX (Systematic Evolution of Ligands for EXponential Enrichment) method for identifying and preparing nucleic acid ligands to basic fibroblast growth factor (bFGF) and thrombin. Included in the invention are nucleic acid ligands to bFGF which are inhibitors of bFGF and 2'-amino-modified RNA ligands to bFGF. Further included in the present invention are modified nucleotide sequences to thrombin based on the sequences of the RNA ligands identified. The modified RNA ligands to bFGF and thrombin exhibit increased in vivo stability.

3 Claims, 26 Drawing Sheets

OTHER PUBLICATIONS

Taira et al. (1987) Proc. Natl. Acad. Sci. USA 84:2980.
Zhan et al. (1988) Mol. Cell. Biol. 8:3487.
Marics et al. (1988) Oncogene 4:335.
Finch et al. (1989) Science 245:752.
Presta et al. (1986) Mol. Cell. Biol. 6:4060.
Moscatelli et al. (1986) Proc. Natl. Acad. Sci. USA 83:2091.
Folkman and Klagsbrun (1987) Science 235:442.
Gospodarowicz (1991) Cell Biology Reviews 25:307.
Zhang et al. (1991) Proc. Natl. Acad. Sci. USA 88:3446.
Eriksson et al. (1991) Proc. Natl. Acad. Sci. USA 88:3441.
Ago et al. (1991) J. Biochem. 110:360.
Zhu et al. (1991) Science 251:90.
Reidy et al. (1992) Circulation, Suppl. III 86:III–43.
Takahashi et al. (1990) Proc. Natl. Acad. Sci. USA 87:5710.
Middaugh et al. (1992) Biochemistry 31:9016.
Folkman et al. (1983) Science 221:719.
Crum et al. (1985) Science 230:1375.
Hobbs et al. (1973) Biochem. 12:5138.
Guschlbauer et al. (1977) Nucleic Acids Res. 4:1933.
Shibahara et al. (1987) Nucleic Acids Res. 15:4403.
Pieken et al. (1991) Science 253:314.
Tuerk et al. (1992) Proc. Natl. Acad. Sci. USA 89:6988.
Yarus and Berg (1970) Anal. Biochem. 35:450.
Lowary and Uhlenbeck (1987) Nucleic Acids Res. 15:10483.
Schneider et al. (1992) J. Mol. Biol. 228:862.
Irvine et al. (1991) J. Mol. Biol. 222:739.
Jellinek et al. (1993) Proc. Natl. Acad. Sci. USA 90:11227 Dec., 1993.
Tuerk et al. (1990) J. Mol. Biol. 213:749.
Gimbrone et al. (1974) JNCI 52:413.
Langer and Folkman (1976) Nature 263:797.
Polverini et al. (1977) Nature 269:804.
Moscatelli (1987) J. Cell Physiol. 131:123.
Rifkin and Moscatelli (1989) J. Cell. Biol. 109:1.
Basilico and Moscatelli (1992) Adv. Cancer Research 59:115.
Mignatti et al. (1989) J. Cell. Biol. 108:671.
Vlodavsky et al. (1991) Trends Biol. Sci. 16:268.
Mignatti and Rifkin (1991) J. Cell. Biochem. 47:201.
Ueno et al. (1992) J. Biol. Chem. 267:1470.
Armstrong et al. (1992) Cancer Research 52:2004.
Yayon et al. (1991) Cell 64:841.
Rapraeger et al. (1991) Science 252:1705.
Nugent and Edelman (1992) Biochemistry 31:8876.
Halaban et al. (1991) Ann. NY Acad. Sci. 638:232.
Fujimoto et al. (1991) Biochem. Biophys. Res. Commun. 180:386.
Hori et al. (1991) Cancer Res. 51:6180.
Ishai–Michaeli et al. (1992) Biochemistry 31:2080.
Turnbull et al. (1992) J. Biol. Chem. 267:10337.
Roghani and Moscatelli (1992) J. Biol. Chem. 267:22156.
Saffhill et al. (1970) J. Mol. Biol. 51:531.
Kacian et al. (1972) Proc. Natl. Acad. Sci. USA 69:3038.
Mills et al. (1973) Science 180:916.
Berndt and Phillips (1981) in *Platelets in Biology and Pathology* (Gordon, ed.) 43–74, Amsterdam: Elsevier/North Holland Biomedical Press.
Hanson and Harker (1988) Proc. Natl. Acad. Sci. USA 85:3184.
Eidt et al. (1989) J. Clin. Invest. 84:18.
Zimmerman et al. (1986) Ann. NY Acad. Sci. 485:349.
Marx (1992) Science 256:1278.
Bar–Shavit et al. (1983) Science 220:728.
Chen et al. (1976) Experimental Cell Research 101:41.
Chen and Buchanan (1975) Proc. Natl. Acad. Sci. USA 72:131.
Hattori et al. (1989) J. Biol. Chem. 264:7768.
Daniel et al. (1986) J. Biol. Chem. 261:9579.
Vu et al. (1991) Cell 64:1057.
Bock et al. (1992) Nature 355:564.

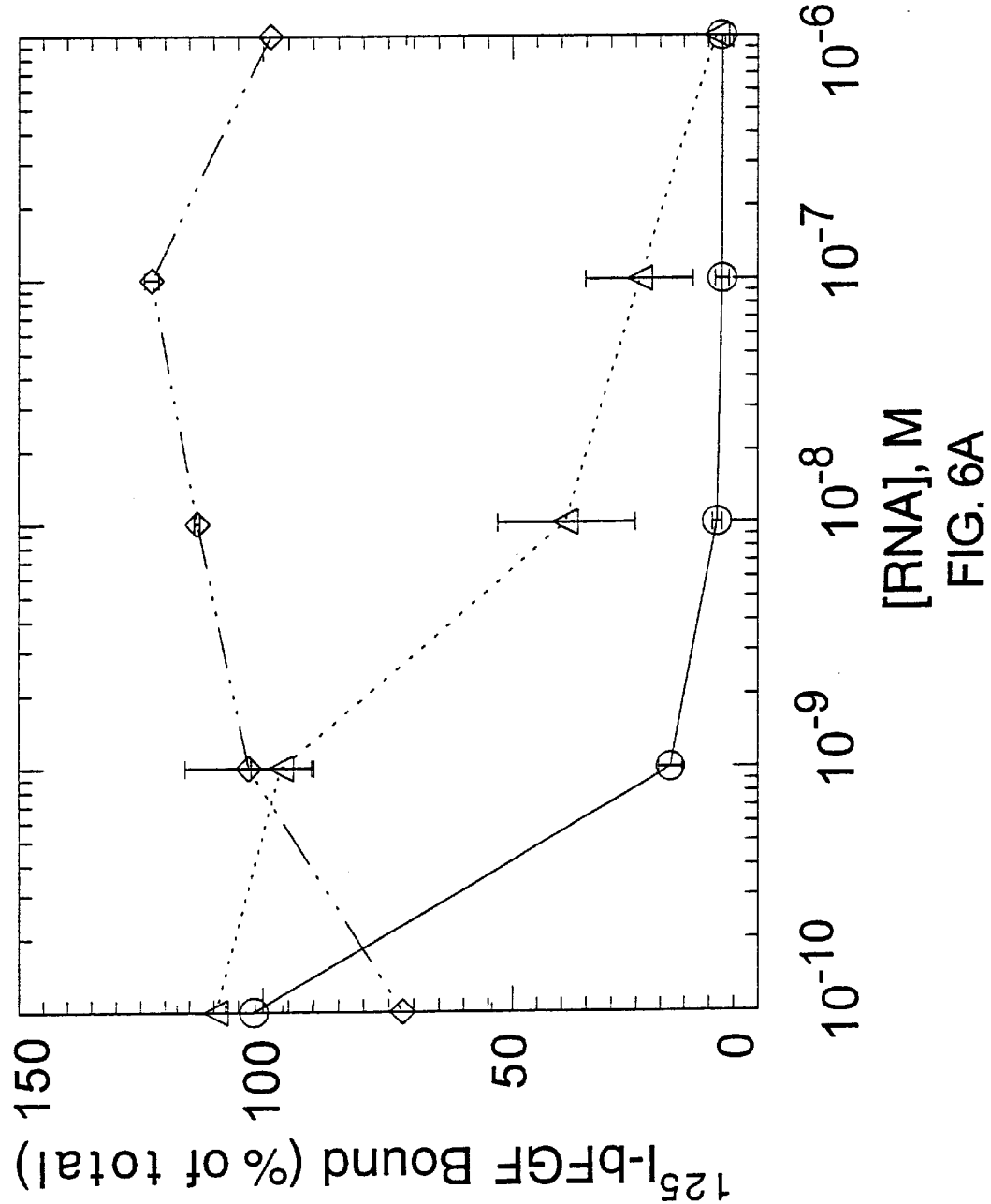

CLONE 6

```
         AGUUA
        A     G  U
       A       A
      G         G
      C    15   A
              C-G
              G-C
              A-U
              g-u
              u-c
              g-u
              a-c
              c-g
              g-u
              a-u
              g-c
                c
                u-g
                g-u
                u-a
                c-g
gggagaugc           cuaaacagcuuugucgacggg
        SEQ ID NO:211
                              FIG. 7
``` acgu = fixed region
ACGU = random region
ACGU = conserved region
——— = boundaries

CLONE 16

```
         G   A
      A U   G
   AGUUA 15  G
    A    C C
    G    G-C
    C    G-C    A
    U    C-G
         A    G
         C-G
         U-G
         A-U
         C  g
         g  u
         u  a
         c  g
         g  c
```
                            24                39 gggagaugccugucgagcau    uaaacagcuuugucacggg

SEQ ID NO:212
FIG. 7 (CONT'D)

CLONE 18

```
        AGUGA
      A     G
     G       U
     C  16   A
     U       G
     A       G
     G   —   C
     G   —   G
     G   —   C
         —   U
     U   —   A
     U   —   g
     G   —   u
     U   —   a
     U   —   g
``` gggagaugcccugucgagcaugcugA — cuaaagagcuuugucgacggg

SEQ ID NO:213
FIG. 7 (CONT'D)

acgu = fixed region
ACGU = random region
ACGU = conserved region
———— = boundaries

CLONE 27

```
     GGCUU
    C     U   G
   G       G G  C
  U         19  G
 G              C
  g            C
   u    c  g - C
         u - G
         a - U
         c - G
         g - C
         a - U
         g - U
         c - G
         u - A
         g - C
         u - g
```
gggagaugcc                    uagcuaaagagcuuugucgacggg

SEQ ID NO:214 acgu = fixed region
ACGU = random region
ACGU = conserved region
―――― = boundaries

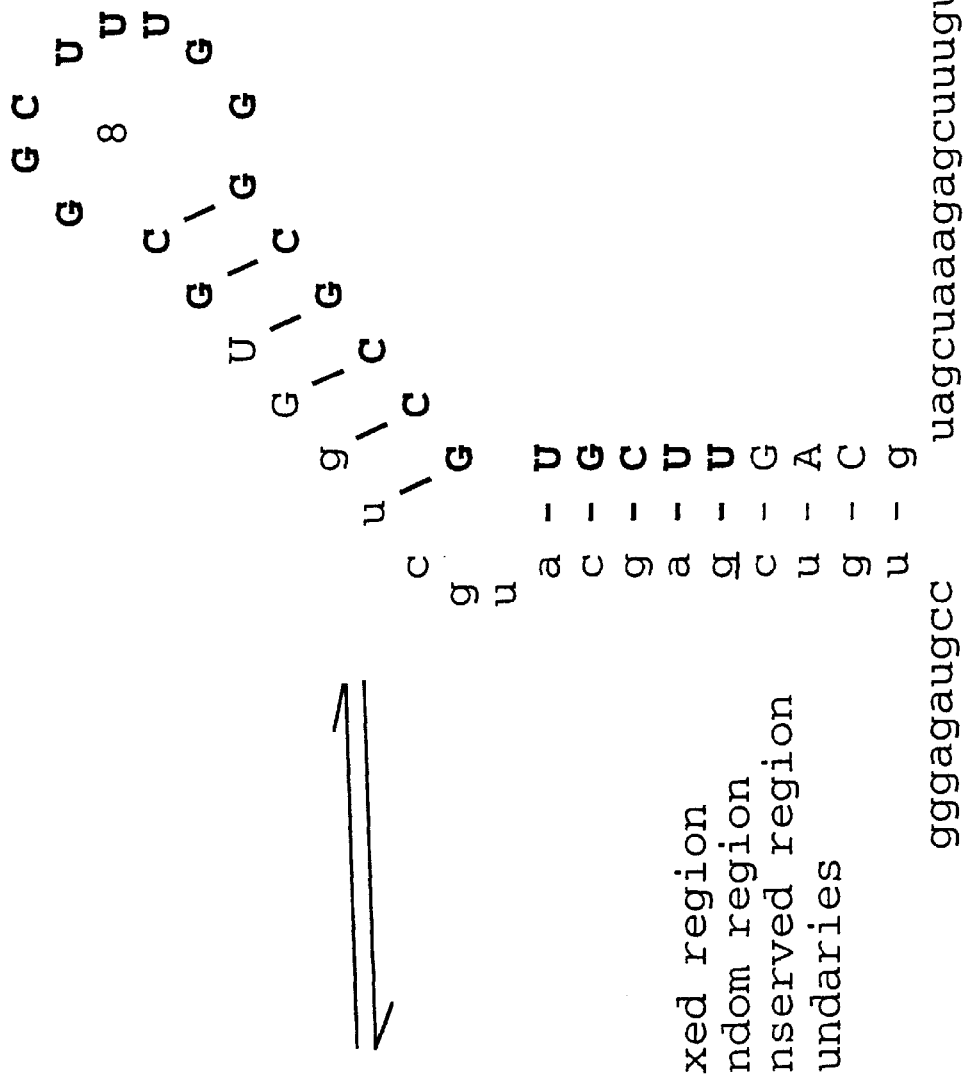

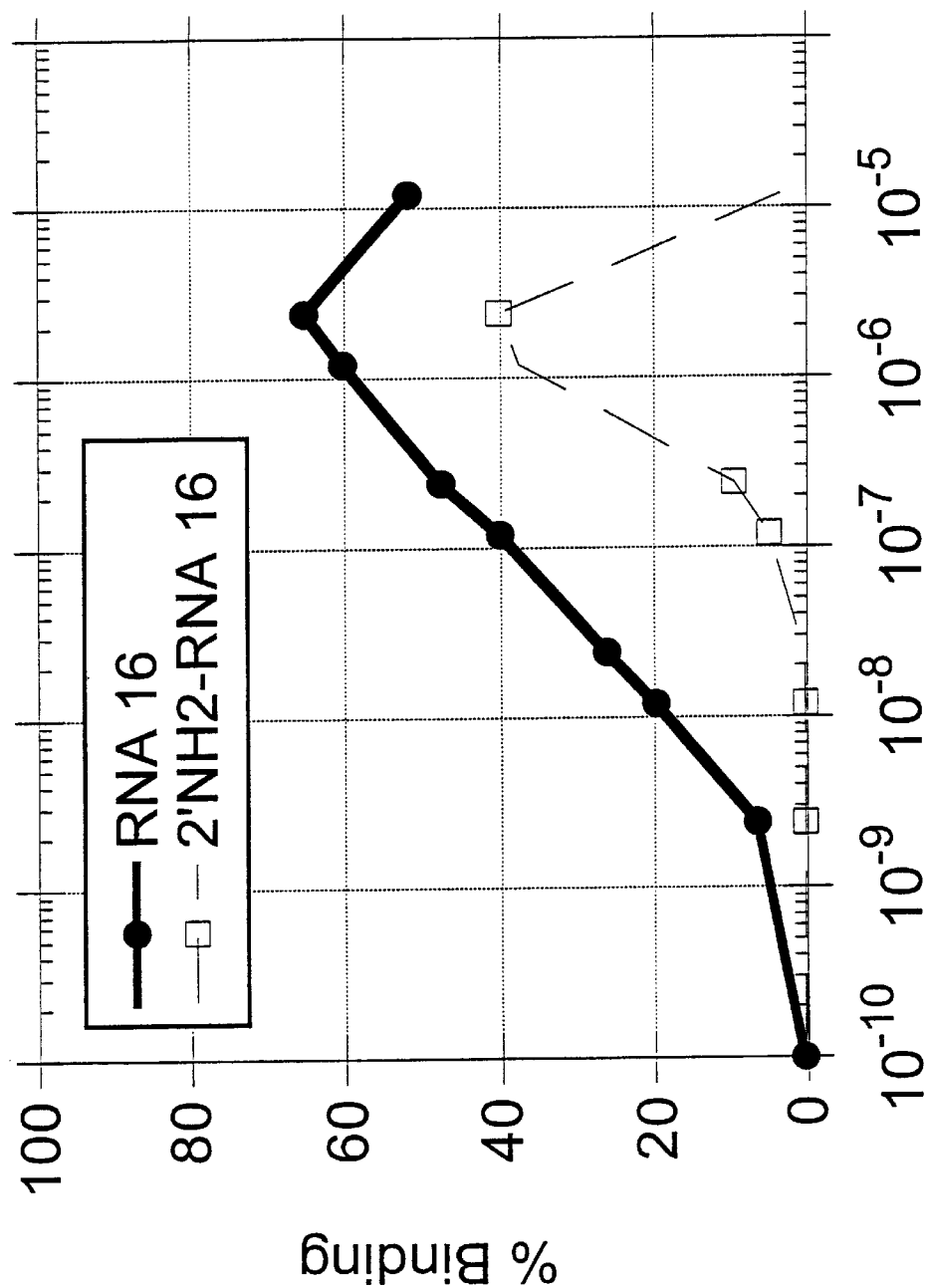

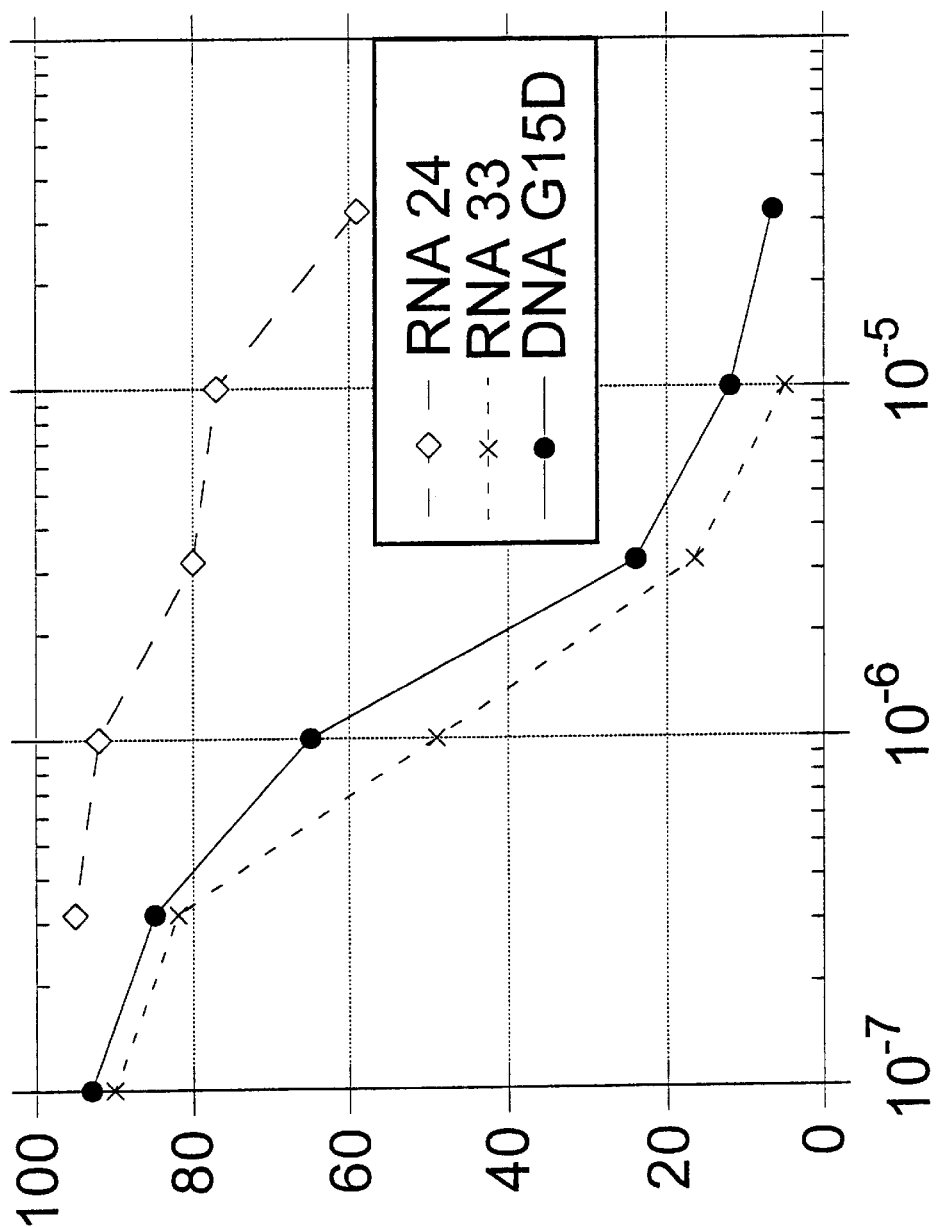

HIGH AFFINITY LIGANDS OF BASIC FIBROBLAST GROWTH FACTOR AND THROMBIN

This application is a Section 371 filing of PCT/US95/01458 filed Feb. 6, 1995, which is a Continuation-in-Part of U.S. patent application Ser. No. 08/195,005, filed Feb. 10, 1994, now issued as U.S. Pat. No. 5,459,015, and a Continuation-in-Part of U.S. patent application Ser. No. 08/219,012, filed Mar. 28, 1994, now issued as U.S. Pat. No. 5,543,293. U.S. application Ser. No. 08/195,005 is a Continuation-in-Part of U.S. patent application Ser. No. 08/061,691, filed Apr. 22, 1993, now abandoned, and a Continuation-in-Part of U.S. patent application Ser. No. 07/714,131, filed Jun. 10, 1991, now issued as U.S. Pat. No. 5,475,096. U.S. patent application Ser. No. 08/219,012 is a Continuation-in-Part of U.S. patent application Ser. No. 07/973,333, filed Nov. 6, 1992, now issued as U.S. Pat. No. 5,476,766, which is a Continuation-in-Part of U.S. patent application Ser. No. 07/714,131, filed Jun. 10, 1991, now issued as U.S. Pat. No. 5,475,096, and a Continuation-in-Part of U.S. patent application Ser. No. 07/536,428, filed Jun. 11, 1990, now abandoned. U.S. patent application Ser. No. 07/714,131 is a Continuation-in-Part of U.S. patent application Ser. No. 07/536,428.

FIELD OF THE INVENTION

Described herein are methods for identifying and preparing high-affinity nucleic acid ligands to basic fibroblast growth factor (bFGF) and thrombin. The method utilized herein for identifying such ligands is called SELEX, an acronym for Systematic Evolution of Ligands by EXponential Enrichment. Included within the scope of this invention are the specific ligands identified pursuant to such methods. Specifically, nucleic acid ligands are described to bFGF and thrombin. Also, included within the scope of this invention are modified nucleic acid ligands to bFGF and thrombin. Further included are mimetic nucleic acid ligands that are informed by the nucleic acid ligands identified herein. Specifically, disclosed are 2'-amino (2'-NH$_2$) modified RNA ligands to bFGF. 2'-NH$_2$-modified RNA ligands to bFGF were identified which inhibited the biological activity of bFGF both in vivo and in vitro. Further included in this invention are single stranded DNA ligands to thrombin and bFGF.

BACKGROUND OF THE INVENTION

Most proteins or small molecules are not known to specifically bind to nucleic acids. The known protein exceptions are those regulatory proteins such as repressors, polymerases, activators and the like which function in a living cell to bring about the transfer of genetic information encoded in the nucleic acids into cellular structures and the replication of the genetic material. Furthermore, small molecules such as GTP bind to some intron RNAs.

Living matter has evolved to limit the function of nucleic acids to a largely informational role. The central dogma, as postulated by Crick, both originally and in expanded form, proposes that nucleic acids (either RNA or DNA) can serve as templates for the synthesis of other nucleic acids through replicative processes that "read" the information in a template nucleic acid and thus yield complementary nucleic acids. All of the experimental paradigms for genetics and gene expression depend on these properties of nucleic acids: in essence, double-stranded nucleic acids are informationally redundant because of the chemical concept of base pairs and because replicative processes are able to use that base pairing in a relatively error-free manner.

The individual components of proteins, the twenty natural amino acids, possess sufficient chemical differences and activities to provide an enormous breadth of activities for both binding and catalysis. Nucleic acids, however, have been thought to have narrower chemical possibilities than proteins, but to have an informational role that allows genetic information to be passed from virus to virus, cell to cell, and organism to organism. In this context nucleic acid components, the nucleotides, possess only pairs of surfaces that allow informational redundancy within a Watson-Crick base pair. Nucleic acid components need not possess chemical differences and activities sufficient for either a wide range of binding or catalysis.

However, some nucleic acids found in nature do participate in binding to certain target molecules and even a few instances of catalysis have been reported. The range of activities of this kind is narrow compared to proteins and more specifically antibodies. For example, where nucleic acids are known to bind to some protein targets with high affinity and specificity, the binding depends on the exact sequences of nucleotides that comprise the DNA or RNA ligand. Thus, short double-stranded DNA sequences are known to bind to target proteins that repress or activate transcription in both prokaryotes and eukaryotes. Other short double-stranded DNA sequences are known to bind to restriction endonucleases, protein targets that can be selected with high affinity and specificity. Other short DNA sequences serve as centromeres and telomeres on chromosomes, presumably by creating ligands for the binding of specific proteins that participate in chromosome mechanics. Thus, double-stranded DNA has a well-known capacity to bind within the nooks and crannies of target proteins whose functions are directed to DNA binding. Single-stranded DNA can also bind to some proteins with high affinity and specificity, although the number of examples is smaller. From the known examples of double-stranded DNA binding proteins, it has become possible to describe some of the binding interactions as involving various protein motifs projecting amino acid side chains into the major groove of B form double-stranded DNA, providing the sequence inspection that allows specificity.

Double-stranded RNA occasionally serves as a ligand for certain proteins, for example, the endonuclease RNase III from *E. coli*. There are more known instances of target proteins that bind to single-stranded RNA ligands, although in these cases the single-stranded RNA often forms a complex three-dimensional shape that includes local regions of intramolecular double-strandedness. The amino-acyl tRNA synthetases bind tightly to tRNA molecules with high specificity. A short region within the genomes of RNA viruses binds tightly and with high specificity to the viral coat proteins. A short sequence of RNA binds to the bacteriophage T4-encoded DNA polymerase, again with high affinity and specificity. Thus, it is possible to find RNA and DNA ligands, either double- or single-stranded, serving as binding partners for specific protein targets. Most known DNA binding proteins bind specifically to double-stranded DNA, while most RNA binding proteins recognize single-stranded RNA. This statistical bias in the literature no doubt reflects the present biosphere's statistical predisposition to use DNA as a double-stranded genome and RNA as a single-stranded entity in the roles RNA plays beyond serving as a genome. Chemically there is no strong reason to dismiss single-stranded DNA as a fully able partner for specific protein interactions.

RNA and DNA have also been found to bind to smaller target molecules. Double-stranded DNA binds to various antibiotics, such as actinomycin D. A specific single-stranded RNA binds to the antibiotic thiostreptone; specific RNA sequences and structures probably bind to certain other antibiotics, especially those whose function is to inactivate ribosomes in a target organism. A family of evolutionary related RNAs binds with specificity and decent affinity to nucleotides and nucleosides (Bass, B. and Cech, T. (1984) Nature 308:820–826), as well as, to one of the twenty amino acids (Yarus, M. (1988) Science 240:1751–1758). Catalytic RNAs are now known as well, although these molecules perform over a narrow range of chemical possibilities, which are thus far related largely to phosphodiester transfer reactions and hydrolysis of nucleic acids.

Despite these known instances, the great majority of proteins and other cellular components are thought not to bind to nucleic acids under physiological conditions and such binding as may be observed is non-specific. Either the capacity of nucleic acids to bind other compounds is limited to the relatively few instances enumerated supra, or the chemical repertoire of the nucleic acids for specific binding is avoided (selected against) in the structures that occur naturally. The present invention is premised on the inventors' fundamental insight that nucleic acids as chemical compounds can form a virtually limitless array of shapes, sizes and configurations, and are capable of a far broader repertoire of binding and catalytic functions than those displayed in biological systems.

The chemical interactions have been explored in cases of certain known instances of protein-nucleic acid binding. For example, the size and sequence of the RNA site of bacteriophage R17 coat protein binding has been identified by Uhlenbeck (Uhlenbeck et al. (1983) J. Biomol. Structure Dynamics 1:539 and Romaniuk et al. (1987) Biochemistry 26:1563) and coworkers. The minimal natural RNA binding site (21 bases long) for the R17 coat protein was determined by subjecting variable-sized labeled fragments of the mRNA to nitrocellulose filter binding assays in which protein-RNA fragment complexes remain bound to the filter (Carey et al. (1983) Biochemistry 22:2601). A number of sequence variants of the minimal R17 coat protein binding site were created in vitro in order to determine the contributions of individual nucleic acids to protein binding. It was found that the maintenance of the hairpin loop structure of the binding site was essential for protein binding but, in addition, that nucleotide substitutions at most of the single-stranded residues in the binding site, including a bulged nucleotide in the hairpin stem, significantly affected binding. In similar studies, the binding of bacteriophage Qβ coat protein to its translational operator was examined (Witherell and Uhlenbeck (1989) Biochemistry 28:71). The Qβ coat protein RNA binding site was found to be similar to that of R17 in size, and in predicted secondary structure, in that it comprised about 20 bases with an 8 base pair hairpin structure which included a bulged nucleotide and a 3 base loop. In contrast to the R17 coat protein binding site, only one of the single-stranded residues of the loop is essential for binding and the presence of the bulged nucleotide is not required. The protein-RNA binding interactions involved in translational regulation display significant specificity.

Nucleic acids are known to form secondary and tertiary structures in solution. The double-stranded forms of DNA include the so-called B double-helical form, Z-DNA and superhelical twists (Rich, A. et al. (1984) Ann. Rev. Biochem. 53:791–846). Single-stranded RNA forms localized regions of secondary structure such as hairpin loops and pseudoknot structures (Schimmel, P. (1989) Cell 58:9–12). However, little is known concerning the effects of unpaired loop nucleotides on stability of loop structure, kinetics of formation and denaturation, thermodynamics, and almost nothing is known of tertiary structures and three dimensional shape, nor of the kinetics and thermodynamics of tertiary folding in nucleic acids (Tuerk, C. et al. (1988) Proc. Natl. Acad. Sci. USA 85:1364–1368).

A type of in vitro evolution was reported in replication of the RNA bacteriophage Qβ. (Mills, D. R. et al. (1967) Proc. Natl. Acad. Sci USA 58:217–224; Levisohn, R. and Spiegelman, S. (1968) Proc. Natl. Acad. Sci. USA 60:866–872; Levisohn, R. and Spiegelman, S. (1969) Proc. Natl. Acad. Sci. USA 63:805–811; Saffhill, R. et al. (1970) J. Mol. Biol. 51:531–539; Kacian, D. L. et al. (1972) Proc. Natl. Acad. Sci. USA 69:3038–3042; Mills, D. R. et al. (1973) Science 180:916–927). The phage RNA serves as a poly-cistronic messenger RNA directing translation of phage-specific proteins and also as a template for its own replication catalyzed by Qβ RNA replicase. This RNA replicase was shown to be highly specific for its own RNA templates. During the course of cycles of replication in vitro small variant RNAs were isolated which were also replicated by Qβ replicase. Minor alterations in the conditions under which cycles of replication were performed were found to result in the accumulation of different RNAs, presumably because their replication was favored under the altered conditions. In these experiments, the selected RNA had to be bound efficiently by the replicase to initiate replication and had to serve as a kinetically favored template during elongation of RNA. Kramer et al. (1974) J. Mol. Biol. 89:719 reported the isolation of a mutant RNA template of Qβ replicase, the replication of which was more resistant to inhibition by ethidium bromide than the natural template. It was suggested that this mutant was not present in the initial RNA population, but was generated by sequential mutation during cycles of in vitro replication with Qβ replicase. The only source of variation during selection was the intrinsic error rate during elongation by Qβ replicase. In these studies what was termed "selection" occurred by preferential amplification of one or more of a limited number of spontaneous variants of an initially homogenous RNA sequence. There was no selection of a desired result, only that which was intrinsic to the mode of action of Qβ replicase.

Joyce and Robertson (Joyce (1989) in *RNA: Catalysis, Splicing, Evolution,* Belfort and Shub (eds.), Elsevier, Amsterdam pp. 83–87; and Robertson and Joyce (1990) Nature 344:467–468) reported a method for identifying RNAs which specifically cleave single-stranded DNA. The selection for catalytic activity was based on the ability of the ribozyme to catalyze the cleavage of a substrate ssRNA or DNA at a specific position and transfer the 3'-end of the substrate to the 3'-end of the ribozyme. The product of the desired reaction was selected by using a deoxyoligonucleotide primer which could bind only to the completed product across the junction formed by the catalytic reaction and allowed selective reverse transcription of the ribozyme sequence. The selected catalytic sequences were amplified by attachment of the promoter of T7 RNA polymerase to the 3'-end of the cDNA, followed by transcription to RNA. The method was employed to identify from a small number of ribozyme variants the variant that was most reactive for cleavage of a selected substrate.

The prior art has taught or suggested only a limited range of chemical functions for nucleic acids in their interactions with other substances, namely, as targets for proteins that have evolved to bind certain specific oligonucleotide sequences; and more recently, as catalysts with a limited range of activities. Prior "selection" experiments have been limited to a narrow range of variants of a previously described function.

U.S. patent application Ser. No. 07/536,428, filed Jun. 11, 1990, entitled Systematic Evolution of Ligands by Exponential Enrichment, now abandoned, U.S. Pat. No. 5,270,163, issued Dec. 14, 1993, and U.S. patent application Ser. No. 07/714,131, filed Jun. 10, 1991, now U.S. Pat. No. 5,475,096, both entitled Nucleic Acid Ligands (See also WO91/19813) describe a fundamentally novel method for identifying a nucleic acid ligand for any desired target. Each of these applications, collectively referred to herein as the SELEX Patent Applications, is specifically incorporated herein by reference.

The method of the SELEX Patent Applications is based on the unique insight that nucleic acids have sufficient capacity for forming a variety of two- and three-dimensional structures and sufficient chemical versatility available within their monomers to act as ligands (form specific binding pairs) with virtually any chemical compound, whether large or small in size.

The method involves selection from a mixture of candidates and step-wise iterations of structural improvement, using the same general selection theme, to achieve virtually any desired criterion of binding affinity and selectivity. Starting from a mixture of nucleic acids, preferably comprising a segment of randomized sequence, the method, termed SELEX herein, includes steps of contacting the mixture with the target under conditions favorable for binding, partitioning unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired.

While not bound by theory, SELEX is based on the inventors' insight that within a nucleic acid mixture containing a large number of possible sequences and structures there is a wide range of binding affinities for a given target. A nucleic acid mixture comprising, for example, a 20 nucleotide randomized segment can have $4^{20}$ candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved on repetition of the cycle. The method may be used to sample as many as about $10^{18}$ different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/amplification iterations.

In one embodiment of the method of the SELEX Patent Applications, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX until a single nucleic acid ligand is identified. The target-specific nucleic acid ligand solution may include a family of nucleic acid structures or motifs that have a number of conserved sequences and a number of sequences which can be substituted or added without significantly effecting the affinity of the nucleic acid ligands to the target. By terminating the SELEX process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX procedures with contiguous randomized segments be initiated with nucleic acid sequences containing a randomized segment of between about 20–50 nucleotides.

The SELEX Patent Applications also describe methods for obtaining nucleic acid ligands that bind to more than one site on the target molecule, and to nucleic acid ligands that include non-nucleic acid species that bind to specific sites on the target. The SELEX method provides means for isolating and identifying nucleic acid ligands which bind to any envisionable target. However, in preferred embodiments the SELEX method is applied to situations where the target is a protein, including both nucleic acid-binding proteins and proteins not known to bind nucleic acids as part of their biological function.

Basic fibroblast growth factor (bFGF) is a multifunctional effector for many cells of mesenchymal and neuroectodermal origin (Rifkin & Moscatelli (1989) J. Cell Biol. 109:1; Baird & Bohlen (1991) in *Peptide Growth Factors and Their Receptors* (Sporn, M. B. & Roberts, A. B., eds.); pp. 369–418, Springer, N.Y.; Basilico & Moscatelli (1992) Adv. Cancer Res. 59:115). It is one of the most studied and best characterized members of a family of related proteins that also includes acidic FGF (Jaye et al. (1986) Science 233:541; Abraham et al. (1986) Science 233:545), int-2 (Moore et al. (1986) EMBO J. 5:919), kFGF/hst/KS3 (Delli Bovi et al. (1987) Cell 50:729; Taira et al. (1987) Proc. Natl. Acad. Sci. USA 84:2980), FGF-5 (Zhan et al. (1988) Mol. Cell. Biol. 8:3487), FGF-6 (Marics et al. (1988) Oncogene 4:335) and keratinocyte growth factor/FGF-7 (Finch et al. (1989) Science 245:752).

In vitro, bFGF stimulates cell proliferation, migration and induction of plasminogen activator and collagenase activities (Presta et al. (1986) Mol. Cell. Biol. 6:4060; Moscatelli et al. (1986) Proc. Natl. Acad. Sci. USA 83:2091; Mignatti et al. (1989) J. Cell Biol. 108:671). In vivo, it is one of the most potent inducers of neovascularization. Its angiogenic activity in vivo suggests a role in tissue remodeling and wound healing, but also, in some disease states that are characterized by pathological neovascularization such as tumor proliferation, tumor metastasis, diabetic retinopathy and rheumatoid arthritis (Folkman & Klagsbrun (1987) Science 235:442; Gospodarowicz (1991) Cell Biology Reviews 25:307).

Although bFGF does not have a signal sequence for secretion, it is found on both sides of the plasma membrane, presumably being exported via exocytosis (Vlodavsky et al. (1991) Trends Biol. Sci. 16:268; Mignatti & Rifkin (1991) J. Cell. Biochem. 47:201). In the extracellular matrix, it is typically associated with a fraction that contains heparan sulfate proteoglycans. Indeed, heparin affinity chromatography has been a useful method for purification of this and other heparin-binding growth factors. Heparin is a glycosoaminoglycan composed of chains of alternating residues of D-glucosamine and uronic acid. In cell culture, bFGF binds to low- and high-affinity sites. The low-affinity sites are composed of cell-associated heparan sulfate proteoglycans to which bFGF binds with approximately nanomolar affinity (Moscatelli (1987) J. Cell. Physiol. 131:123). All biological effects of bFGF are mediated through interaction with the high-affinity binding sites (10–100 pM) that represent the dimeric tyrosine kinase FGF receptor (Ueno et al. (1992) J. Biol. Chem. 267:1470).

Five FGF receptor genes have been identified to date, each of which can produce several structural variants as a result of alternative mRNA splicing (Armstrong et al. (1992) Cancer Res. 52:2004; Ueno et al. (1992) J. Biol. Chem. 267:1470). There is substantial evidence that the low- and the high-affinity binding sites act cooperatively in determining the overall affinity of bFGF. Experiments with mutant cell lines that are deficient in glycosaminoglycan synthesis (Yayon et al. (1991) Cell 64:841) or heparitinase treated cells (Rapraeger et al. (1991) Science 252:1705) have shown that binding of either cell-associated heparan sulfate or, in its absence, exogenously added heparin to bFGF is required for signaling via the tyrosine kinase receptor. Recent resolution of observed Kd into its kinetic components demonstrates that while the association rates of bFGF to the low- and the high-affinity sites are comparable, the dissociation rate of bFGF from the cell surface receptor is 23-fold slower than that for the cell-associated heparan sulfate (Nugent & Edelman (1992) Biochemistry 31:8876). The slower off-rate, however, is only observed when the receptor is bound to the cell surface suggesting that simultaneous binding to both sites contributes to the overall high-affinity binding. This is plausible in light of the observation that the heparin-binding and the receptor-binding sites are located on adjacent, but separate regions of the molecule, as determined from the recently solved X-ray crystal structure of bFGF (Zhang et al. (1991) Proc. Natl. Acad. Sci. USA 88:3446; Eriksson et al. (1991) Proc. Natl. Acad. Sci. USA 88:3441; Ago et al. (1991) J. Biochem. 110:360; Zhu et al. (1991) Science 251:90).

The idea that bFGF antagonists may have useful medicinal applications is not new (reviewed in Gospodarowicz (1991) Cell Biology Reviews 25:307). bFGF is now known to play a key role in the development of smooth-muscle cell lesions following vascular injury (Reidy et al. (1992) Circulation, Suppl. III 86:III-43). Overexpression of bFGF (and other members of the FGF family) is correlated with many malignant disorders (Halaban et al. (1991) Ann. N. Y. Acad. Sci. 638:232; Takahashi et al. (1990) Proc. Natl. Acad. Sci. USA 87:5710; Fujimoto et al. (1991) Biochem. Biophys. Res. Commun. 180:386) and recently, neutralizing anti-bFGF antibodies have been found to suppress solid tumor growth in vivo by inhibiting tumor-linked angiogenesis (Hori et al. (1991) Cancer Res. 51:6180). Notable in this regard is the recent therapeutic examination of suramin, a polysulfated naphthalene derivative with known antiprotozoal activity, as an anti-tumor agent. Suramin is believed to inhibit the activity of bFGF through binding in the polyanion binding site and disrupting interaction of the growth factor with its receptor (Middaugh et al. (1992) Biochemistry 31:9016; Eriksson et al. (1991) Proc. Natl. Acad. Sci. USA 88:3441). In addition to having a number of undesirable side effects and substantial toxicity, suramin is known to interact with several other heparin-binding growth factors which makes linking of its beneficial therapeutic effects to specific drug-protein interactions difficult (La Rocca et al. (1990) Cancer Cells 2:106). Anti-angiogenic properties of certain heparin preparations have also been observed (Folkman et al. (1983) Science 221:719; Crum et al. (1985) Science 230:1375) and these effects are probably based at least in part on their ability to interfere with bFGF signaling. While the specific heparin fraction that contributes to bFGF binding is now partially elucidated (Ishai-Michaeli et al. (1992) Biochemistry 31:2080; Turnbull et al. (1992) J. Biol. Chem. 267:10337), a typical heparin preparation is heterogeneous with respect to size, degree of sulfation and iduronic acid content. Additionally, heparin also affects many enzymes and growth factors. Excluding monoclonal antibodies, therefore, specific antagonists of bFGF are not known.

Thrombin is a multifunctional serine protease that has important procoagulant and anticoagulant activities. As a procoagulant enzyme thrombin clots fibrinogen, activates clotting factors V, VIII, and XIII, and activates platelets. The specific cleavage of fibrinogen by thrombin initiates the polymerization of fibrin monomers, a primary event in blood clot formation. The central event in the formation of platelet thrombi is the activation of platelets from the "nonbinding" to the "binding" mode and thrombin is the most potent physiologic activator of platelet aggregation (Berndt and Phillips (1981) in *Platelets in Biology and Pathology*, J. L. Gordon, ed. (Amsterdam:Elsevier/North Holland Biomedical Press), pp. 43–74; Hansen and Harker (1988) Proc. Natl. Acad. Sci. USA 85:3184–3188; Eidt et al. (1989) J. Clin. Invest. 84:18–27). Thus, as a procoagulant, thrombin plays a key role in the arrest of bleeding (physiologic hemostasis) and formation of vasoocclusive thrombi (pathologic thrombosis).

As an anticoagulant thrombin binds to thrombomodulin (TM), a glycoprotein expressed on the surface of vascular endothelial cells. TM alters substrate specificity from fibrinogen and platelets to protein C through a combination of an allosteric change in the active site conformation and an overlap of the TM and fibrinogen binding sites on thrombin. Activated protein C, in the presence of a phospholipid surface, $Ca^{2+}$, and a second vitamin K-dependent protein cofactor, protein S, inhibits coagulation by proteolytically degrading factors Va and VIIIa. Thus, the formation of the thrombin-TM complex converts thrombin from a procoagulant to an anticoagulant enzyme, and the normal balance between these opposing activities is critical to the regulation of hemostasis.

Thrombin is also involved in biological responses that are far removed from the clotting system (reviewed in Zimmerman et al. (1986) Ann. N. Y. Acad. Sci. 485:349–368; Marx (1992) Science 256:1278–1280). Thrombin is chemotactic for monocytes (Bar-Shavit et al. (1983) Science 220:728–730), mitogenic for lymphocytes (Chen et al. (1976) Exp. Cell Res. 101:41–46), mesenchymal cells (Chen and Buchanan (1975) Proc. Natl. Acad. Sci. USA 72:131–135), and fibroblasts (Marx (1992) Science 256:1278–1280). Thrombin activates endothelial cells to express the neutrophil adhesive protein GMP-140 (PADGEM) (Hattori et al. (1989) J. Biol. Chem. 264:7768–7771) and produce platelet-derived growth factor (Daniel et al. (1986) J. Biol. Chem. 261:9579–9582). Recently it has been shown that thrombin causes cultured nerve cells to retract their neurites (reviewed in Marx (1992) Science 256:1278–1280).

The mechanism by which thrombin activates platelets and endothelial cells is through a functional thrombin receptor found on these cells. A putative thrombin cleavage site (LDR/S) in the receptor suggests that the thrombin receptor is activated by proteolytic cleavage of the receptor. This cleavage event "unmasks" an N-terminal domain which then acts as the ligand, activating the receptor (Vu et al. (1991) Cell 64:1057–1068).

Vascular injury and thrombus formation represent the key events in the pathogenesis of various vascular diseases, including atherosclerosis. The pathogenic processes of the activation of platelets and/or the clotting system leading to thrombosis in various disease states and in various sites, such as the coronary arteries, cardiac chambers, and prosthetic heart valves, appear to be different. Therefore, the use of a platelet inhibitor, an anticoagulant, or a combination of both may be required in conjunction with thrombolytics to open closed vessels and prevent reocclusion.

Controlled proteolysis by compounds of the coagulation cascade is critical for hemostasis. As a result, a variety of complex regulatory systems exist that are based, in part, on a series of highly specific protease inhibitors. In a pathological situation functional inhibitory activity can be interrupted by excessive production of active protease or inactivation of inhibitory activity. Perpetuation of inflammation in response to multiple trauma (tissue damage) or infection (sepsis) depends on proteolytic enzymes, both of plasma cascade systems, including thrombin, and lysosomal origin. Multiple organ failure (MOF) in these cases is enhanced by the concurrently arising imbalance between proteases and their inhibitory regulators. An imbalance of thrombin activity in the brain may lead to neurodegenerative diseases.

Thrombin is naturally inhibited in hemostasis by binding to antithrombin III (ATIII), in a heparin-dependent reaction. Heparin exerts its effect through its ability to accelerate the action of ATIII. In the brain, protease nexin (PN-1) may be the natural inhibitor of thrombin to regulate neurite outgrowth.

As stated above, heparin is a glycosoaminoglycan composed of chains of alternating residues of D-glucosamine and uronic acid. Its anticoagulant effect is mediated through its interaction with ATIII. When heparin binds ATIII, the conformation of ATIII is altered, and it becomes a significantly enhanced inhibitor of thrombin. Although heparin is generally considered to be effective for certain indications, it is believed that the physical size of the ATIII●heparin complex prevents access to much of the biologically active thrombin in the body, thus diminishing its ability to inhibit clot formation. Side effects of heparin include bleeding, thrombocytopenia, osteoporosis, skin necrosis, alpe, hypersensitivity and hypoaldoseronism.

Hirudin is a potent peptide inhibitor of thrombin derived from the European medicinal leech *Hirudis medicinalis*. Hirudin inhibits all known functions of α-thrombin, and has been shown to bind thrombin at two separate sites kinetically; a high affinity site at or near the catalytic site for serine protease activity and a second anionic exosite. The anionic exosite also binds fibrinogen, heparin, TM and probably the receptor involved in mediating the activation of platelets and endothelial cells. A C-terminal hirudin peptide—which has been shown by co-crystallization with thrombin to bind in the anionic exosite—has inhibitory effects on fibrin formation, platelet and endothelial cell activation, and Protein C activation via TM binding, presumably by competing for binding at this site. This peptide does not inhibit proteolytic activity towards tripeptide chromogenic substrates, Factor V or X.

The structure of thrombin makes it a particularly desirable target for nucleic acid binding, due to the anionic exosite. Site-directed mutagenesis within this site has shown that fibrinogen-clotting and TM binding activities are separable. Conceivably, an RNA ligand could be selected that has procoagulatory and/or anticoagulatory effects depending on how it interacts with thrombin, i.e., which substrate it mimics.

A single stranded DNA ligand to thrombin has been prepared according to a procedure identical to SELEX. See, Bock et al. (1992) Nature 355:564–565. A consensus ligand was identified after relatively few rounds of SELEX were performed, that was shown to have some ability to prevent clot formation in vitro. The ligand is the 15mer DNA 5'GGTTGGTGTGGTTGG-3', referred to herein as G15D (SEQ ID NO:189). The symmetrical nature of the primary sequence suggests that G15D has a regular fixed tertiary structure. The Kd of G15D to thrombin is about $2\times10^{-7}$. For effective thrombin inhibition as an anticoagulant, the stronger the affinity of the ligand to thrombin the better.

SUMMARY OF THE INVENTION

The present invention includes methods for identifying and producing nucleic acid ligands and the nucleic acid ligands so identified and produced. Nucleic acid sequences are provided that are ligands of bFGF and thrombin. Specifically, RNA and DNA sequences are provided that are capable of binding specifically to bFGF and to thrombin. Included within the invention are the nucleic acid ligand sequences shown in Tables II–IV (SEQ ID NOS:7–69), Table VIII (SEQ ID NOS:101–185), Tables XII–XIII (SEQ ID NOS:192–214), Table XV–XVIII (SEQ ID NOS:216–319) and XXI–XXII (SEQ ID NOS:330–445).

Also included in this invention are nucleic acid ligands of bFGF that are inhibitors of bFGF. Specifically, RNA ligands are identified and described which inhibit the binding of bFGF to its receptors.

Further included in this invention is a method of identifying nucleic acid ligands and ligand sequences to bFGF and thrombin comprising the steps of a) preparing a candidate mixture of nucleic acids; b) partitioning between members of said candidate mixture on the basis of affinity to bFGF or thrombin; and c) amplifying the selected molecules to yield a mixture of nucleic acids enriched for nucleic acid sequences with a relatively higher affinity for binding to bFGF or thrombin.

More specifically, the present invention includes the RNA ligands to bFGF and to thrombin identified according to the above-described method, including those ligands listed in Tables II–IV and Tables XII and XIII and Tables XVII and XVIII. Also included are RNA ligands to bFGF and thrombin that are substantially homologous to any of the given ligands and that have substantially the same ability to bind and inhibit bFGF and thrombin. Further included in this invention are RNA ligands to bFGF and thrombin that have substantially the same structural form as the ligands presented herein and that have substantially the same ability to bind and inhibit bFGF and thrombin.

The present invention also includes modified nucleotide sequences based on the nucleic acid ligand sequences identified herein and mixtures of the same. Specifically included in this invention are RNA ligands, that have been modified at the ribose and/or phosphate and/or base positions to increase the in vivo stability of the RNA ligand. Other modification to RNA ligands are encompassed by this invention, including specific alterations in base sequence, and additions of nucleic acids or non-nucleic acid moieties to the original compound. More specifically, included in this invention are the RNA ligands to bFGF, comprising nucleotides modified at the 2'-amino (2'-NH$_2$) position shown in Table VIII. The 2'-NH$_2$-modified RNA ligands possess improved in vivo stability.

The SELEX method utilizing a single-stranded DNA library of nucleic acids was also performed using bFGF and thrombin as the target. Included within the invention, therefore, are the single-stranded DNA ligands to bFGF shown in Tables XXI and XXII and to thrombin shown in Tables XV and XVI. Also included in the invention are DNA ligands to thrombin that are substantially homologous to the DNA ligands identified herein and that have substantially the same ability to bind thrombin. Further included in this invention are DNA ligands to thrombin that have substantially the same structural form as the DNA ligands presented herein and that have substantially the same ability to bind thrombin.

BRIEF DESCRIPTION OF THE FIGURES

FIGS. 6A and 6B show 2'-NH$_2$-modified bFGF RNA ligand inhibition of $^{125}$I-bFGF binding to the low-affinity (FIG. 6A) and the high-affinity (FIG. 6B) cell surface receptors. The ligands tested were 21A (SEQ ID NO:104) (Δ), 21A-t (SEQ ID NO:186) (○), and random RNA A (◊).

FIG. 7 shows the possible secondary structures of the 76 nucleotide Class I thrombin RNA clones 6 (SEQ ID NO:211), 16 (SEQ ID NO:212), and 18 (SEQ ID NO:213), and the Class II 72 nucleotide clone 27 (SEQ ID NO:214) as determined from boundary experiments. Boundaries are underlined. The 5' and 3' fixed regions are depicted by small case lettering, the 30N random region by caps and the conserved region by bold caps. The hairpin structures that were synthesized are boxed with the total number of nucleotides indicated.

In FIG. 8A RNAs with unique 30N sequence motifs (see Table XII) were chosen for binding analysis with human thrombin (Sigma), including the three from Class I: RNA 6 (SEQ ID NO:192), RNA 16 (SEQ ID NO:198), and RNA 18 (SEQ ID NO:199), and one from Class II: RNA 27 (SEQ ID NO:209). Binding of bulk RNA sequences of the 30N3 candidate mixture is also shown. In FIG. 8B, binding of class I RNA clones 6, 16, 18 and Class II RNA clone 27 is shown, but with human thrombin from Enzyme Research Laboratories.

FIGS. 9A and 9B depict a binding comparison of thrombin RNA ligands between unmodified RNA and RNA with pyrimidines modified to contain the 2'-NH$_2$ ribose nucleotide. FIG. 9A depicts the binding comparison of bulk RNA 30N candidate mixture and 2'-NH$_2$ modified 30N candidate mixture. FIG. 9B depicts the binding comparison of Class I RNA 16 (SEQ ID NO:198) and 2'-NH$_2$ modified RNA 16.

FIGS. 10A and 10B depict the competition experiments between the 15mer ssDNA G15D (SEQ ID NO:189) and the thrombin RNA hairpin ligands of this invention for binding to human thrombin. In FIG. 10A the concentration of the tracer G15D is equal to the concentration of protein at 1 μM. The competitors for binding include G15D itself, the 24 and 39 nucleotide RNA hairpin structures from Class I RNA 16 (SEQ ID NO:212), and the 33 nucleotide RNA hairpin structure from Class II RNA 27 (SEQ ID NO:214) (see FIG. 7). Binding is expressed as the relative fraction G15D bound, which is the ratio of G15D binding with competitor to G15D binding without competitor. In FIG. 10B 33 nucleotide hairpin RNA is the tracer and the concentration of the tracer is equal to the concentration of protein at 300 ηM. The competitors for binding include the ssDNA G15D and RNA 24.

DETAILED DESCRIPTION OF THE PREFERRED EMBODIMENTS

Figure 1:
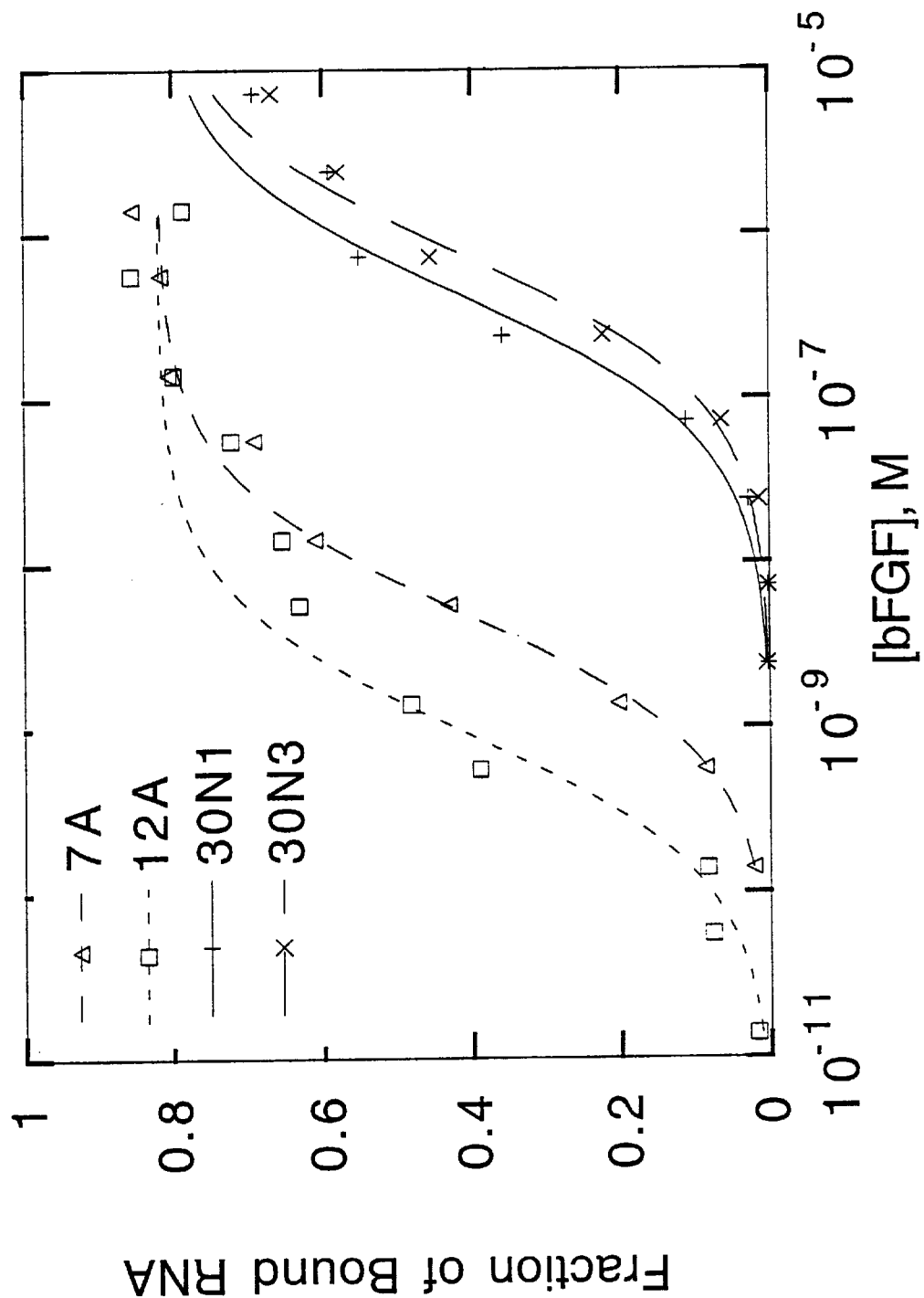
FIG. 1 shows binding curves for bFGF Family 1 ligand 7A (SEQ ID NO:10) (Δ), Family 2 ligand 12A (SEQ ID NO:25) (□), random RNA, SELEX experiment A(+) and random RNA, SELEX experiment B (x). The fraction of RNA bound to nitrocellulose filters is plotted as a function of free protein concentration and data points were fitted to equation 2 as defined in Example 3 below. The following concentrations of RNA were used: <100 pM for 7A and 12A, and 10 nM for random RNAs. Binding reactions were done at 37° C. in phosphate buffered saline containing 0.01% human serum albumin.

This application is an extension and an application of the method for identifying nucleic acid ligands referred to as SELEX. The SELEX method is described in detail in U.S. patent application Ser. No. 07/714,131, filed Jun. 10, 1991, entitled Nucleic Acid Ligands, now U.S. Pat. No. 5,475,096, U.S. patent application Ser. No. 07/536,428, filed Jun. 11, 1990, entitled Systematic Evolution of Ligands by EXponential Enrichment, now abandoned, U.S. patent application Ser. No. 07/931,473 filed Aug. 17, 1992, now U.S. Pat. No. 5,270,163, entitled Nucleic Acid Ligands. These applications are collectively referred to herein as the SELEX Applications. The full text of these applications, including but not limited to, all definitions and descriptions of the SELEX process, are specifically incorporated herein by reference.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (i.e., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including both protein targets wherein the protein is and is not a nucleic acid binding protein.

SELEX provides high affinity ligands of a target molecule. This represents a singular achievement that is unprecedented in the field of nucleic acids research. The present invention applies the SELEX procedure to the specific targets, bFGF and thrombin. In the Example section below, the experimental parameters used to isolate and identify the nucleic acid ligand solutions to bFGF and thrombin are described.

In order to produce nucleic acids desirable for use as a pharmaceutical, it is preferred that the nucleic acid ligand 1) binds to the target in a manner capable of achieving the desired effect on the target; 2) be as small as possible to obtain the desired effect; 3) be as stable as possible; and 4) be a specific ligand to the chosen target. In most, if not all situations, it is preferred that the nucleic acid ligand have the highest possible affinity to the target.

In co-pending and commonly assigned U.S. patent application Ser. No. 07/964,624, filed Oct. 21, 1992, now U.S. Pat. No. 5,496,938, methods are described for obtaining improved nucleic acid ligands after SELEX has been performed. This application, entitled Methods of Producing Nucleic Acid Ligands is specifically incorporated herein by reference. Included in this application are methods relating to assays of ligand effects on target molecules; affinity assays of the ligands; information boundaries determination; quantitative and qualitative assessment of individual nucleotide contributions to affinity via secondary SELEX, nucleotide substitution, and chemical modification experiments; and structural determination. The present invention includes improvements to the nucleic acid ligand solutions derived according to these procedures.

This invention includes the specific nucleic acid ligands shown in Tables II–IV, Table VIII, Tables XII–XIII, Tables XV–XVIII and Tables XXI–XXII. These tables include unmodified RNA ligands to bFGF (Tables II–IV (SEQ ID NOS: 7–69) and Tables XVII–XVIII (SEQ ID NOS: 281–319)), modified RNA ligands to bFGF (Table VIII (SEQ ID NOS:101–185)), DNA ligands to bFGF (Tables XXI–XXII (SEQ ID NOS:330–444)), unmodified RNA ligands to thrombin (Tables XII–XIII (SEQ ID NOS:192–214)) and DNA ligands to thrombin (Tables XV–XVI (SEQ ID NOS:216–280)) identified by the SELEX method as described herein. The scope of the ligands covered by this invention extends to all ligands to bFGF and thrombin identified according to the SELEX procedure. More specifically, this invention includes nucleic acid sequences that are substantially homologous to and that have substantially the same ability to bind bFGF and thrombin as the specific nucleic acid ligands shown in Tables II–IV, VIII, XII–XIII, XV–XVIII and XXI–XXII. By substantially homologous, it is meant, a degree of primary sequence homology in excess of 70%, most preferably in excess of 80%. Substantially the same ability to bind bFGF or thrombin means that the affinity is within two orders of magnitude of the affinity of the ligands described herein. It is well within the skill of those of ordinary skill in the art to determine whether a given sequence—substantially homologous to those specifically described herein—has substantially the same ability to bind bFGF or thrombin.

Figure 4:
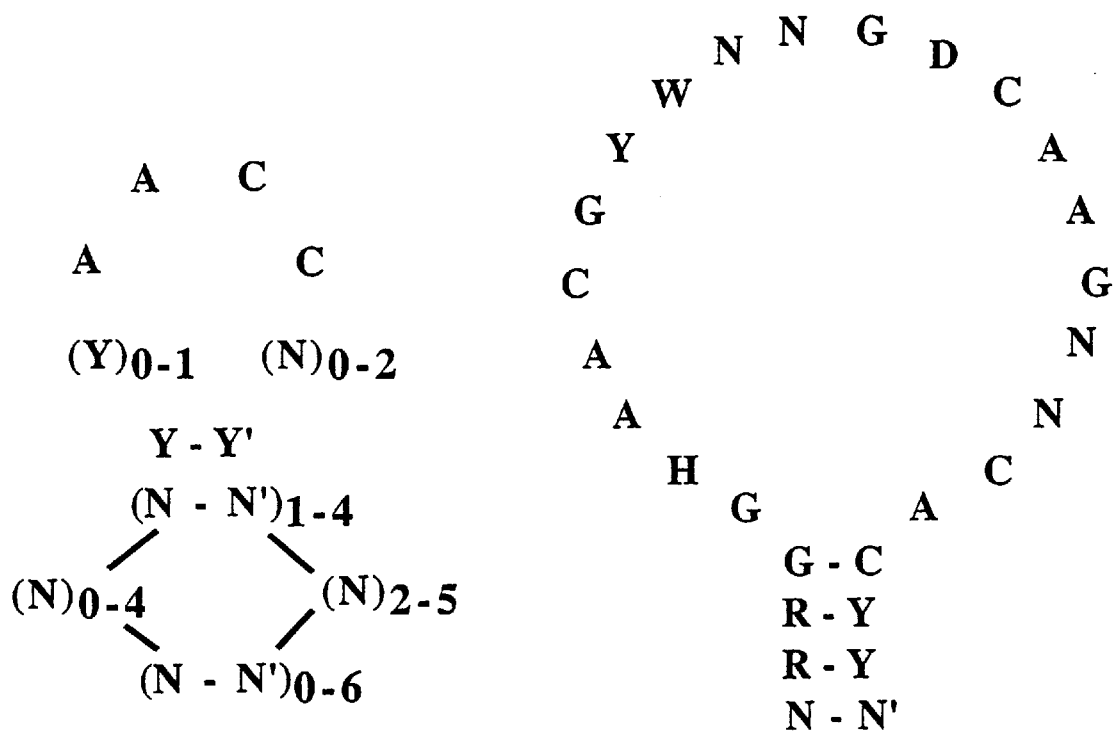
FIG. 4 shows the consensus structures for bFGF Family 1 and Family 2 ligands. Y=C or U; R=A or G; W=A or U; H=A, U, or C; D=A, G, or U; N=any base. Complementary bases are primed. Symbols in parenthesis indicate a variable number of bases or base pairs at that position ranging within limits given in the subscript.

A review of the proposed structural formations shown in FIG. 4 for the Family 1 and 2 unmodified ligands to bFGF and FIG. 7 for the Class 1 and 2 unmodified ligands to thrombin shows that sequences that have little or no primary sequence homology may still have substantially the same ability to bind bFGF or thrombin, respectively. It can be assumed that the disparate sequences in FIG. 4 have similar structures that give rise to the ability to bind to bFGF, and that each of the Family 1 and Family 2 sequence ligands are able to assume structures that appear very similar to the binding site of bFGF even though they may not bind the same site. Likewise, it can be assumed that the disparate sequences depicted in FIG. 7 have a common structure that gives rise to the ability to bind to thrombin, and that each of the Class 1 and Class 2 sequence ligands are able to assume structures that appear very similar to the binding site of thrombin even though they may not bind the same site. For these reasons, the present invention also includes RNA ligands that have substantially the same structure as the ligands presented herein and that have substantially the same ability to bind bFGF and thrombin as the RNA ligands shown in Tables II and III and Tables XII and XIII, respectively. "Substantially the same structure" includes all RNA ligands having the common structural elements of the sequences given in Tables II, III, XII and XIII.

As stated above, this invention also includes the specific 2'-NH$_2$-modified nucleic acid ligands to bFGF shown in Table VIII. These ligands were identified by the SELEX method utilizing a candidate mixture of RNAs wherein all pyrimidines were 2'-deoxy-2'-NH$_2$. All purines utilized in these experiments were unmodified, or 2'-OH. More specifically, this invention includes nucleic acid sequences that are substantially homologous to and that have substantially the same ability to bind bFGF as the specific nucleic acid ligands shown in Table VIII.

This invention also covers the specific DNA nucleic acid ligands to bFGF (Tables XXI and XXII) and thrombin (Tables XV and XVI). Also included are DNA sequences that are substantially homologous to and that have substantially the same ability to bind thrombin and bFGF as the specific sequences given in Tables XV, XVI, XXI and XXII. Also included are DNA ligands that have substantially the same structure as the ligands presented in Tables XV, XVI, XXI and XXII and that have substantially the same ability to bind thrombin and bFGF, respectively.

This invention also includes the ligands described above, wherein certain chemical modifications have been made in order to increase the in vivo stability of the ligand, enhance or mediate the delivery of the ligand, or reduce the clearance rate from the body. Examples of such modifications include chemical substitutions at the ribose and/or phosphate and/or base positions of a given RNA sequence. See, e.g., Cook et al. PCT Application WO 92/03568; U.S. Pat. No. 5,118,672 of Schinazi et al.; Hobbs et al. (1973) Biochem. 12:5138; Guschlbauer et al. (1977) Nucleic Acids Res. 4:1933; Shibahara et al. (1987) Nucleic Acids Res. 15:4403; Pieken et al. (1991) Science 253:314, each of which is specifically incorporated herein by reference. Such modifications may be made post-SELEX (modification of previously identified unmodified ligands) or by incorporation into the SELEX process as described below.

Two SELEX experiments were conducted to select unmodified RNA ligands to bFGF (Examples 1 and 2). These experiments yielded two sequence families of high-affinity nucleic acid ligands to bFGF Family 1 and Family 2 (Tables II and III), as well as single sequences ("other sequences") (Table IV) and repeat sequences (Table V). A review of the two sequence families (Tables II and III) shows that sequences that have little or no primary sequence homology may still have substantially the same ability to bind bFGF. It appears that the disparate sequences may have a common structure that gives rise to the ability to bind to bFGF, and that each of the sequence Family 1 and 2 ligands are able to assume structures that appear very similar to the binding site of bFGF even though they may not bind the same site. High-affinity nucleic acid ligands selected in the presence of heparin (Experiment B) exhibited the consensus sequence of Family 2. These ligands bind a bFGF protein in which a conformation change has been induced by heparin.

The high-affinity nucleic acid ligands to bFGF of the present invention may also have various properties, including the ability to inhibit the biological activity of bFGF. Representative ligands from Family 1 and 2 (Tables II and III) were found to inhibit binding of bFGF to both low-and high-affinity cell-surface receptors (Example 5). These nucleic acid ligands may be useful as specific and potent neutralizers of bFGF activity in vivo.

Two SELEX experiments, to select ligands to bFGF, were conducted with RNA candidate mixtures wherein all pyrimidine moieties were 2'-deoxy-2'-NH$_2$-pyrimidines (Example 4, experiments A and B). These experiments yielded the sequences shown in Table VIII. Sequence families 1A, 1B, 1C, 2 and 3 were identified, as well as, four families containing two sequences each ("two-member families"), single sequences ("other sequences"), and sequences binding nitrocellulose ("nitrocellulose-binding family"). The nitrocellulose-binding ligands have an increased affinity to nitrocellulose as well as an increased affinity to bFGF. The high affinity of identified 2'-NH$_2$ ligands for bFGF is shown in Table IX and FIG. 5. 2'-NH$_2$-modified RNA ligands able to inhibit the in vitro activity of bFGF were identified (FIG. 6). These ligands were shown to inhibit the biological activity of bFGF in vivo (Example 6).

The effect of the modified 2'-NH$_2$ RNA ligands on endothelial cell motility was examined in Example 7. Ligand 21A-ts (SEQ ID NO:444), a chemically synthesized analogue of ligand 21A-t (SEQ ID NO:186), was found to inhibit bovine aortic endothelial (BAE) cell migration in a dose dependent manner at concentrations greater than 50 nM. The total amount of motility that could be inhibited by 21A-ts at high concentrations was comparable in all experiments to the effect of 100 $\mu$g/ml neutralizing bFGF antibody.

Example 8 describes the evolution of high affinity DNA ligands to bFGF using SELEX (see Table XXI). Candidate mixtures with 30 and 40 variable nucleotide regions were employed in three experiments starting with three separate sets of snthetic DNA oligonucleotide templates and primers (see Table XIX). A significant improvement in affinity of DNA ligands to bFGF was observed in each of the three experiments after ten rounds of selection (see Table XX in which the results for Experiment 3 are depicted). Five distinct families were identified based on 40% or better overlap in sequence homology (Table XXI). A number of sequences with no homology to members of the five families were also present and are listed in Table XXI as orphans.

A majority of the ligands isolated from Experiments 1 and 3 were screened for their ability to bind bFGF and high-affinity ligands for bFGF were found in five sequence families (see Example 8 and Table XXI (*)). The Kds of the isolates tested for affinity to bFGF are listed in Table XXII. Removal of nucleotides non-essential for binding was performed on five of the ligands with the highest affinity for bFGF, Kds less than 1 nM (Table XXII, Truncations).

The five truncated molecules were tested for their ability to inhibit binding of bGFG to its low- and high-affinity cell-surface receptors. All five ligands show inhibition in the nanamolar range. Truncated ligand M225t3 (SEQ ID NO:364) was also tested for its specificity. It was found that the affinity of M225t3 for vascular endothelial growth factor and human chorionic gonadotropin, two heparin-binding proteins, was relatively weak (Kd>0.2 $\mu$M).

To determine whether enhanced circulation time could be obtained by conjugating the bFGF ligand to a high molecular weight species, a M225t3 DNA ligand was synthesized and coupled with an N-hydroxysuccinimidyl active ester of PEG 3400 (Example 9). The PEG modified M225t3 was shown to bind bFGF with a similar affinity as the non-modified ligand.

The nucleic acid ligands and nucleic acid ligand solutions to bFGF described herein are useful as pharmaceuticals, and as part of gene therapy treatments. Example 6 shows the ability of 2'-NH$_2$-modified RNA ligands to inhibit the in vivo biological activity of bFGF. Further, the nucleic acid ligands to bFGF described herein may be used beneficially for diagnostic purposes.

The SELEX process for identifying ligands to a target was performed using human thrombin as the target, and a candidate mixture containing 76 nucleotide RNAs with a 30 nucleotide region of unmodified randomized sequences (Example 10). Following twelve rounds of SELEX, a number of the selected ligands were sequenced, to reveal the existence of two groups of sequences that had common elements of primary sequence (Example 11).

A dramatic shift in binding of the RNA population was observed after 12 rounds of SELEX, when compared to the bulk 30N RNA. Sequencing of bulk RNA after 12 rounds also showed a non-random sequence profile. The RNA was reverse transcribed, amplified, cloned and the sequences of 28 individual molecules were determined (Table XII). Each sequence is divided into 3 blocks from left to right: 1) the 5' fixed region, 2) the 30N variable region, and 3) the 3' fixed region. Based on primary sequence homology, 22 of the RNAs were grouped as Class I and 6 RNAs were grouped as Class II. Of the 22 sequences in Class I, 16 (8 of which were identical) contained an identical sequence motif GGAUCGAAG(N)$_2$AGUAGGC (SEQ ID NO:190), whereas the remaining 6 contained 1 or 2 nucleotide changes in the defined region or some variation in N=2 to N=5. This conserved motif varied in its position within the 30N region. In Class II, 3 of the 6 RNAs were identical and all of them contained the conserved motif GCGGCUUUGGGCGC-CGUGCUU (SEQ ID NO:191), beginning at the 3rd nucleotide from the end of the 5' fixed region.

Three sequence variant RNA ligands from Class I (6 (SEQ ID NO:192), 16 (SEQ ID NO:198), and 18 (SEQ ID NO:199)) and one (27 (SEQ ID NO:209)) from Class II, identified by the order they were sequenced, were used for individual binding analysis. Class I RNAs were exemplified by clone 16 with a Kd of approximately 30 nM and the Kd for the Class II RNA clone 27 was approximately 60 nM.

In order to identify the minimal sequence requirements for specific high affinity binding of the 76 nucleotide RNA which includes the variable 30N region flanked by 5' and 3' fixed sequence, 5' and 3' boundary experiments were performed (Example 12). For 5' boundary experiments the RNAs were 3' end labeled and hydrolyzed to give a pool of RNAs with varying 5' ends. For the 3' boundary experiments, the RNAs were 5' end-labeled and hydrolyzed to give a pool of RNAs with varying 3' ends. Minimal RNA sequence requirements were determined following RNA protein binding to nitrocellulose filters and identification of labeled RNA by gel electrophoresis (Example 12).

3' boundary experiments gave the boundaries for each of the 4 sequences shown in Table XIII. These boundaries were consistent at all protein concentrations. 5' boundary experiments gave the boundaries shown in Table XIII plus or minus 1 nucleotide, except for RNA 16 which gave a greater boundary with lower protein concentrations. Based on these boundary experiments, possible secondary structures of the thrombin ligands are shown in FIG. 7.

Figure 8A:
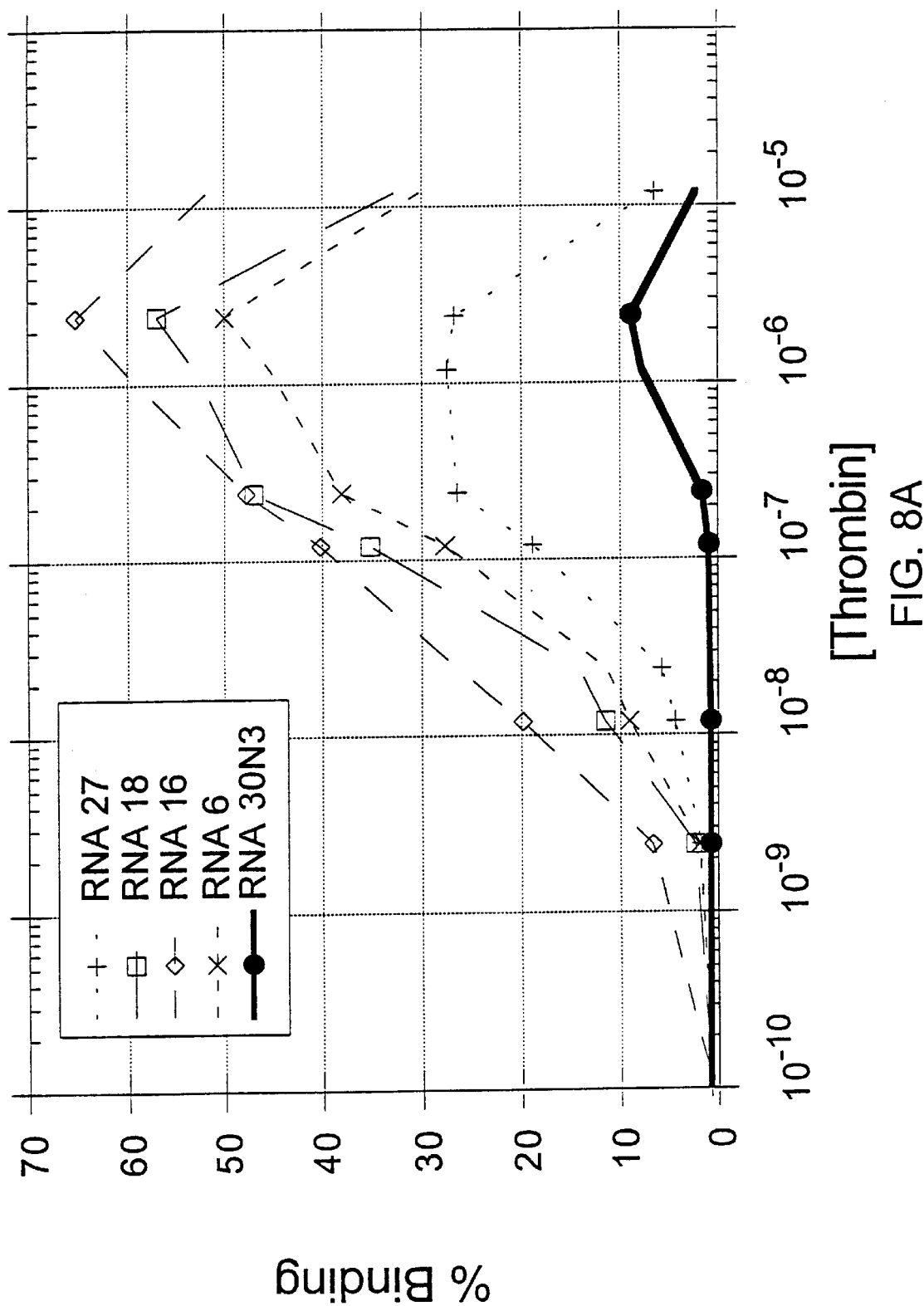
FIGS. 8A and 8B depicts binding curves for various thrombin ligands.
Figure 8B:
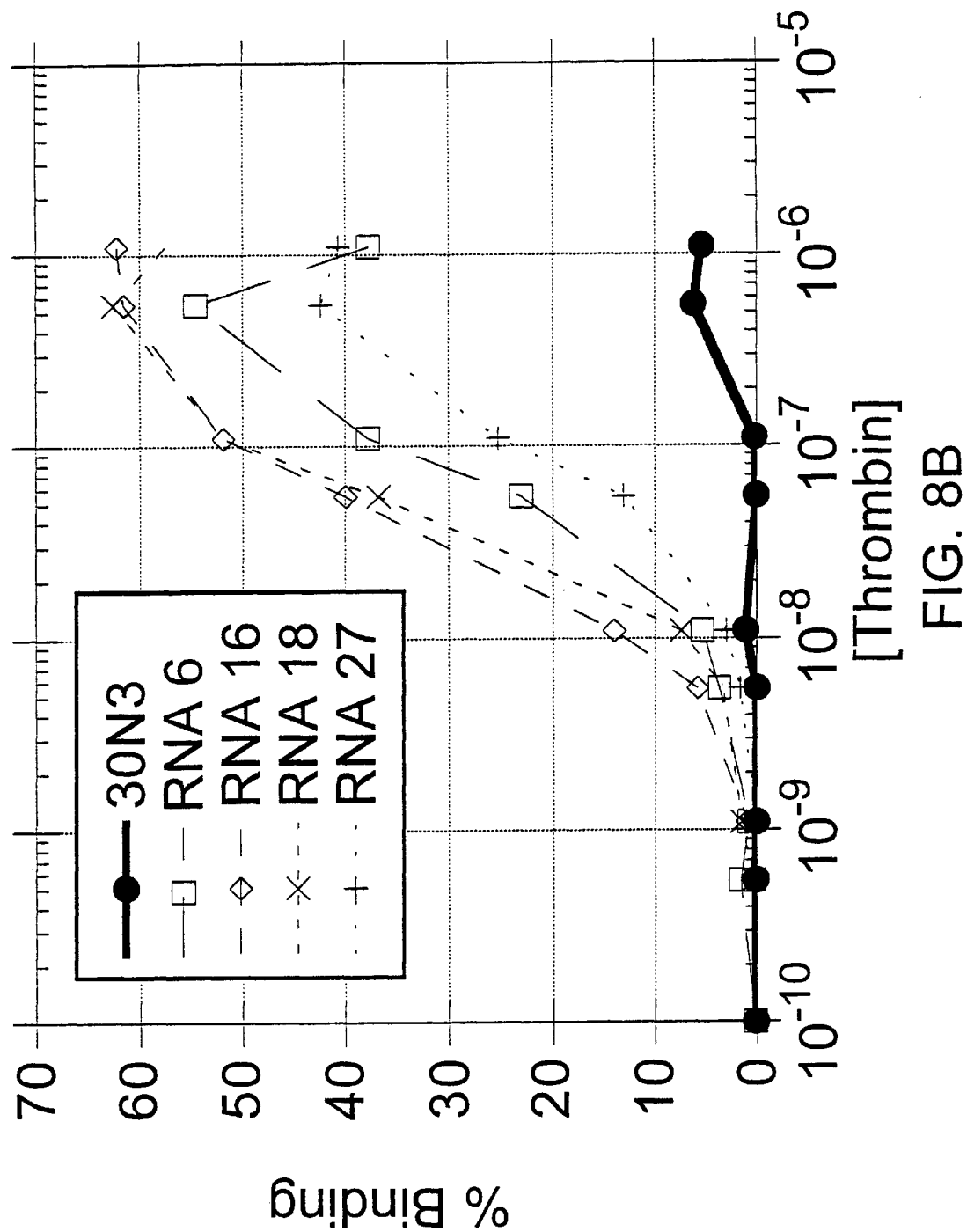
Figure 8C:
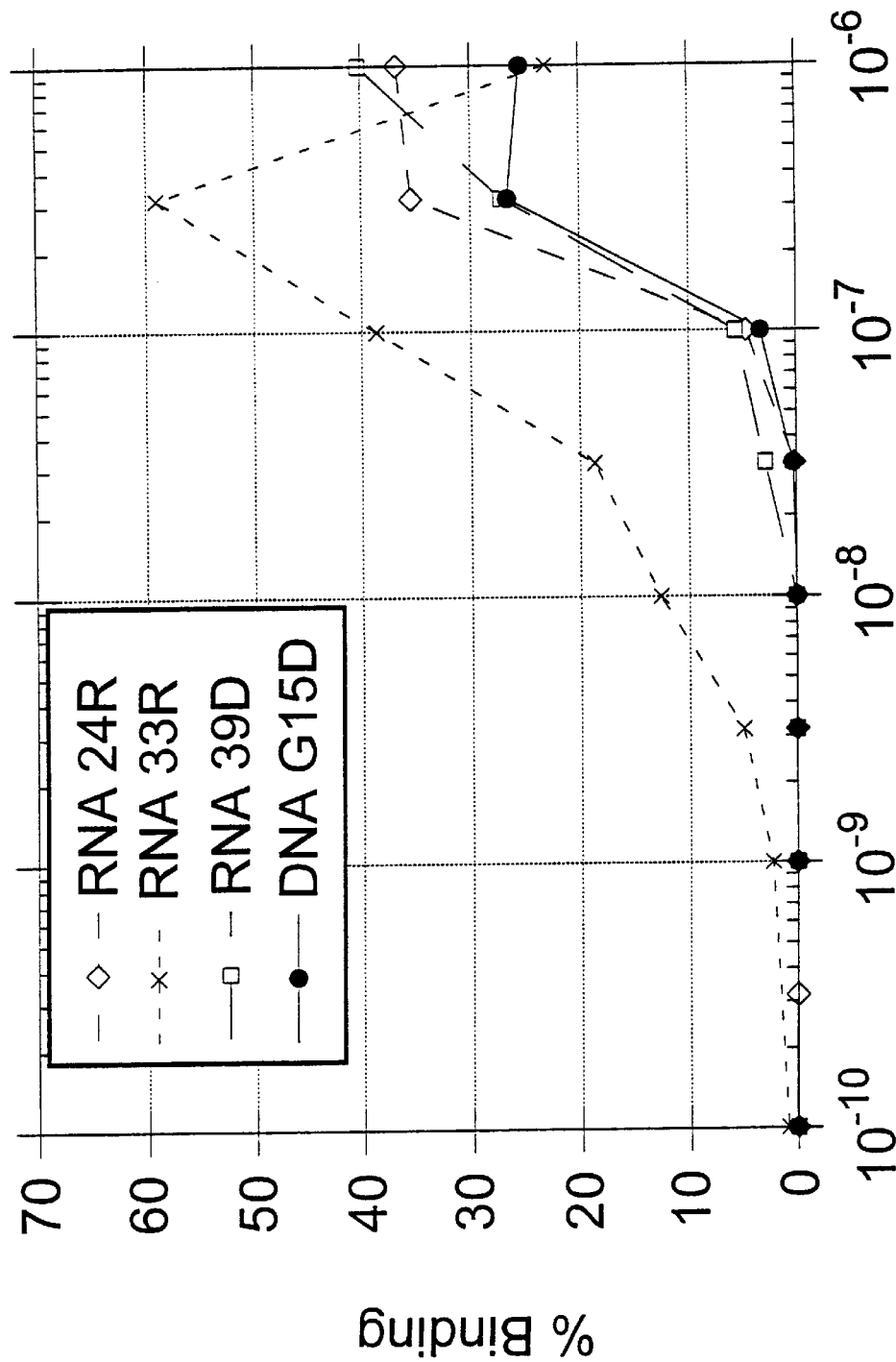
In FIG. 8C, binding of the 15mer ssDNA 5'-GGTTGGTGTGGTTGG-3' (G15D) (SEQ ID NO:189), the Class I clone 16 hairpin structures (24R, 39D) (SEQ ID NO:212) and the Class II clone 27 hairpin structure (33R) (SEQ ID NO:214) (see FIG. 7 and Table XIII) are shown under identical conditions as in FIG. 8B. In the case of the RNA hairpin structures, R denotes RNA synthesis and D denotes transcription from a DNA template.

RNAs corresponding to the smallest and largest hairpin of Class I clone 16 (SEQ ID NO:212) (24 and 39 nucleotides) and the hairpin of Class II clone 27 (SEQ ID NO:214) (33 nucleotides) were synthesized or transcribed for binding analysis (see FIG. 7 and Example 13). Results show that the RNA 27 hairpin binds with affinity (Kd of about 60 nM) equal to that of the entire 72 nucleotide transcript with fixed and variable region (compare RNA 27 in FIG. 8A with RNA 33R in FIG. 8C). The Kds for Class I clone 16 RNA hairpins on the other hand increased an order of magnitude from 30 nM to 200 nM.

Figure 9A:
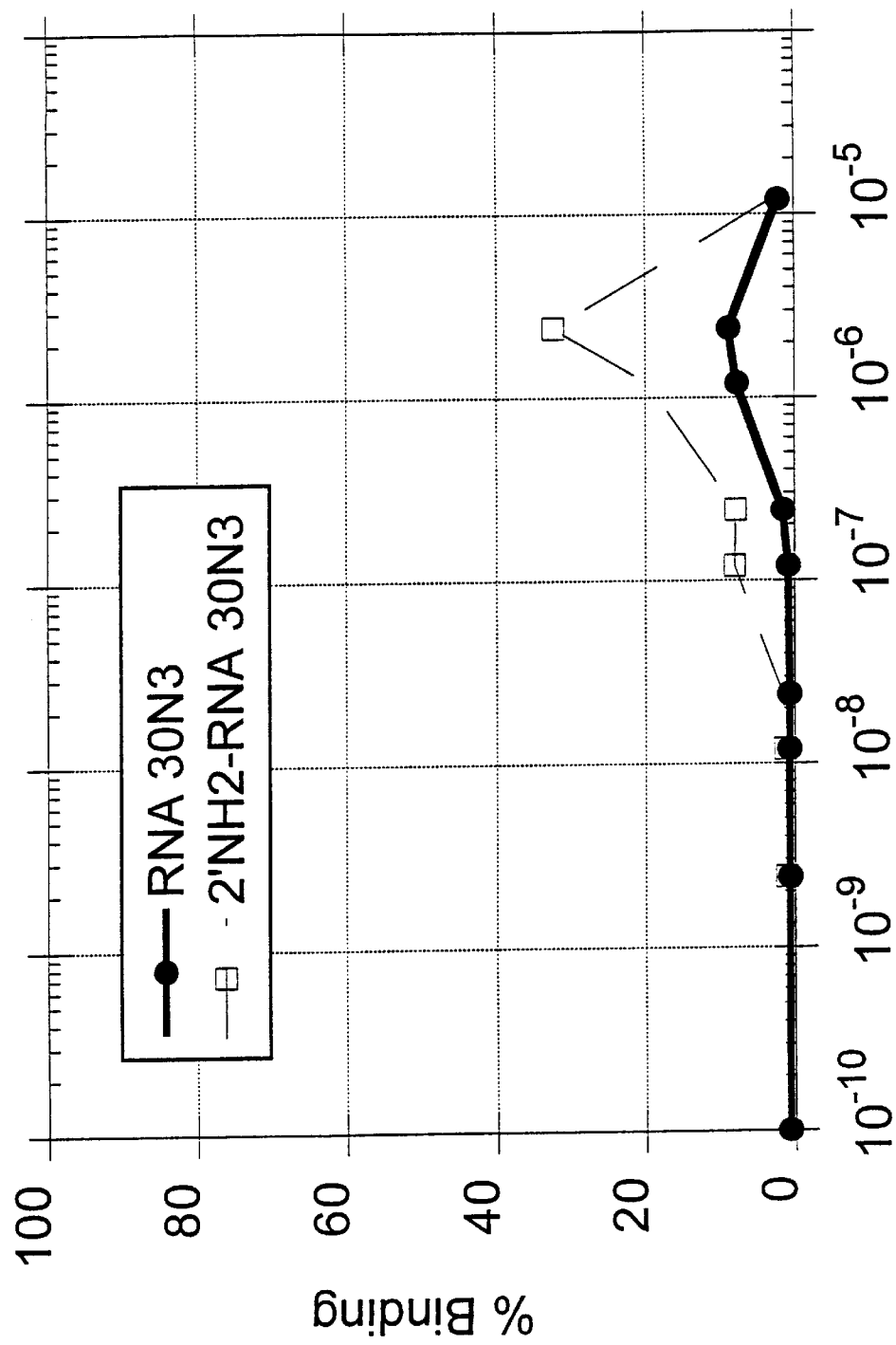
Figure 9C:
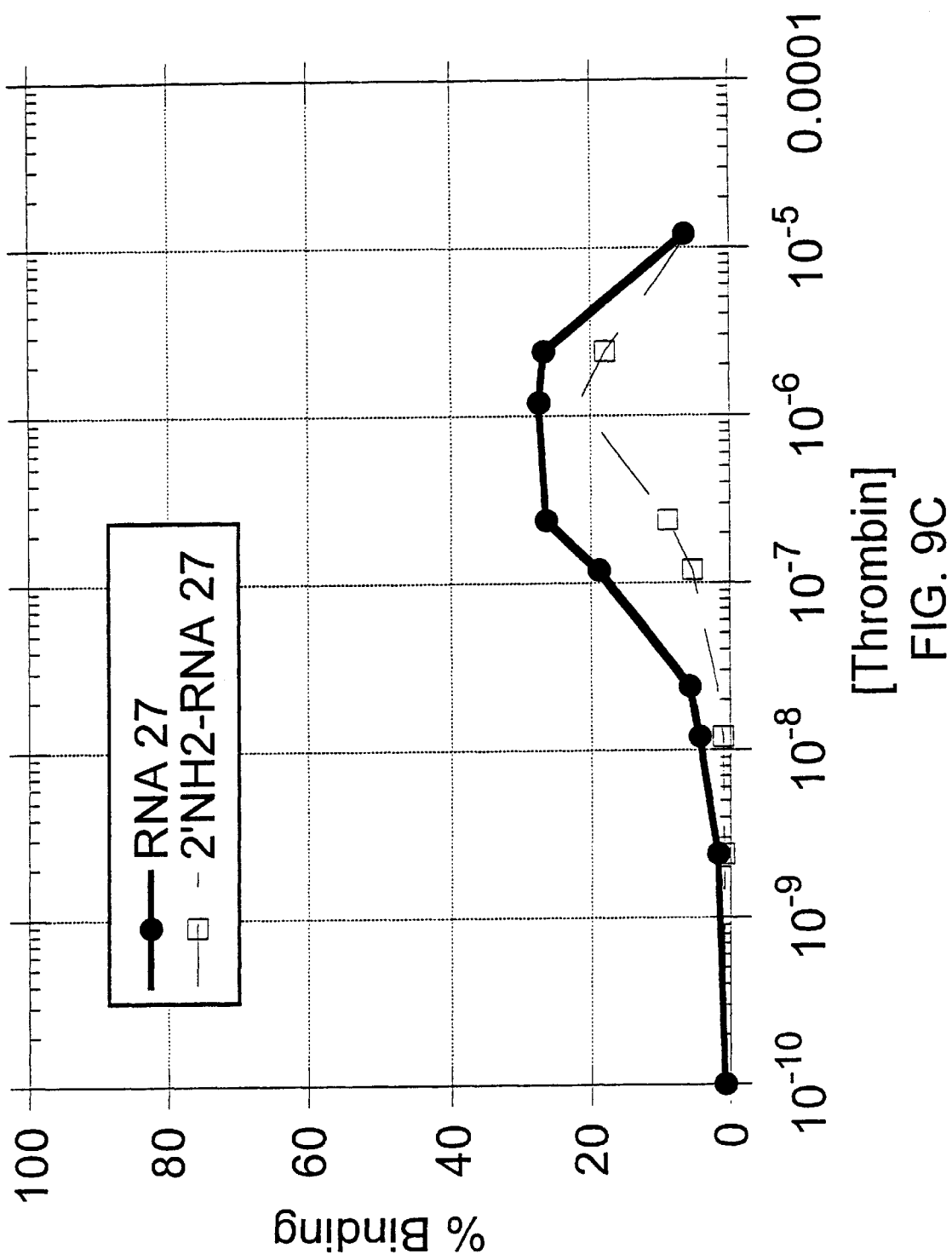
FIG. 9C depicts the binding comparison of Class II RNA 27 (SEQ ID NO:209) and 2'-NH$_2$ modified RNA 27 are shown.

Modifications in the 2NH$_2$-ribose of pyrimidine residues of RNA molecules has been shown to increase stability of RNA (resistant to degradation by RNase) in serum by at least 1000 fold. 2'-NH$_2$ modified RNAs were prepared in Example 14. Binding experiments (Example 14) with the 2'-NH$_2$-CTP/UTP modified RNAs of Class I and Class II showed a significant drop in binding when compared to the unmodified RNA (FIG. 9). Binding by the bulk 30N RNA, however, showed a slight increase in affinity when it was modified.

Figure 10A:
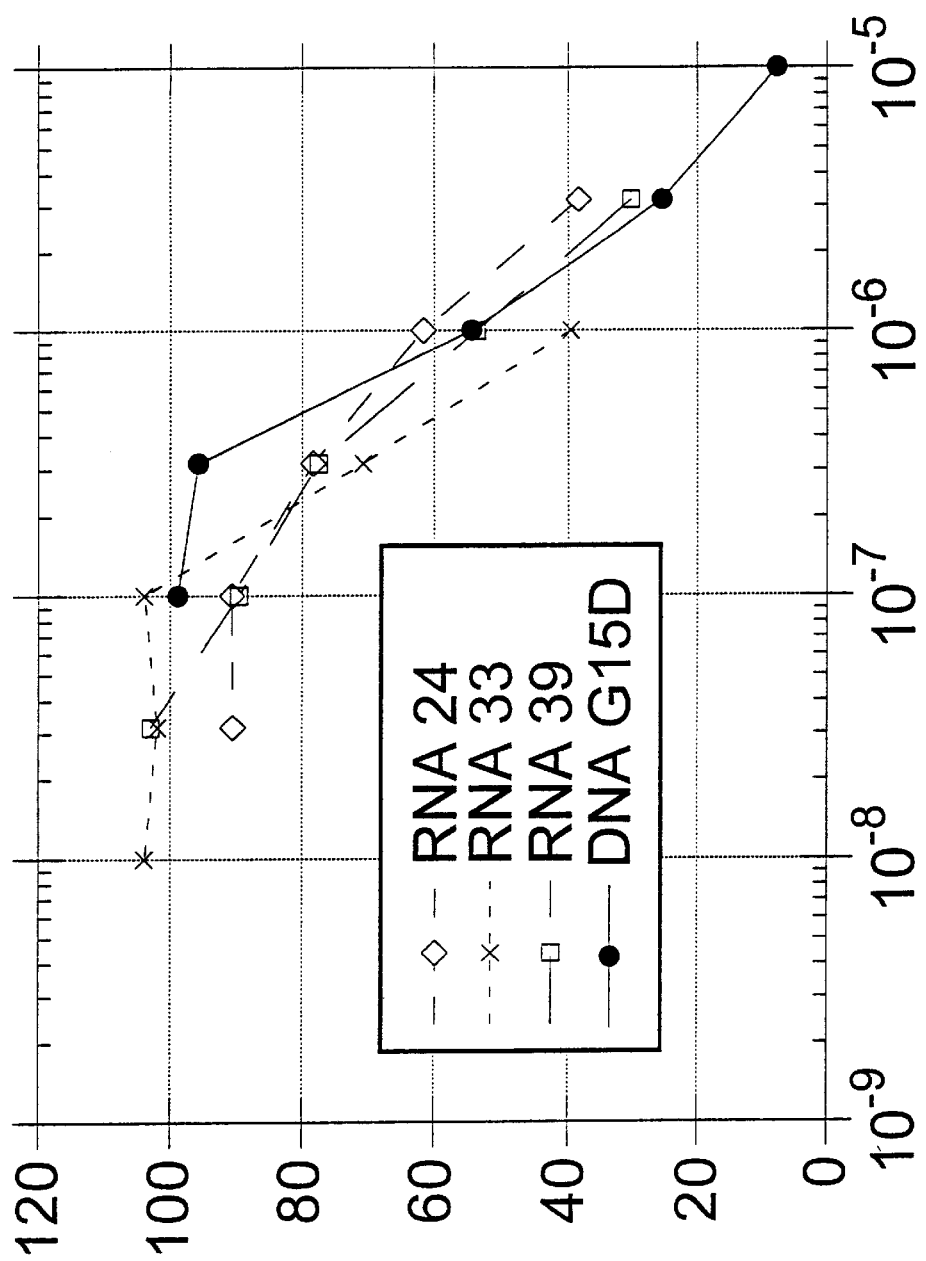

A ssDNA molecule with a 15 nucleotide consensus 5'-GGTTGGTGTGGTTGG-3'(G15D) (SEQ ID NO:189) has been shown to bind human thrombin and inhibit fibrin-clot formation in vitro (Bock et al. (1992) Nature 355:564–565). The results of competition experiments for binding thrombin between G15D and the RNA hairpin ligands of this invention are shown in FIG. 10 (see Example 15). In the first of these experiments (Experiment A) a $^{32}$P-labeled G15D was used as the tracer with increasing concentrations of unlabeled RNA or unlabeled G15D. As expected, when the G15D was used to compete for its own binding, binding of labeled DNA was reduced to 50% at equimolar concentrations (1 $\mu$M) of labeled and unlabeled competitor DNA. Both the Class I clone 16 synthetic RNAs 24 and 39, and the Class II clone 27 synthetic RNA 33 were able to compete for binding of G15D at this concentration. In the second experiment (Experiment B) the higher affinity Class II hairpin RNA 33 (Kd≈60 nM) was $^{32}$P-labelled and used as the tracer with increasing concentrations of unlabelled RNA or unlabelled G15D DNA (Kd≈200 nM). In these experiments, the G15D was able to compete effectively with RNA 33 at higher concentrations than the RNA 33 competes itself (shift of binding to the right), which is what is expected when competing with a ligand with 3–4 fold higher affinity. The Class II hairpin RNA 33 (Kd≈60 nM) was competed only weakly by the class I hairpin RNA 24 (Kd≈200 nM), suggesting that while there may be some overlap, the RNAs of these two classes may bind with high affinity to different yet adjacent or overlapping sites. Because both of these RNAs can compete for G15D binding, this DNA 15mer probably binds in the region of overlap between the Class I and Class II hairpins.

The ability of thrombin to cleave the peptidyl chromogenic substrate S2238 (H-D-Phe-Pip-Arg-pNitroaniline) (H-D-Phe-Pip-Arg-pNA) (Kabi Pharmacia) was measured in the presence and absence of the RNA ligands of this invention (Example 16). The hydrolysis by thrombin of the chromogenic substrate S-2238 (H-D-Phe-Pip-Arg-pNitroaniline) at the indicated thrombin and RNA concentration was measured photometrically at 405 nm (Table XIV). There was no inhibitory effect of RNA on this cleavage reaction at $10^{-8}$ M thrombin and $10^{-8}$ M RNA, $10^{-9}$ M thrombin and $10^{-8}$ M RNA or at $10^{-8}$ M thrombin and $10^{-7}$ M RNA. These results suggest that the RNA ligands do not bind in the catalytic site of the enzyme.

The ability of thrombin to catalyze clot formation by cleavage of fibrinogen to fibrin was measured in the presence and absence of RNA (Example 17). The conversion of fibrinogen to fibrin and resulting clot formation was measured by the tilt test in the presence and absence of the RNA ligand inhibitors described. When RNA was present at a concentration equal to the Kd (30 nM for Class I RNAs and 60 nM for Class II RNAs), which was in 5 to 10-fold excess of thrombin, clotting time was increased by 1.5-fold (Table XIV).

Figure 11A:
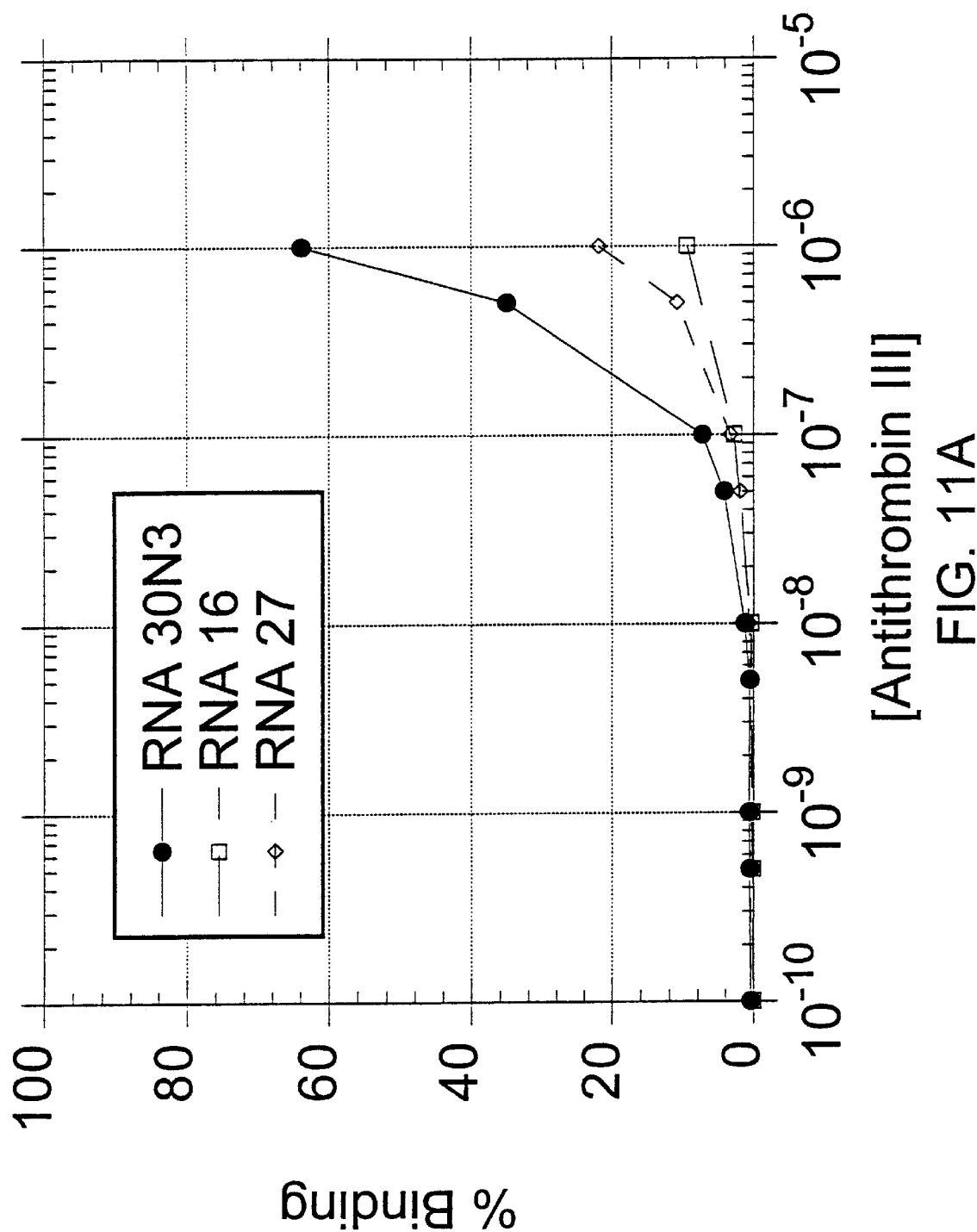
FIGS. 11A and 11B show specificity of binding for thrombin ligands. Class I RNA 16 (SEQ ID NO:198), Class II RNA 27 (SEQ ID NO:209), and bulk 30N3 RNA were chosen for binding analysis with human antithrombin III (Sigma) (FIG. 11A) and human prothrombin (Sigma) (FIG. 11B).
Figure 11B:
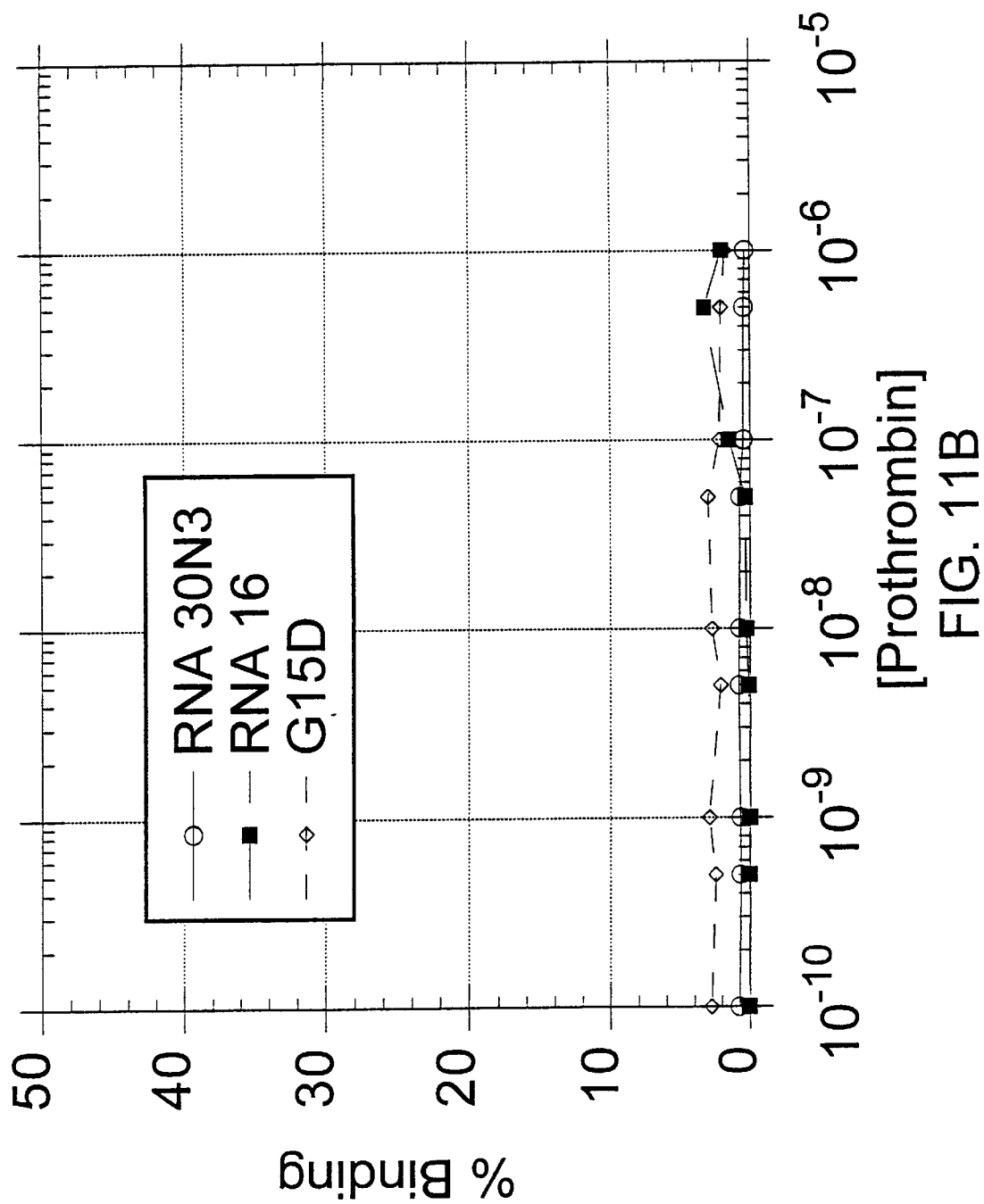

Representative ligands from Class I and Class II showed that these ligands had low affinity for ATIII at concentrations as high as 1 μM (Example 18, FIG. 11A). These ligands showed reduced affinity when compared with the bulk 30N3 RNA suggesting that there has been selection against non-specific binding. This is of particular importance because ATIII is an abundant plasma protein with high affinity for heparin, a polyanionic macromolecule. These results show that the evolution of a discreet structure present in the Class I and Class II RNAs is specific for thrombin binding and, despite its polyanionic composition, does not bind to a high affinity heparin binding protein. It is also important to note that these thrombin specific RNA ligands have no affinity for prothrombin (Example 18, FIG. 11B), the inactive biochemical precursor to active thrombin, which circulates at high levels in the plasma (≈1 μM).

Example 19 (Table XV) below describes the evolution of high affinity DNA ligands to thrombin utilizing SELEX. Candidate mixtures with 30 and 60 variable nucleotide regions were employed in separate experiments. The binding constants of several of the ligands to thrombin were obtained, and one of the ligands 60-18(38) (SEQ ID NO:279) was shown to inhibit coagulation by thrombin (Table XVI).

The nucleic acid ligands and nucleic acid ligand solutions to thrombin described herein are useful as pharmaceuticals and as part of gene therapy treatments. The ligands can also be useful for diagnostic purposes.

The concepts of vascular injury and thrombosis are important in the understanding of the pathogenesis of various vascular diseases, including the initiation and progression of atherosclerosis, the acute coronary syndromes, vein graft disease, and restenosis following coronary angioplasty.

The high-affinity thrombin binding RNA ligands of this invention may be expected to have various properties. These characteristics can be thought about within the context of the hirudin peptide inhibitors and the current understanding of thrombin structure and binding. Within this context and not being limited by theory, it is most likely that the RNA ligands are binding the highly basic anionic exosite. It is also likely that the RNA is not binding the catalytic site which has high specificity for the cationic arginine residue. One would expect the RNA ligands to behave in the same manner as the C-terminal hirudin peptides. As such, they would not strongly inhibit small peptidyl substrates, but would inhibit fibrinogen-clotting, protein C activation, platelet activation, and endothelial cell activation. Given that within the anionic exosite the fibrinogen-clotting and TM-binding activities are separable, it is possible that different high-affinity RNA ligands may inhibit these activities differentially. Moreover, one may select for one activity over another in order to generate a more potent anticoagulant than procoagulant.

EXAMPLE 1

Experimental Procedures

Materials. bFGF was obtained from Bachem California (molecular weight 18,000 Da, 154 amino acids). Tissue culture grade heparin (average molecular weight 16,000 Da) was purchased from Sigma. Low molecular weight heparin (5,000 Da) was from Calbiochem. All other chemicals were at least reagent grade and were purchased from commercial sources.

SELEX. Evolution of High Affinity Ligands to bFGF. Essential features of the SELEX protocol have been described in detail in the SELEX Applications and in previous papers (Tuerk & Gold (1990) Science 249:505; Tuerk et al. (1992a) Proc. Natl. Acad. Sci. USA 89:6988; Tuerk et al. (1992b) in Polymerase Chain Reaction (Ferre, F. Mullis, K., Gibbs, R. & Ross, A., eds.) Birkhauser, NY). The SELEX protocol may be performed in generally the same manner for unmodified RNA selection as for selection with 2'-deoxy-2'-NH$_2$ pyrimidines as described in Example 4 below. Briefly, DNA templates for in vitro transcription (that contain a region of thirty random positions flanked by constant sequence regions) and the corresponding PCR primers were synthesized chemically (Operon). The random region was generated by utilizing an equimolar mixture of the four nucleotides during oligonucleotide synthesis. The two constant regions were designed to contain PCR primer annealing sites, a primer annealing site for cDNA synthesis, T7 RNA polymerase promoter region, and restriction enzyme sites that allow cloning into vectors (See Table I).

An initial pool of RNA molecules was prepared by in vitro transcription of about 200 picomoles (pmol) ($10^{14}$ molecules) of the double stranded DNA template utilizing T7 RNA polymerase (New England Biolabs). Transcription mixtures consisted of 100–300 nM template, 5 units/μl T7 RNA polymerase, 40 mM Tris-Cl buffer (pH 8.0) containing 12 mM MgCl$_2$, 5 mM DTT, 1 mM spermidine, 0.002% Triton X-100, and 4% PEG. Transcription mixtures were incubated at 37° C. for 2–3 hours. These conditions typically resulted in transcriptional amplification of 10- to 100-fold.

Selections for high affinity RNA ligands to bFGF were done by incubating bFGF (10–100 pmol) with RNA (90–300 pmol) for 10 minutes at 37° C. in 50 μl of phosphate buffered saline (PBS) (10.1 mM $Na_2HPO_4$, 1.8 mM $KH_2PO_4$, 137 mM NaCl, 2.7 mM KCl, pH 7.4), then separating the protein-RNA complexes from the unbound species by nitrocellulose filter partitioning (Tuerk & Gold (1990) Science 249:505). The selected RNA (which typically amounts to 0.3–8% of the total input RNA) was then extracted from the filters and reverse transcribed into cDNA by avian myeloblastosis virus reverse transcriptase (AMV RT, Life Sciences). Reverse transcriptions were done at 48° C. (30 minutes) in 50 mM Tris buffer (pH 8.3), 60 mM NaCl, 6 mM $Mg(OAc)_2$, 10 mM DTT, and 1 unit/µl AMV RT. Amplification of the cDNA by PCR under standard conditions yielded sufficient amounts of double-stranded DNA for the next round of in vitro transcription.

Nitrocellulose Filter Binding Assay

Oligonucleotides bound to proteins can be effectively separated from the unbound species by filtration through nitrocellulose membrane filters (Yarus & Berg (1970) Anal. Biochem. 35:450; Lowary & Uhlenbeck (1987) Nucleic Acids Res. 15:10483; Tuerk & Gold (1990) Science 249:505). Nitrocellulose filters (Millipore, 0.45 µm pore size, type HA) were secured on a filter manifold and washed with 4–10 ml of buffer. Following incubations of $^{32}$P-labeled RNA with serial dilutions of the protein (5–10 min) at 37° C. in buffer (PBS) containing 0.01% human serum albumin (HSA), the solutions were applied to the filters under gentle vacuum in 45 µl aliquots and washed with 5 ml of PBS. The filters were then dried under an infrared lamp and counted in a scintillation counter.

Cloning and Sequencing. Individual members of the enriched pools were cloned into pUC18 vector and sequenced as described (Schneider et al. (1992) J. Mol. Biol. 228:862–869; Tuerk & Gold (1990) supra).

EXAMPLE 2

Selex Experiments Targeting bFGF

Following the procedures described in Example 1 above, two SELEX experiments (Experiments A and B) targeting bFGF were initiated with separate pools of randomized unmodified RNA, each pool consisting of approximately $10^{14}$ molecules. The constant sequence regions that flank the randomized region, along with the corresponding primers, were different in each experiment. The two template/primer combinations used are shown in Table I.

Selections were conducted in PBS at 37° C. The selection conducted in Experiment B was done in the presence of heparin (Sigma, molecular weight 5,000=32,000 Da, average molecular weight 16,000 Da) in the selection buffer at the molar ratio of 1/100 (heparin/bFGF). Heparin competes for binding of randomized RNA to bFGF. The amount of heparin used significantly reduced, but did not eliminate RNA binding to bFGF (data not shown). The rationale for using heparin was two-fold. First, heparin is known to induce a small conformational change in the protein and also stabilizes bFGF against thermal denaturation. Second, the apparent competitive nature of binding of heparin with randomized RNA to bFGF was expected to either increase the stringency of selection for the heparin binding site or direct the binding of RNA ligands to alternative site(s).

Significant improvement in affinity of RNA ligands to bFGF was observed in Experiment A after ten rounds, and in Experiment B after thirteen rounds. Sequencing of these enriched pools of RNA ligands revealed a definite departure from randomness which indicated that the number of different molecules remaining in the pool was substantially reduced. Individual members of the enriched pools were then cloned into pUC18 vector and sequenced as described in Example 1.

49 clones were sequenced from Experiment A, and 37 clones from Experiment B. From the total of 86 sequences, 71 were unique. Two distinct families could be identified based on overlapping regions of sequence homology (Tables II and III, XVII and XVIII). A number of sequences with no obvious homology to members of either of the two families were also present, as expected (Irvine et al. (1991) J. Mol. Biol. 222:739), and are shown in Table IV.

The consensus sequence from Family 1 ligands (Table II) is defined by a contiguous stretch of 9 bases, CUAACCAGG (SEQ ID NO:7). This suggests a minimal structure consisting of a 4–5 nucleotide loop that includes the strongly conserved AACC sequence and a bulged stem (FIG. 4 and Table VI). The consensus sequence for Family 2 ligands (Table III) is more extended and contains less conserved regions, RRGGHAACGYWNNGDCAAGNNCACYY (SEQ ID NO:23). Here, most of the strongly conserved positions are accommodated in a larger (19–21 nucleotide) loop (FIG. 4 and Table VII). Additional structure within the loop is possible.

The existence of two distinct sequence families in the enriched pools of RNA suggest that there are two convergent solutions for high-affinity binding to bFGF. SELEX Experiment A contributed members to both sequence families (Table II). All of the sequences from the SELEX Experiment B (selected in the presence of heparin), on the other hand, belong either to Family 2 (Table III) or to the "other sequences" family (Table IV), but none were found in Family 1. This is surprising in view of the fact that bFGF was present in a molar excess of 100-fold over heparin during selections. The effective molar excess of bFGF over heparin, however, was probably much smaller. Average molecular weight of heparin used in selections was 16,000 Da. Since each sugar unit weighs 320 Da and at least eight sugar units are required for high-affinity binding to bFGF, six molecules of bFGF, on average, can bind to a molecule of heparin. This reduces the molar ratio of heparin to bFGF to 1:16. In practice, this amount of heparin is sufficient to reduce the observed affinity of the unselected RNA pool for bFGF by a factor of five (data not shown). The observed exclusion of an entire ligand family by the presence of a relatively small amount of heparin in the selection buffer may be a consequence of a conformational change in the protein induced by heparin. Because of the relative amounts of heparin and bFGF that were used in selections, this model may require that the heparin-induced conformation persist after the protein-heparin complex has dissociated, and that the lifetime of this conformer is long enough to permit equilibration with the RNA ligands.

Family 2 sequences are comprised of clones derived from both SELEX experiments. This suggests that the flanking constant regions typically play a relatively minor role in determining the affinity of these ligands and supports the premise that the consensus sequence in this family is the principal determinant of high-affinity binding to bFGF.

EXAMPLE 3

Determination of Binding Affinities for bFGF
Equilibrium Dissociation Constants.

In the simplest case, equilibrium binding of RNA to bFGF can be described by equation 1:

$$RNA \bullet bFGF \rightleftharpoons RNA + bFGF \qquad (1)$$

The fraction of bound RNA (q) is related to the concentration of free protein, [P] (equation 2):

$$q = f[P]/([P]+Kd) \qquad (2)$$

where Kd is the equilibrium dissociation constant and f reflects the efficiency of retention of the protein-RNA complexes on nitrocellulose filters. Mean value of f for bFGF was 0.82.

In order to eliminate higher order structures, all RNA solutions were heated to 90° C. in PBS for 2–3 minutes and cooled on ice prior to incubation with protein. Only single bands for all RNA clones were detected on non-denaturing polyacrylamide gels following this treatment.

Relative binding affinity of individual ligands to bFGF cannot be predicted from sequence information. Unique sequence clones were therefore screened for their ability to bind to bFGF by measuring the fraction of radiolabeled RNA bound to nitrocellulose filters following incubation with 4 and 40 nM protein. This screening method was sufficiently accurate to allow several clones to be identified that had dissociation constants in the nanomolar range. Binding of these select clones was then analyzed in more detail.

High-affinity RNA ligands for bFGF were found in both sequence families (Tables VI and VII). The affinity of clones that did not belong to either family was generally lower (data not shown).

The original, unselected RNA pools bound to bFGF with 300 nM (set A) and 560 nM (set B) affinities (FIG. 1). SELEX therefore allowed the isolation of ligands with at least 2 orders of magnitude better affinity for bFGF.

In order to address the question of specificity, a representative set of high-affinity ligands for bFGF (5A (SEQ ID NO:9) and 7A (SEQ ID NO:10) from Family 1; 12A (SEQ ID NO:25) and 26A (SEQ ID NO:26) from Fmily 2) were tested for binding to four other heparin-binding proteins. It was found that the affinity of these ligands for acidic FGF, thrombin, antithrombin III, and vascular endothelial growth factor was relatively weak (Kd>0.3 $\mu$M) (data not shown).

EXAMPLE 4

Modified 2'-NH$_2$ Pyrimidine RNA Ligands to bFGF

In order to generate ligands with improved stability in vivo, two SELEX experiments (A and B) targeting bFGF were initiated with separate pools of randomized RNA containing amino (NH$_2$) functionalities at the 2'-position of each pyrimidine. Starting ligand pools for the two experiments contained approximately 10$^{14}$ molecules (500 pmols) of modified RNA randomized at 30 (SELEX experiment A) and 50 (SELEX experiment B) contiguous positions. The starting RNAs and the corresponding PCR primers are defined in Table XI. Following twelve rounds of SELEX, the affinity of the modified RNA pools was improved by 1–2 orders of magnitude. Sequences corresponding to the evolved regions of modified RNA are shown in Table VIII. It is interesting to note that individual nucleotides occur at substantially different frequencies with guanine being conspicuously overrepresented (43%), adenine and uridine occurring at about equal frequencies (22% and 21%) and cytosine being underrepresented (14%).

Groups of ligand sequences with similar primary structure (families) have been aligned in Table VIII and their consensus sequences are shown below each set. Pairs of similar/related sequences, sequences that could not be included in any of the families ("other sequences") and sequences that correspond to ligands that bind additionally to nitrocellulose filters with high affinity have been shown in separate groups. The letter N in a sequence indicates an ambiguous position on a sequencing gel. An italicized letter N in a consensus sequence indicates a position that is not conserved (i.e., any nucleotide may be found at that position).

All unique ligands were screened for their binding affinities for bFGF by measuring the fraction of RNA bound to bFGF at two protein concentrations (5.0 and 0.5 nM bFGF). This affinity screening allowed identification of those ligands with highest affinity for bFGF. Binding of a group of these ligands was analyzed over a range of bFGF concentrations (FIG. 5) and their dissociation constants.(Kd's) were determined as described (Jellinek et al. (1993) Proc. Natl. Acad. Sci. USA 90:11227–11231) (Table IX). RNA concentrations were determined from their absorbance reading at 260 nM (and were typically <100 pM). Binding reactions were done at 37° C. in phosphate buffered saline containing 0.01% human serum albumin and 1 mM DTT.

The minimal sequence information required for high-affinity binding to bFGF was examined for several of the 2'-NH$_2$ modified ligands by deletion analyses as described (Tuerk et al. (1990) J. Mol. Biol. 213:749–761). Truncated ligands 21A-t (GGUGUGUGGAAGACAGCGGGUGGuuc (SEQ ID NO:186); the letter "t" is used to designate truncated sequences derived from the corresponding parent sequences; underlined G's are those guanine nucleotides added to improve the efficiency of transcription; lowercase letters are from the constant sequence region), 58A-t (GGACGGCGUGGUCCGAGGGUGGCGAGU) (SEQ ID NO:187) and 34B-t (GgaggacgaugcggAACGGGAGGUACGA GAGCGGGAGC) (SEQ ID NO:188) were synthesized enzymatically using T7 RNA polymerase from synthetic DNA templates and their binding affinity for bFGF was examined. Ligand 21A-t binds to bFGF in a biphasic manner with a dissociation constant of the higher affinity component (Kd1) of 0.1 nM, mole fraction of the higher affinity component ($\chi$1) of 0.5 and a dissociation constant of the lower affinity component (Kd2) of 270 nM (for interpretation of biphasic binding see Jellinek et al. (1993) Proc. Natl. Acad. Sci. USA 90:11227–11231). Binding of ligand 58A-t to bFGF is also biphasic (Kd1=1.8 nM, $\chi$1=0.5, Kd2=180 nM). Binding of ligand 34B-t is monophasic (Kd1=3 nM).

The ability to inhibit the binding of $^{125}$I-bFGF to high and low-affinity cell-surface receptors was examined (FIG. 6). Experiments were conducted as described in Moscatelli (1987) J. Cell. Physiol. 131:123 using confluent cultures of baby hamster kidney cells. Specific activity of bFGF was 915 cpm/fmol. Each data point represents the average of two experiments.

Figure 6B:
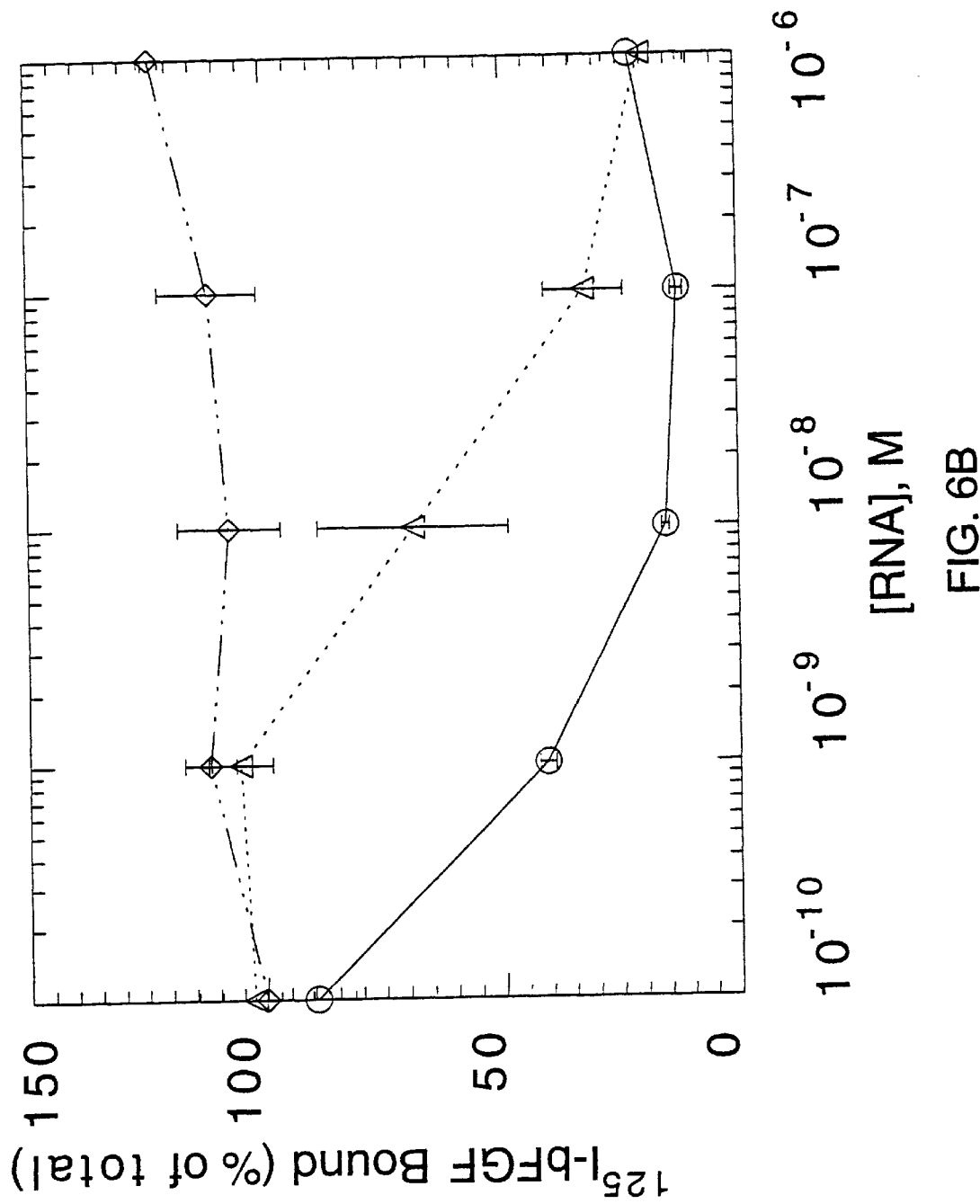

Several high-affinity ligands were found to inhibit binding of bFGF to its cell-surface receptors, with truncated versions of ligand 21A being the most effective inhibitors (FIG. 6B). Random RNA was ineffective in this concentration range (up to 1 $\mu$M).

EXAMPLE 5

RNA Ligand Inhibition of bFGF Receptor Binding

The same four high-affinity RNA ligands (5A (SEQ ID NO:9) and 7A (SEQ ID NO:10) from Family 1, 12A (SEQ ID NO:25) and 26A (SEQ ID NO:26) from Family 2) described in Example 3 were also tested for their ability to inhibit binding of bFGF to the low- and the high-affinity cell-surface receptors. Additionally, modified RNA ligands 21A (SEQ ID NO:104), 38B (SEQ ID NO:114) and Random RNAs were tested.

Receptor Binding Studies. bFGF was labeled with $^{125}$I by the Iodo-Gen (Pierce) procedure as described by Moscatelli (1987) J. Cell. Physiol. 131:123. Confluent baby hamster kidney (BHK) cells were washed extensively with PBS and then incubated for 2 hours at 4° C. with αMEM medium containing 10 ng/ml $^{125}$I-bFGF in PBS, 0.1% HSA, 1 unit/ml RNasein, and serial dilutions of high-affinity RNA. In a separate experiment it was established that the RNA is not significantly degraded under these conditions. The amount of $^{125}$I-bFGF bound to the low- and the high-affinity receptor sites was determined as described by Moscatelli (1987) supra.

Figure 2A:
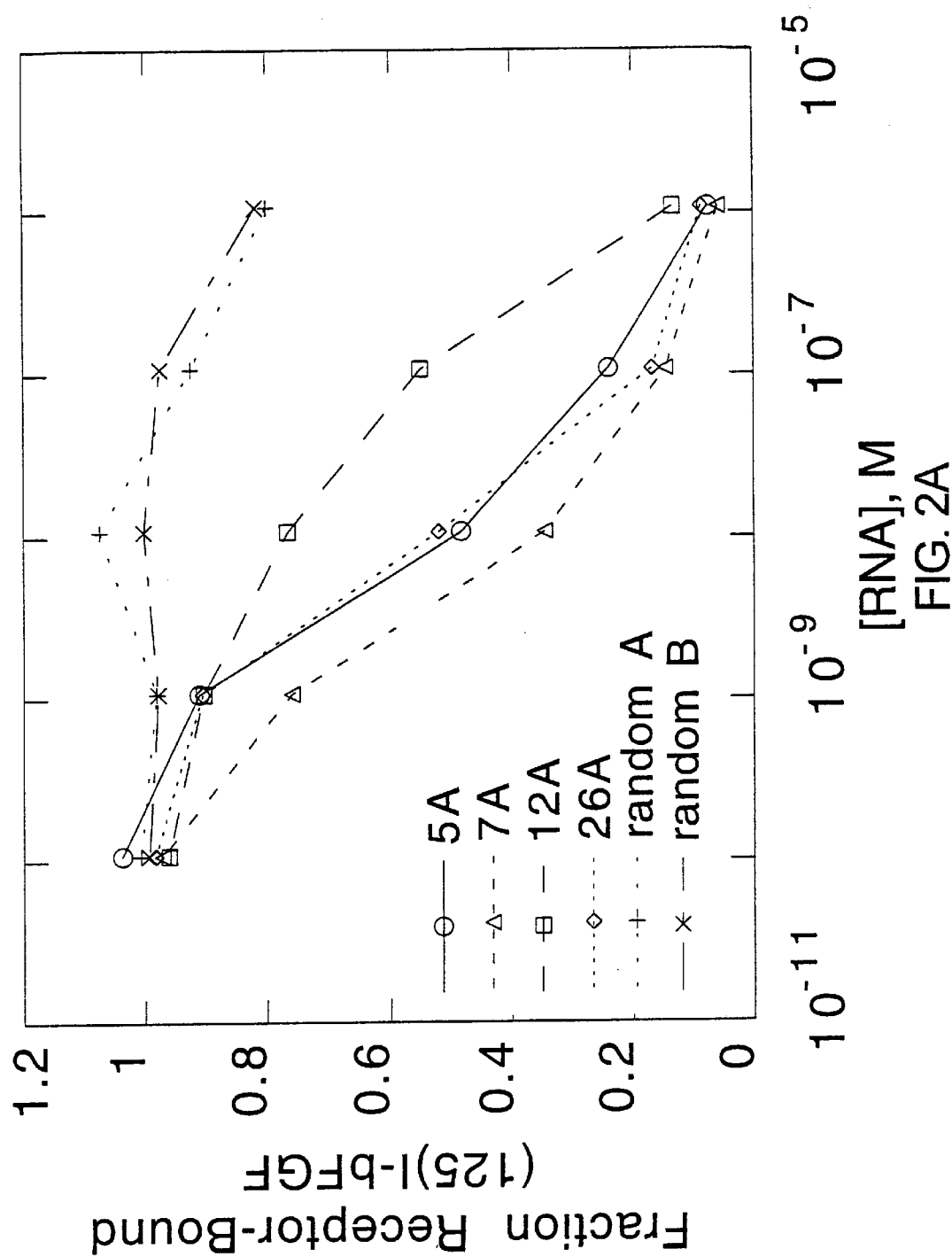
FIGS. 2A and 2B show the effect of bFGF RNA ligands 5A (SEQ ID NO:9) (○), 7A (SEQ ID NO:10) (Δ), 12A (SEQ ID NO:25) (□), 26A (SEQ ID NO:26) (◊), random RNA, SELEX experiment A (+) and random RNA, SELEX experiment B (x) on binding of $^{125}$I-bFGF to the low-affinity (FIG. 2A) and the high-affinity (FIG. 2B) cell-surface receptors. Experiments were done essentially as described in Roghani & Moscatelli (1992) J. Biol. Chem. 267:22156.
Figure 2B:
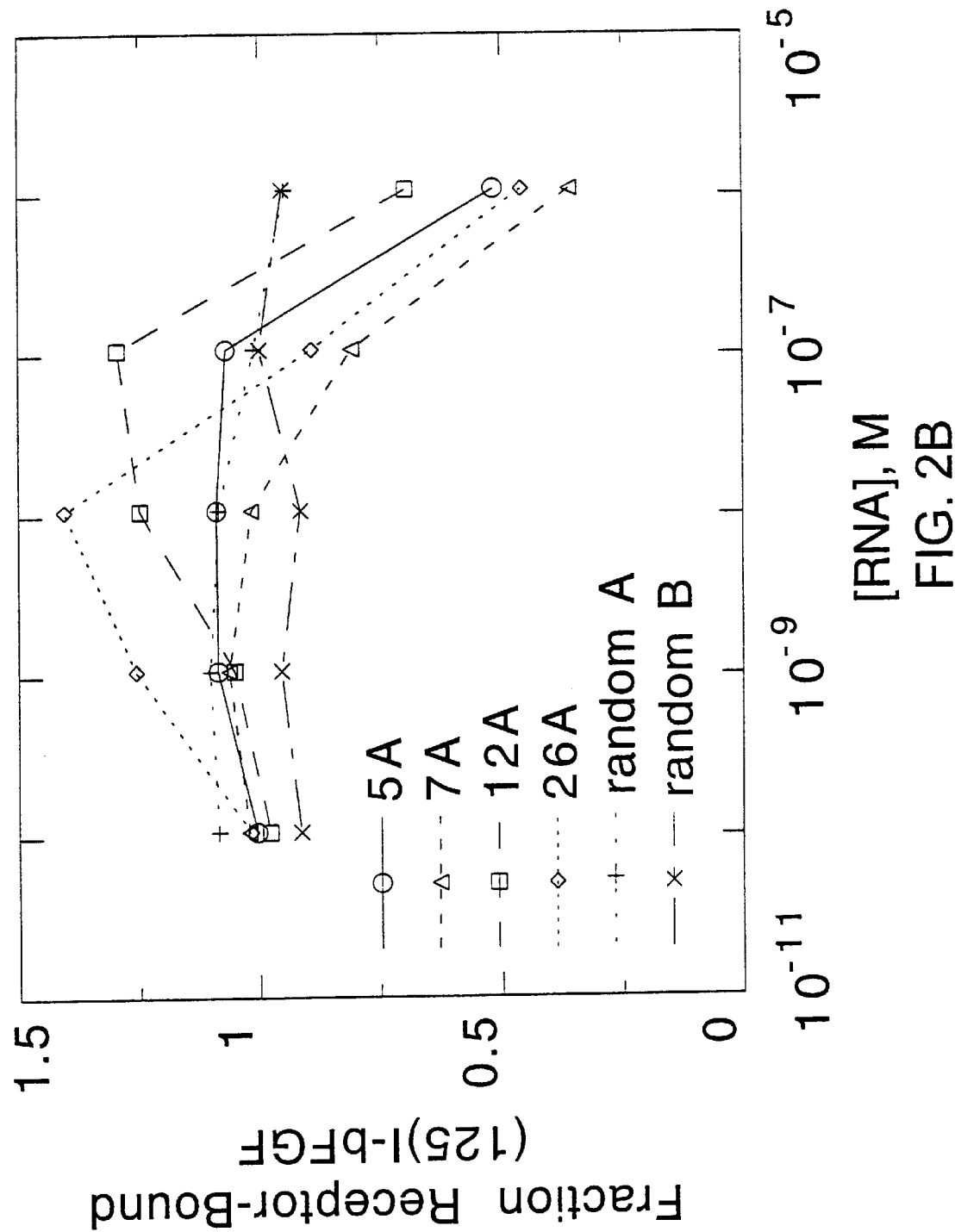

All four ligands competed for the low-affinity receptor sites while the unselected (random) RNAs did not (FIG. 2A). The concentration of RNA required to effect half-displacement of bFGF from the low-affinity receptor was 5–20 nM for ligands 5A, 7A and 26A, and >100 nM for ligand 12A. Half-displacement from the high-affinity sites is observed at the concentration of RNA near 1 μM for ligands 5A, 7A and 26A, and >1 μM for ligand 12A (FIG. 2B). Again, random RNAs did not compete for the high-affinity receptor. The observed difference in concentration of RNA required to displace bFGF from the low- and high-affinity receptors is expected as a reflection of the difference in affinity of the two receptor classes for bFGF (2–10 nM for the low-affinity sites and 10–100 pM for the high-affinity sites).

Figure 3:
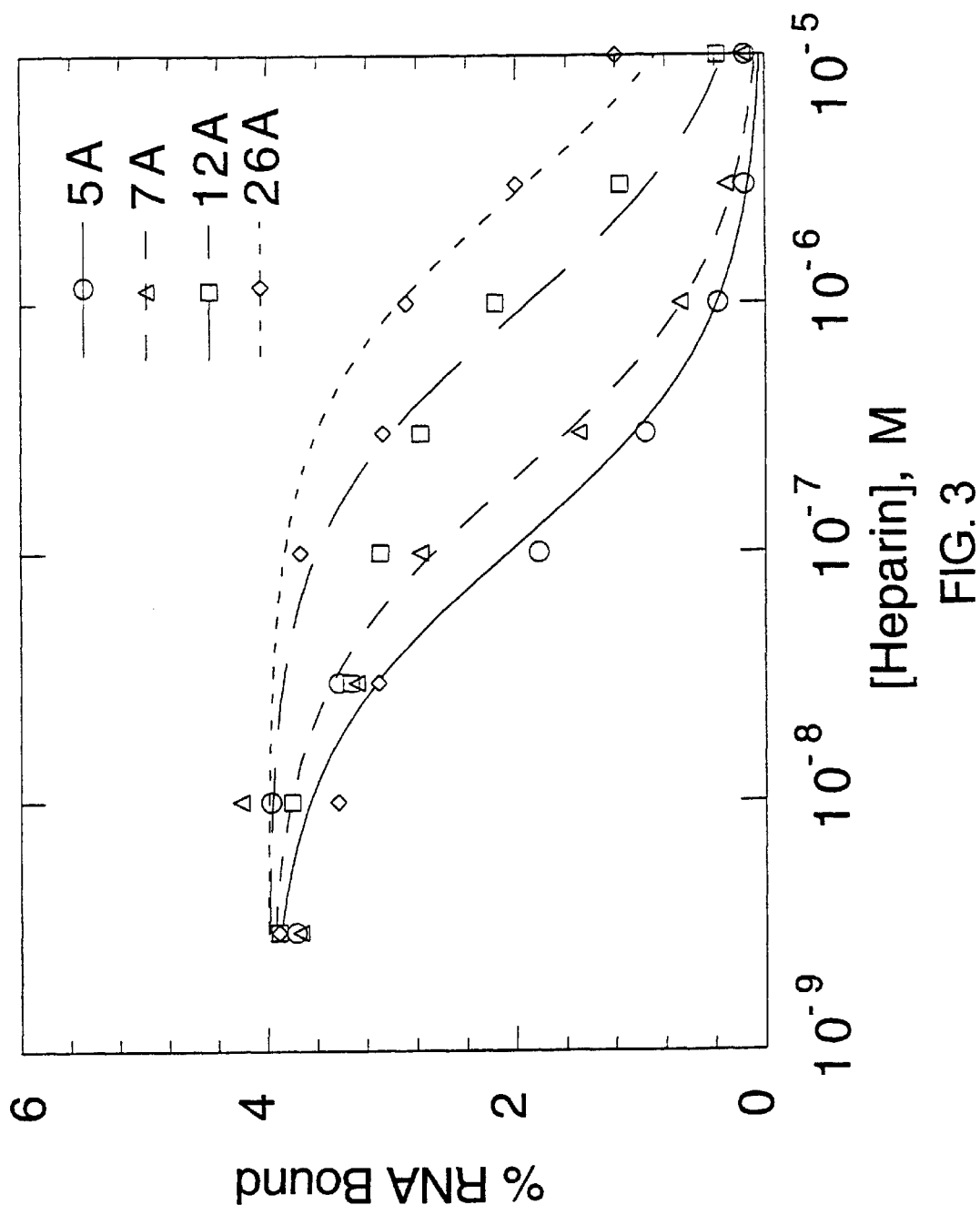
FIG. 3 shows the competitive displacement of $^{32}$p-labeled bFGF RNA ligands 5A (SEQ ID NO:9) (○), 7A (SEQ ID NO:10) (Δ), 12A (SEQ ID NO:25) (□), and 26A (SEQ ID NO:26) (◊) by heparin (average molecular weight 5,000 Da). Percent of total input RNA bound to nitrocellulose filters is plotted as a function of heparin concentration. Experiments were done at 37° C. in phosphate buffered saline containing 0.01% human serum albumin, 0.3 μM RNA, and 30 nM bFGF.
Figure 5:
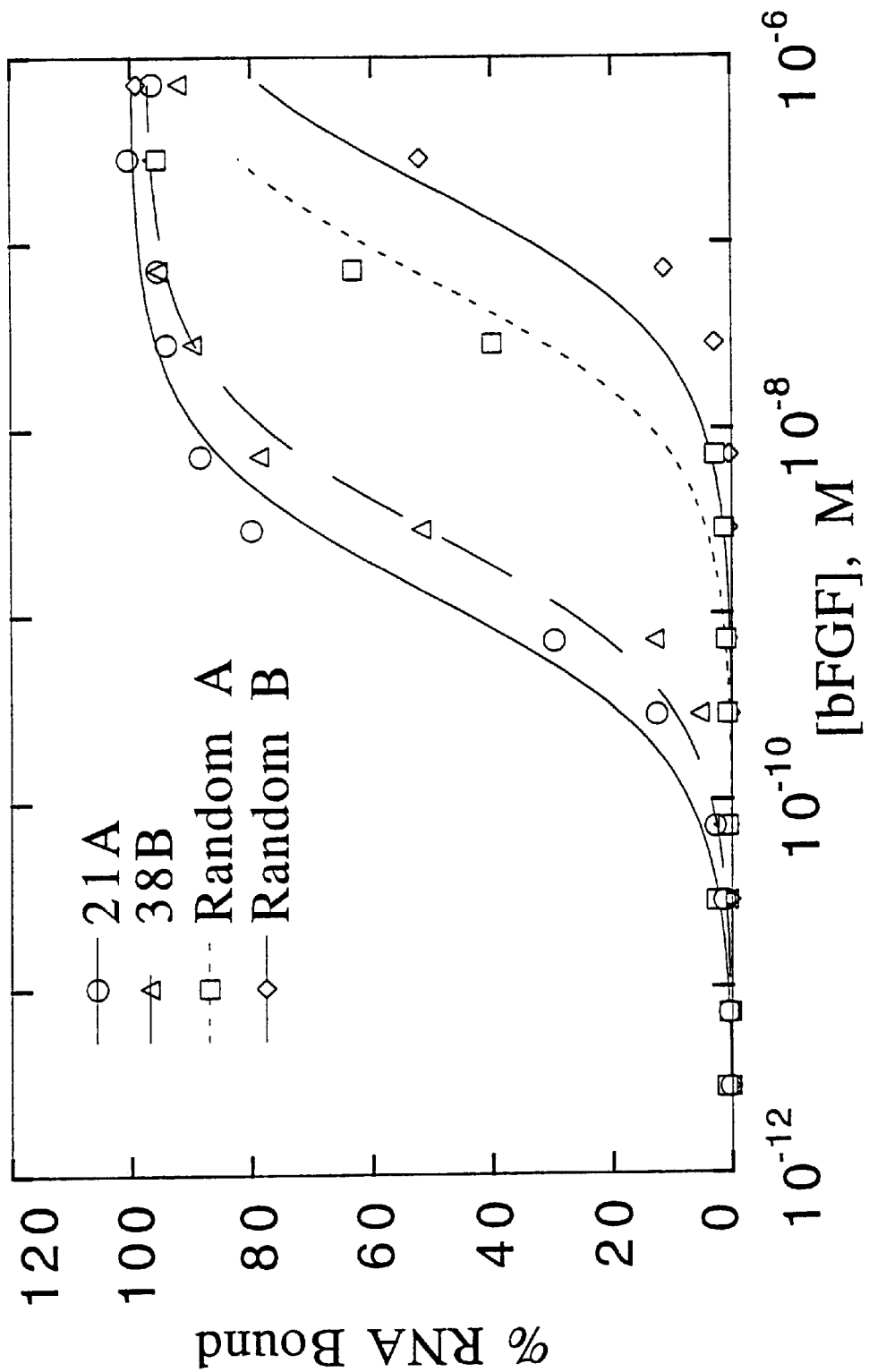
FIG. 5 shows the binding curves for 2'-NH$_2$ modified bFGF RNA ligands 21A (SEQ ID NO:104) (○) (SELEX experiment A), 38B (SEQ ID NO:114) (Δ) (SELEX experiment B) and the initial (random) RNAs (A and B) from which these ligands were selected (□, ◊).

Binding curves for modified RNA ligands 21A (SEQ ID NO:104), 38B (SEQ ID NO:114) and random RNAs were determined (FIG. 5). RNA concentrations were determined from their absorbance reading at 260 nm and were typically less than 100 pM. Binding reactions were conducted at 37° C. in phosphate buffered saline containing 0.01% human serum albumin and 1 mM DTT. Heparin competitively displaced RNA ligands from both sequence families (FIG. 3), although higher concentrations of heparin were required to displace members of Family 2 from bFGF.

The selective advantage obtained through the SELEX procedure is based on affinity to bFGF. RNA ligands can in principle bind to any site on the protein, and it is therefore important to examine the activity of the ligands in an appropriate functional assay. The relevant functional experiment for the selected high-affinity ligands is testing their ability to inhibit binding of bFGF to its cell-surface receptors since this is how bFGF exerts its biological activity. The fact that several representative high-affinity RNA ligands inhibited binding of bFGF to both receptor classes (in accord with their relative binding affinities) suggests that these ligands bind at or near the receptor binding site(s). Further support for this notion comes from the observation that heparin competes for binding of these ligands to bFGF. High affinity ligands from Family 1 and Family 2 may bind to different sites on bFGF. This invention includes covalently connecting components from the two ligand families into a single, more potent inhibitor of bFGF.

EXAMPLE 6

In Vivo Inhibition of bFGF Activity with 2'-NH$_2$-Modified RNA Ligands

The potential in vivo activity of the bFGF antagonist oligonucleotide 2'-NH$_2$ ligand 21A (SEQ ID NO:104) was evaluated in the rat corneal angiogenesis assay. The basic approach for this assay was originally developed and reported by Gimbrone et al. (1974) JNCI 52:413–419 using rabbit corneas for implantation of tumor cells or tumor cell extracts in polyacrylamide gel. The technique was later refined by Langer and Folkman (1976) Nature 263:797 to utilize a less irritating polymer, hydroxyethylmethacrylate (Hydron). The corneal implantation method for assessing angiogenic activity associated with cell extracts or growth factors suspended in Hydron has been used in guinea pigs by Polverini et al. (1977) Nature 269:804 and more recently in rats by Koch et al. (1992) Science 258:1798.

The corneal angiogenesis assay used herein is a modification of the techniques described in the above references. The assay is conducted in rat corneas; however, the implantation method is different in that the corneal pocket is made using small scissors instead of a spatula for the blunt dissection of the corneal stroma. Additionally, Hydron could not be used as the carrier substance for bFGF because the protein was denatured by the high concentration of ethanol and/or the polymerization reaction. Other carriers were studied and it was determined that nitrocellulose filter material (Millipore) was the most suitable medium for implantation since it readily absorbs the protein, is not denaturing to proteins, and is not proinflammatory or irritating to the corneal stroma.

The basic design of the first in vivo assay was to compare the potential angiogenic effects of (1) untreated nitrocellulose, (2) nitrocellulose soaked in oligonucleotide 2'-NH$_2$ ligand 21A, (3) nitrocellulose soaked in bFGF, and (4) nitrocellulose soaked in a solution of ligand 21A and bFGF combined.

The disks to be implanted were punched out of a standard Millipore nitrocellulose filter using a punch made from a 16 gauge hypodermic needle. The diameter of the implanted disks was approximately 1 mm. Prior to implantation the disks were soaked in a given test solution for at least one hour to ensure saturation. The four solutions in this experiment were (1) Ringer's physiologic salt solution, (2) RNA ligand 21A in 10% PBS/90% water, (3) bFGF in Ringer's solution, and (4) 1:1 mixture of ligand 21A and bFGF.

The respective soaked disks were implanted into the corneal stroma of three rats for each treatment group. Both eyes of each rat received the same treatment so that there were six test eyes in each test group. The test solutions were handled using sterile technique. The animals were anesthetized with a general anesthetic mixture containing acepromazine, ketamine, and xylazine. The corneal surgery, which involved making an incision through the corneal epithelium into the underlying stroma with subsequent dissection of a pocket in the stroma, was conducted under a stereomicroscope. The surgical site was cleaned with a dilute solution of organic iodine. A single dose of ophthamic antibiotic was administered post-surgically.

Following implantation of the disks, the animals were returned to their cages where they were maintained under standard husbandry conditions until their eyes were examined stereomicroscopically on post-surgical days seven and fourteen. The eyes were evaluated for amount of corneal cloudiness around the implant and for amount of vascular ingrowth into the normally avascular cornea. The scoring system used for quantitation of vascular ingrowth was based on degrees of vascularization around the circumference of the cornea (potential total=360°) multiplied by the extent of vascular ingrowth toward the implant (1=no growth; 2=ingrowth ⅓ of distance to implant; 3=ingrowth ⅔ of distance to implant; 4=ingrowth to implant; 5=ingrowth into and around implant). The mean score of the eyes in each group was then determined. The minimum score of 360 (360×1) is normal while the maximum possible score with extensive vascular ingrowth into the implant is 1800 (360× 5). The results are shown in Table X.

The results from this preliminary experiment provide two important findings for this ligand. First, although the ligand did not prevent the bFGF stimulated ingrowth of vessels into the cornea (Group IV vs. Group III), it did diminish the amount of vascular ingrowth, as well as, the amount of corneal cloudiness observed microscopically at both seven and fourteen days following implantation. Second, the introduction of the oligonucleotide alone (Group II) into the cornea did not result in any adverse effects such as irritation, inflammation, or angiogenesis. These findings suggest that the oligonucleotide has the desired antagonistic effect for bFGF and that it is biocompatible when administered in vivo at relatively high local concentration (60 μM).

EXAMPLE 7

Endothelial Cell Migration Assay

The effect of minimal 2'-aminopyrimidine RNA ligand on endothelial cell motility was examined by measuring the migration of endothelial cells into a denuded area (Sato, Y. and Rifkin, D. B. (1989) J. Cell Biol. 109:309–315). Confluent monolayers of bovine aortic endothelial (BAE) cells were scraped with a razor blade to create a denuded area on the culture dish. The number of endothelial cells that moved from the edge of the wound into the denuded area in the presence of varying concentrations of oligonucleotide ligands was determined after 8 hours. The movement of BAEs under untreated conditions is dependent on endogenous bFGF and can be inhibited by addition of neutralizing antibodies to bFGF. Ligand 21A-ts (5'-GGUGUGUGGAAGACAGCGGGUGGUUdC-3'(SEQ ID NO:444) inhibited BAE migration in a dose dependent manner at concentrations greater than 50 nM (Ligand 21A-ts is a chemically synthesized analogue of 2'-$NH_2$ ligand 21A-t (SEQ ID NO:186) in which the terminal 2'-aminocytidine has been converted to deoxycytidine. This substitution does not affect high affinity binding to bFGF). The control ligand deoxy(21A-ts) (all deoxy sequence equivalent of 21A-t: 5'-GGTGTGTGGAAGACAGCGGGTGGTTC-3'(SEQ ID NO:445)) did not inhibit BAE migration at the same concentrations. In fact a moderate stimulation of migration was observed. The extent of inhibition at high RNA ligand concentrations varied significantly between experiments ranging from almost 100% to <50% inhibition (data not shown). This is probably related in part to variable expression of other motility-inducing growth factors by BAE cells between experiments as well as subtle differences in the state of the cells at the time of wounding. Importantly, the total amount of motility that could be inhibited by 21A-ts at high concentrations was comparable in all experiments to the effect of 100 μg/ml neutralizing bFGF antibody. This concentration of antibody is generally sufficient to inhibit all of the bFGF-dependent migration of endothelial cells. In a separate experiment we established that the oligonucleotides used in this experiment are not appreciably degraded over the duration of this experiment (8 hr) in a variety of cell culture conditions (data not shown).

EXAMPLE 8 bFGF DNA Ligands

The SELEX protocol was performed in a manner similar to that described in Example 1 to obtain single stranded DNA (ssDNA) ligands to bFGF.

Here, SELEX is performed with single stranded DNA (ssDNA) starting with the three separate sets of synthetic DNA oligonucleotide templates and primers (Experiments 1–3) shown in Table XIX. These experiments are further split into two different methods of ssDNA partitioning from double stranded DNA (dsDNA).

Briefly, in Experiment 1 a population of synthetic DNA oligonucleotides (40N2, SEQ ID NO:322) containing 40 random nucleotides flanked by invariant primer annealing sites was amplified by the Polymerase Chain Reaction (PCR) using oligos 3p2 (SEQ ID NO:323) and $^{32}$P end labeled 5p2 (SEQ ID NO:321) as primers. Oligo 3p2 has three biotin phosphoramidites covalently attached to its 5' terminus during synthesis. In order to generate the ssDNA library from the PCR products, oligo 40N2 was separated from its complement. This was achieved by incubating the PCR reaction in the presence of a 10 fold molar excess of Pierce streptavidin over the biotinylated complement strand. The non-biotinylated ssDNA 40N2 was then purified away from the streptavidin labeled complement strand on a 12% denaturing gel. The ssDNA was eluted from the gel and precipitated, and the ssDNA library used for the selections.

Experiments 2 and 3 used two different populations of synthetic DNA oligonucleotides, oligos 40NBH1 (SEQ ID NO:325), and 30N7.1PS (SEQ ID NO:328), containing 40 and 30 random nucleotides respectively flanked by invariant primer annealing sites. The DNA pools were amplified by the Polymerase Chain Reaction (PCR) using oligos 3pBH1 (SEQ ID NO:326) and 5pBH1 (SEQ ID NO:324) in Experiment 2 and oligos 3p7.1PS (SEQ ID NO:329) and 5p7.1PS (SEQ ID NO:327) in Experiment 3 as primers for the appropriate invariant regions on template molecules. Oligos 3pBH1 and 3p7.1PS had two biotin molecules and two additional A nucleotides covalently attached via standard phosphoramidite coupling to their 5' terminus during synthesis. The non-biotinylated primer was end labeled with $^{32}$P. The radiolabeled non-biotinylated single-stranded PCR products were size-purified away from the biotinylated strand on 8% denaturing acrylamide gels to give single stranded degenerate DNA pools. DNA templates for PCR and the corresponding primers were all synthesized chemically (Operon). The random region was generated by utilizing an equimolar mixture of the four nucleotides during oligonucleotide synthesis.

Using the above methods, three pools of ssDNA oligonucleotides were created that contain internal random regions. From each starting ligand pool approximately $10^{14}$ molecules of DNA was incubated with bFGF at an excess of DNA to target. Oligonucleotides bound to bFGF can be effectively selected from the unbound species by filtration through nitrocellulose membrane filters. The nitrocellulose filters (Millipore, 0.45 μm pore size, type HA) were secured on a filter manifold pre-washed with PBS, the incubation mix washed through and the filter washed with 0.5 M Urea and PBS buffer to remove non-specific DNA from the filter.

The selected DNA (which typically amounts to 1–5% of the total input DNA) was then extracted from the filters. Amplification of the selected ssDNA was performed by PCR under standard conditions yielded sufficient amounts of double-stranded DNA for the next round of selection.

Selections were performed at a large molar excess of ssDNA over protein to promote competition among DNA ligands for the limited number of available target binding sites. The percent of target-dependent DNA retention was minimized for each selection to ensure maximum enrichment of the library for target binders; however, to avoid propagation of members with high affinity for nitrocellulose, selections in which target-free (background) retention was greater than 10% of target-dependent retention were repeated. Target-free selections were performed to measure and correct for background binding levels. The fraction of total DNA retained by the filters was calculated by measuring radiation without fluor in a scintillation counter. The affinity of the pool for bFGF was measured periodically throughout each of the three selection experiments. As the affinity of the population for bFGF increased, the concentrations of ligand and target were reduced accordingly, while the ligand was maintained at an excess concentration, to increase selection stringency. Table XX shows a typical SELEX progression as was seen in Experiment 3. The nucleic acid concentration was maintained at a five fold excess to the bFGF concentration, in all but the first round. Attempts were made to maintain a level of background that was 10 fold lower than the percent bound. The binding affinity was tested after round 0, 8, 10 and 11 to follow the progression.

Cloning and Sequencing.

As indicated in Table XX, significant improvement in affinity of DNA ligands to bFGF was observed in each of the three experiments after ten rounds of selection. Individual members of these enriched pools were then cloned into Stratagene PCR Script SK (+) or pUC18 vector and sequenced. Sequencing of the isolates resulted in 78 individual sequences. Experiment 1 resulted in 36 clones, Experiment 2 resulted in 29, and Experiment 3 resulted in 43. As shown in Table XXI, five distinct families could be identified based on 40% or better overlap in sequence homology. A number of sequences with no obvious homology to members of the five families were also present. These sequences are listed as orphans.

Each family is further divided into the three different SELEX experiments. The consensus sequence for Family 1 ligands is defined by a contiguous stretch of 9 bases, GGGGCTNTGCAAAN (SEQ ID NO:340) where the two N positions are covariant combination of all four bases. This suggests a minimal structure consisting of a 4 nucleotide loop that includes the strongly conserved GCAA sequence. The loop is closed by the formation of a stem containing a T-A basepair and the covariant base pair position.

Determination of Binding Affinities for bFGF.

Equilibrium Dissociation Constants.

In the simplest case, equilibrium binding of DNA to bFGF can be described by equation 3:

$$DNA \bullet bFGF \rightleftharpoons DNA + bFGF \qquad (3)$$

The fraction of bound DNA (q) is related to the concentration of free protein, [P]. Where the concentration of free protein approximates the concentration of total protein (equation 4):

$$q = f[P]/([P]+K_d) \qquad (4)$$

where $K_d$ is the equilibrium dissociation constant and f reflects the efficiency of retention of the protein-DNA complexes on nitrocellulose filters. Mean value of f for bFGF was determined to be 0.82.

In order to eliminate higher order structures, all DNA solutions were heated to 90° C. in PBS for 2–3 minutes and cooled on ice prior to incubation with protein. Relative binding affinity of individual ligands to bFGF cannot be predicted from sequence information. The majority of sequence isolates were therefore screened for their ability to bind to bFGF by measuring the fraction of radiolabeled DNA bound to nitrocellulose filters following incubation with 1 nM protein. This screening method was sufficient to discern those isolates with superior binding to bFGF. Binding of these select isolates was then analyzed in more detail.

High-affinity DNA ligands for bFGF were found in all five sequence families (see (*) in Table XXI), but the DNAs with the lowest Kd values (i.e. ligands with highest affinity) were found in Family 1.

The isolates tested for affinity for bFGF are listed in Table XXII.

Truncation Analysis.

Removal of nucleotides non-essential for binding was performed on selected ligands with high affinity for bFGF, $K_d$s below 1 nM. Those ligands are M225, M19, m234, M235, and D12 (SEQ ID NOS:359, 353, 387, 360, 332). The minimum size of the region necessary for binding was determined to be 35 bases for M225, M19 and D12 (See Truncations, Table XXI M225t3 (SEQ ID NO:364), M19t2 (SEQ ID NO:365), D12t2 (SEQ ID NO:341)). The ligand with the smallest essential sequence, m234, was isolated from Family 2, Experiment 3 and contains 24 nucleotides (m234t2 (SEQ ID NO:391)). The truncated ligands were tested for binding to bFGF. After truncation, ligands M225t3, M19t2, D12t2, M235t2, and m234t2 have kd values of 0.7 nM, 1 nM, 1 nM, 1 nM, and 6 nM respectively (Table XXII). All five of the truncated molecules lost some of their affinity for bFGF in comparison to the full length ligands. The binding affinity is regained when an additional G-C base pair is added to the blunt end stem of M225t3. This molecule is termed M225t3GC (SEQ ID NO:443). The binding of M225t3GC is 0.2 nM compared to 0.7 nM for M225t3 without the additional base pair (Table XXII).

Receptor Binding Studies.

The truncated molecules were tested for their ability to inhibit binding of bFGF to its low- and the high-affinity cell-surface receptors.

bFGF labeled with $^{125}$I was purchased from Amersham. Confluent baby hamster kidney (BHK) cells were washed extensively with PBS and then incubated for 2 hours at 4° C. with a MEM medium containing 10 ng/ml $^{125}$I-bFGF in PBS, 0.1% HSA, 1 unit/ml RNasin, and serial dilutions of high-affinity DNA. The amount of $^{125}$I-bFGF bound to the low- and the high-affinity receptor sites was determined as described by Moscatelli (1987) supra.

All five ligands competed for the low-affinity and high-affinity receptor sites while the unselected (random) RNAs did not. All five ligands show inhibition in the nanomolar range.

Specificity.

Ligand M225t3 (SEQ ID NO:364) the truncated version of the full length isolate M225 (SEQ ID NO:359) was chosen as the preferred ligand for further study. This was based on its sub-nanomolar binding (Table XXII), its Tm of 68° C. which indicates a stable structure, possibly containing a G-C rich stem, and a 35 base truncation. The sequence of M225t3 results in a DNA that folds into a structure containing a 6 base G-C stem terminating in a blunt end. Using the covariant site in the conserved region a GYAA loop can be proposed in the consensus region.

In order to address the question of specificity, ligand M225t3 was tested for binding to vascular endothelial growth factor and human chorionic gonadotropin, both heparin-binding proteins. It was found that the affinity of M225t3 for a these proteins was relatively weak ($K_d$>0.2 μM).

EXAMPLE 9

Conjugation of bFGF Ligand to Peg.

In an effort to determine whether enhanced circulation time could be obtained by conjugating the bFGF to a high molecular weight species, such as PEG, M225t3 DNA was synthesized with a 3' carbon linker terminating in a primary $NH_2$ group. The modified DNA was then reacted with an excess of an N-hydroxysuccinimidyl active ester of PEG 3400. The product was isolated as a slower running band on a gel. It was then labeled and a binding assay performed. The PEG modified M225t3 binds with a similar affinity to bFGF as the non modified ligand. The PEG modified M225t3 binds with the a Kd of 1 nM.

EXAMPLE 10

Evolution of High Affinity RNA Ligands to Thrombin

High affinity RNA ligands for thrombin were isolated by SELEX, as generally described in Example 1. Briefly, random RNA molecules used for the initial candidate mixture were generated by in vitro transcription from a 102 nucleotide double-stranded DNA template containing a random cassette 30 nucleotides (30N) long. A population of $10^{13}$ 30N DNA templates were created by PCR, using a 5' primer containing the T7 promoter for in vitro transcription, and restriction sites in both the 5' and 3' primers for cloning. SELEX was performed with an RNA candidate mixture containing the following 76 nucleotide sequences: 5'-AGAUGCCUGU CGAGCAUGCUG[30N] GUAGCUAAA CAGCUUUGUCGACGGG-3'(SEQ ID NO:320).

The RNA concentration for each round of SELEX was approximately $2-4\times10^{-7}$ M and concentrations of thrombin (Sigma, 1000 units) went from $1.0\times10^{-6}$ in the 1st round to $4.8\times10^{-7}$ in rounds 2 and 3 and $2.4\times10^{-7}$ in rounds 4–12. The binding buffer for the RNA and protein was 100 mM NaCl, 50 mM Tris-Cl, pH 7.7, 1 mM DTT, and 1 mM $MgCl_2$. Binding was for 5 minutes at 37° C. in a total volume of 100 µl in rounds 1–7 and 200 µl in rounds 8–12. Each binding reaction was filtered through a pre-wetted (with 50 mM Tris-Cl, pH 7.7) nitrocellulose filter (2.5 cm Millipore, 0.45 µM) in a Millipore filter binding apparatus, and immediately rinsed with 5 ml of the same buffer. The RNA was eluted from the filters in 400 µl phenol (equilibrated with 0.1 M NaOAc pH 5.2), 200 µl freshly prepared 7 M urea as described (Tuerk et al. (1990) J. Mol. Biol. 213:749–761. The RNA was precipitated with 20 µg tRNA, and was used as a template for cDNA synthesis, followed by PCR and in vitro transcription to prepare RNA for the subsequent round. The RNA was radio-labeled with $^{32}$P-ATP in rounds 1–8 so that binding could be monitored. In order to expedite the time for each round of SELEX, the RNA was not labeled for rounds 9–12. RNA was prefiltered through nitrocellulose filters (1.3 cm Millipore, 0.45 µM) before the 3rd, 4th, 5th, 8th, 11th, and 12th rounds to eliminate selection for any nonspecific nitrocellulose binding.

Binding curves were performed after the 5th, 8th, and 12th rounds to estimate changes in Kd of the bulk RNA (data not shown). These experiments were done in protein excess at concentrations from $1.2\times10^{-5}$ to $2.4\times10^{-9}$ M at a final RNA concentration of $2\times10^{-9}$ M. The RNA for these binding curves was labeled to high specific activity with $^{32}$P-ATP or $^{32}$P-UTP. Binding to nitrocellulose filters was as described for the rounds of SELEX, except that the filter bound RNA was dried and counted directly on the filters.

EXAMPLE 11

Cloning and RNA Sequencing

RNA recovered from the 12th round of SELEX was reverse transcribed into DNA with AMV reverse transcriptase (Life Sciences, Inc.) and the resulting DNA was amplified by PCR using the $^{32}$P 5' end-labeled 3' complementary PCR primer. Digestion at restriction enzyme sites in the 5' and 3' fixed regions were used to remove the 30N region which was subsequently ligated into the complementary sites in the E. coli cloning vector pUC18. Ligated plasmid DNA was transformed into JM103 cells and screened by blue/white colony formation. Colonies containing unique sequences were grown up and miniprep DNA was prepared. Double-stranded plasmid DNA was used for dideoxy sequencing with the Sequenase kit version 2.0 and $^{35}$S-dATP (Amersham). Twenty eight individual clones were sequenced (see Table XII). The ligands were grouped into two classes based upon primary sequence homology.

EXAMPLE 12

Determination of 5' and 3' Boundaries

In order to identify the minimal sequence requirements for high affinity binding, 5' and 3' boundary experiments were performed with end-labeled RNA. Prior to end-labeling, RNA transcribed with T7 polymerase was gel purified by UV shadowing. The RNA was 5' end-labeled by dephosphorylating the 5' end with alkaline phosphatase 1 unit, for 30 minutes at 37° C. Alkaline phosphatase activity was destroyed by phenol:chloroform extraction. RNA was subsequently end-labeled with γ32P-ATP in a reaction with polynucleotide kinase for 30 minutes at 37° C.

RNA was 3' end-labeled with (5'-$^{32}$P)pCp and RNA ligase, for 30 minutes at 37° C. 5' and 3' end-labeled RNAs were gel band purified on an 8%, 8 M urea, polyacrylamide gel.

2 pmole RNA 3' or 5' end-labeled for the 5' or 3' boundary experiments, respectively were hydrolyzed in 50 mM $Na_2CO_3$ (pH 9.0) and 1 mM EDTA in a 10 µl reaction for 10 minutes at 90° C. The reaction was stopped by adding ⅕ volume 3 M NaOAc (pH 5.2), and freezing at −20° C. Binding reactions were done at 3 protein concentrations, 40 nM, 10 nM and 2.5 nM, in 3 volumes (100 µl, 400 µl, and 1600 µl, such that the amount of protein was kept constant) containing 1X binding buffer and 2 pmoles RNA. Reactions were incubated for 10 minutes at 37° C., filtered through a pre-wet nitrocellulose membrane, and rinsed with 5 ml wash buffer. The RNA was eluted from the filters by dicing the filter and shaking it in 200 µl 7 M urea and 400 µl phenol (pH 8.0) for 15 minutes at 20° C. After adding 200 µl $H_2O$, the phases were separated and the aqueous phase extracted once with chloroform. The RNA was precipitated with ⅕ volume 3 M NaOAc, 20 µg carrier tRNA, and 2.5 volumes ethanol. The pellet was washed once with 70% ethanol, dried, and resuspended in 5 µl $H_2O$ and 5 µl formamide loading dye. The remainder of the alkaline hydrolysis reaction was diluted 1:10 and an equal volume of loading dye was added.

To locate where on the sequence ladder the boundary existed, an RNase T1 digest of the ligand was electrophoresed alongside the alkaline hydrolysis reaction and binding reactions. The digest was done in a 10 µl reaction containing 500 fmoles end-labeled RNA and 10 units RNase T1 in 7 M urea, 20 mM sodium citrate (pH 5.0) and 1 mM EDTA. The RNA was incubated for 10 minutes at 50° C. without enzyme and then another 10 minutes after adding enzyme. The reaction was slowed by adding 10 µl loading dyes and incubating at 4° C. Immediately after digestion, 5 µl of each of the digest, hydrolysis, and 3 binding reactions were electrophoresed on a 12% sequencing gel. The boundary experiments gave the boundaries depicted in Table XIII.

33

Based upon these boundaries, possible secondary structures of the thrombin ligand are shown in FIG. 7.

EXAMPLE 13

Synthesis of RNA

RNA molecules corresponding to lower limits of nucleotide sequence required for high affinity binding to thrombin as determined by the boundary experiments (Table XIII and FIG. 7) were synthesized on an Applied Biosystems 394 DNA/RNA Synthesizer. These RNA molecules include the Class I clone 16 (SEQ ID NO:212) hairpin structures of 24 nucleotides (24R) and 39 nucleotides (39R) and the Class II clone 27 (SEQ ID NO:214) hairpin of 33 nucleotides (33R).

EXAMPLE 14

In Vitro Transcription and Binding of 2'-NH$_2$ Modified and Unmodified RNA Ligands Four DNA plasmids with unique 30N sequences were chosen for in vitro transcription of selected unmodified and 2'-NH$_2$ modified RNA ligands from Class I and Class II. 2'-NH$_2$ modified RNA was transcribed directly from the pUC18 plasmid miniprep dsDNA template with T7 RNA polymerase in a reaction containing ATP, GTP, 2'-NH$_2$-UTP and 2'-NH$_2$-CTP. Unmodified RNAs were transcribed in a mixture containing ATP, GTP, UTP, and CTP. For $^{32}$P-labeled RNA, $^{32}$P-ATP was included in the reaction. $^{32}$P-labelled RNA was transcribed with conventional nucleotides, as well as, with the 2'-NH$_2$ derivatives of CTP and UTP. Binding curves with these individual RNAs were established using the binding buffer and thrombin (1000 units, Sigma) concentrations from $1.0 \times 10^{-5}$ to $1.0 \times 10^{-10}$ M. Human α thrombin (Enzyme Research Laboratories, ERL) was also used to determine binding affinities of RNA at concentrations from $1.0 \times 10^{-6}$ to $1.0 \times 10^{-10}$ M.

The 2'-NH$_2$-CTP/UTP modified RNAs of Class I and Class II showed a significant drop in binding when compared to the unmodified RNA (FIG. 9). Binding by the bulk 30N RNA, however, showed a slight increase in affinity when it was modified.

Binding of the 5' end-labeled single stranded 15mer DNA 5'-GGTTGGTGTGGTTGG-3'(G15D) (SEQ ID NO:189) described by Bock et al. (1992) Nature 355:564–565, was determined under the binding conditions described herein with ERL thrombin and compared to binding by the radiolabelled RNA hairpin structures described above. (see FIG. 8C).

EXAMPLE 15

Competition Experiments

To determine whether the RNA ligands described can compete for binding of the DNA 15mer G15D to thrombin, equimolar concentrations (1 μM) of thrombin and the 5° end labeled DNA 15mer G15D were incubated under filter binding conditions (Kd of approximately 200 nM) in the presence and absence of 'cold' unlabeled RNA or DNA ligand at varying concentrations from 10 nM to 1 μM. In the absence of competition, RNA binding was 30%. The protein was added last so competition for binding could occur. The RNA ligands tested for competition were the Class I clone 16 (SEQ ID NO:212) synthetic RNAs 24mer (24R) and 39mer hairpins (39R) and the Class II 27 (SEQ ID NO:214) synthetic RNA 33mer (33R). Results are expressed as the relative fraction of G15D bound (G15 with competitor/G15 without competitor) versus the concentration of cold competitor.

34

To determine whether Class I RNAs can compete for binding with Class II RNAs and to confirm the competition with the G15D DNA, equimolar concentrations (300 nM) of thrombin and the 5' end-labelled Class II RNA 33 hairpin were incubated under filter binding conditions in the presence or absence of 'cold' unlabelled RNA 24 or DNA G15D at varying concentrations from 100 nM to 32 μM. Results are expressed as the relative fraction of RNA 33 bound (RNA 33 with competitor/RNA 33 without competitor) versus the concentration of cold competitor (FIG. 10).

EXAMPLE 16

Chromogenic Assay for Thrombin Activity and Inhibition by RNA Ligands

The hydrolysis by thrombin of the chromogenic substrate S-2238 (H-D-Phe-Pip-Arg-pNitroaniline [H-D-Phe-Pip-Arg-pNA]) (Kabi Pharmacia) was measured photometrically at 405 nm due to the release of p-nitroaniline (pNA) from the substrate.

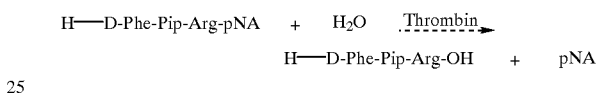

Thrombin was added to a final concentration of $10^{-8}$ or $10^{-9}$ M to a reaction buffer (50 mM sodium citrate, pH 6.5, 150 mM NaCl, 0.1% PEG), containing 250 μM S2238 substrate at 37° C. For inhibition assays, thrombin plus RNA (equimolar or at 10-fold excess) were preincubated 30 secs at 37° C. before adding to the reaction mixture (Table XIV).

EXAMPLE 17

Fibrinogen Clotting

Thrombin was added for a final concentration of 2.5 nM to 400 μl incubation buffer (20 mM Tris-acetate, pH 7.4, 140 mM NaCl, 5 mM KCl, 1 mM CaCl$_2$, 1 mM MgCl$_2$) containing 0.25 mg/ml fibrinogen and 1 u/λ RNAse inhibitor (RNAasin, Promega) with or without 30 nM RNA Class I or 60 nM RNA Class II at 37° C. Time in seconds from addition of thrombin to clot formation was measured by the tilt test (Table XIV).

EXAMPLE 18

Specificity of Thrombin Binding

The binding affinity of the full-length class I RNA 16 (SEQ ID NO:198), class II RNA 27 (SEQ ID NO:209) and bulk 30N3 RNA for the serum proteins Antithrombin III (ATIII) and Prothrombin was determined by filter binding, as described above for the evolution of high affinity RNA ligands (Example 10). These experiments were done in protein excess at concentrations from $1 \times 10^{-5}$ to $5 \times 10^{-10}$ M at a final RNA concentration of $2 \times 10^{-9}$ M (FIG. 11).

EXAMPLE 19

Evolution of High Affinity DNA Ligands to Thrombin

High affinity single-stranded DNA (ssDNA) ligands for thrombin were isolated by SELEX. Two populations of approximately $10^{14}$ ssDNA molecules with either a 30-nucleotide (30N) (SEQ ID NO:215) or 60-nucleotide (60N) (SEQ ID NO:260) variable region and 5' and 3' fixed regions were synthesized for the initial selection. Thrombin and DNA were incubated in a buffer containing 50 mM Tris-Cl, pH 7.5, 100 mM NaCl, 1 mM MgCl$_2$ at 37° C. for 5 minutes. The thrombin-bound DNA was partitioned from unbound DNA by nitrocellulose-filter binding. DNA was eluted from the filters by denaturation and phenol/chloroform extraction. A double-stranded DNA product with 3 biotin molecules at the 5' end of the complementary strand was created and amplified by PCR using a 3' complimentary biotinylated primer and sense 5' primer. The double-stranded product was bound to a streptavidin-agrose matrix and the nonbiotinylated ssDNA template was isolated by alkaline denaturation. This ssDNA template pool was used for the following round of SELEX.

Figure 12:
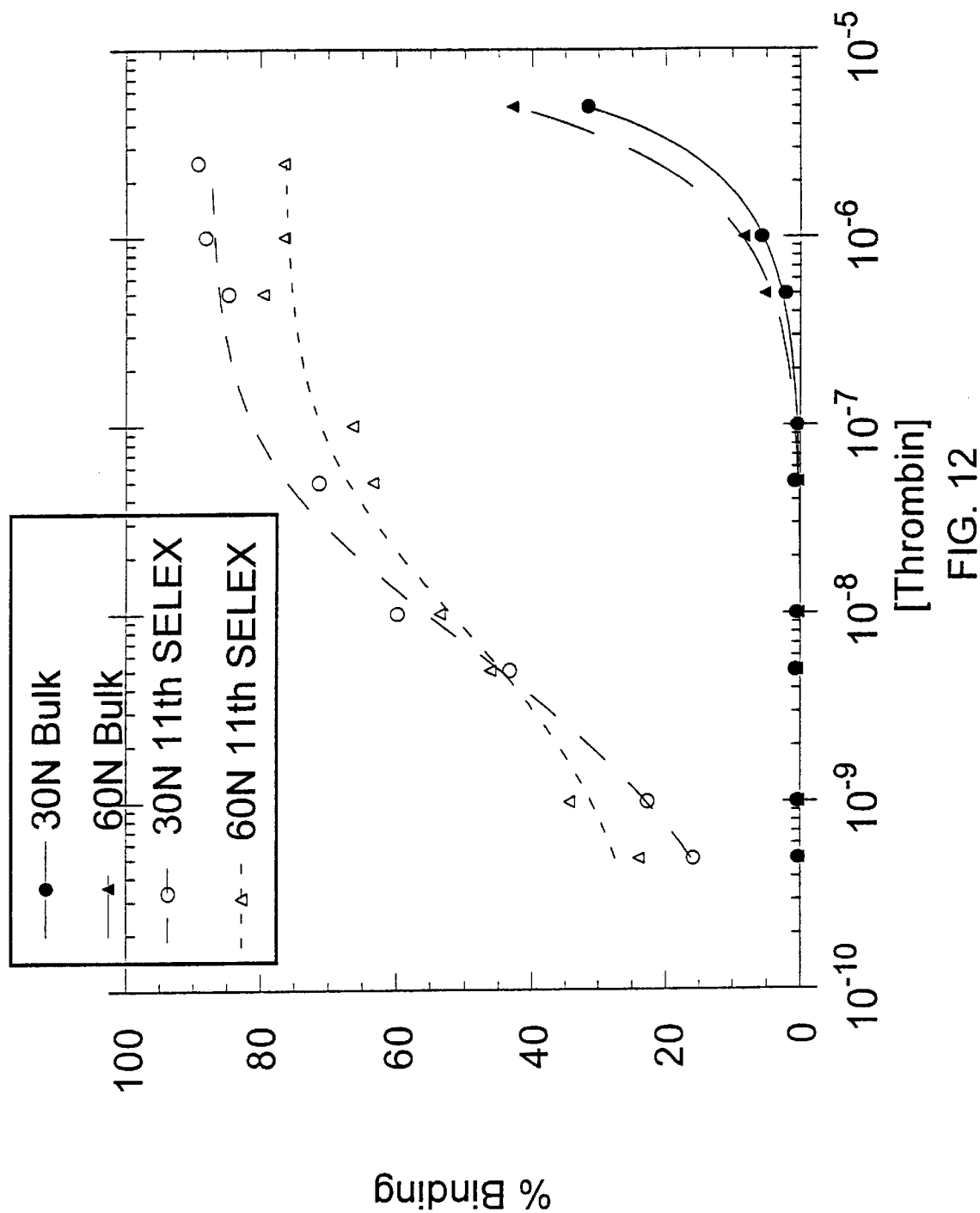
FIG. 12 shows the results of nitrocellulose filter binding assays for the 30N and 60N DNA candidate mixtures and the nucleic acid pools, both 30N and 60N, after performing 11 rounds of SELEX to thrombin.
Figure 13:
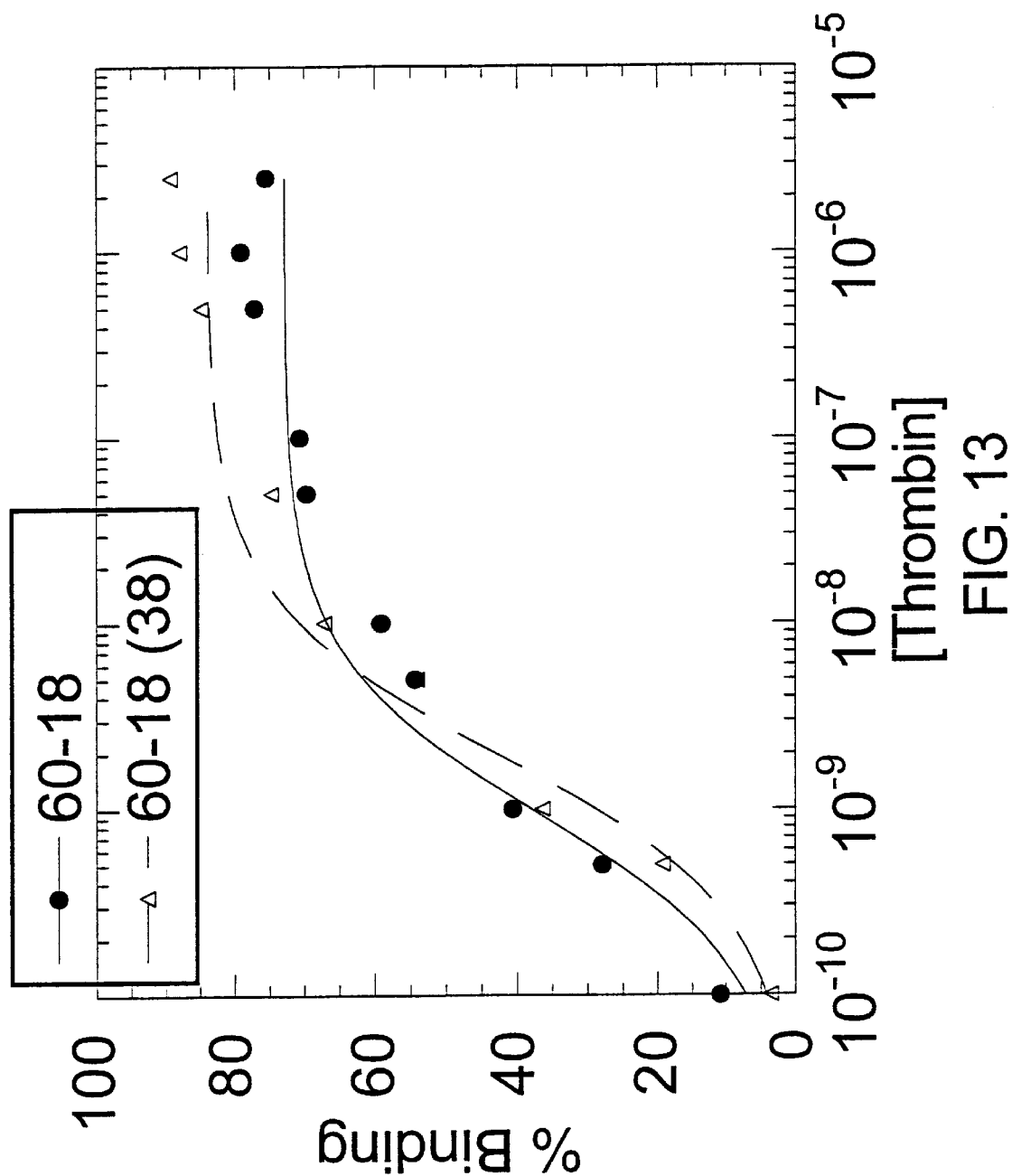
FIG. 13 depicts the binding curve for the truncated thrombin DNA ligand referred to as 60-18(38) (SEQ ID NO:278) and the binding curve for the non-truncated form of the same DNA ligand, 60-18 (SEQ ID NO:279).
Figure 14:
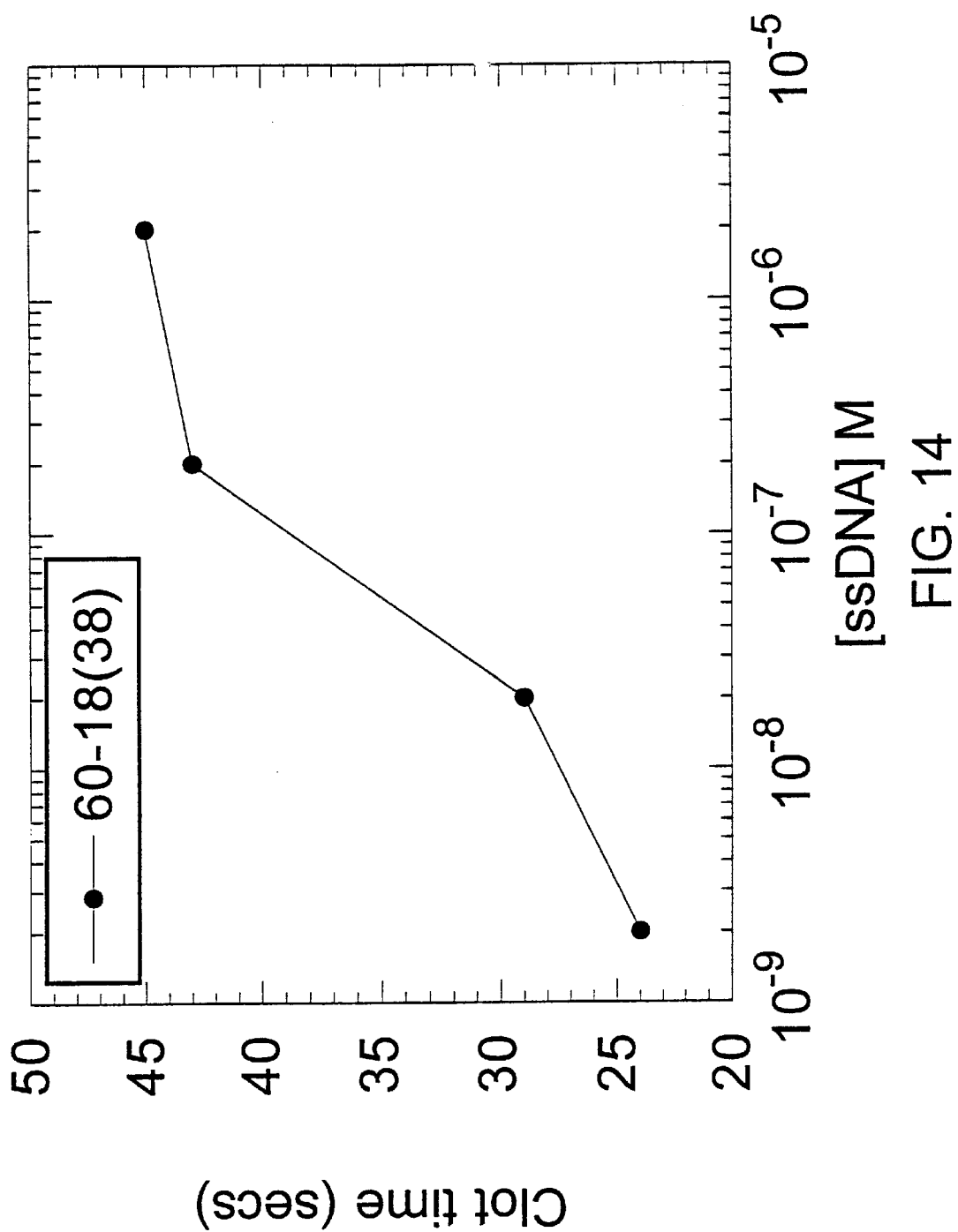
FIG. 14 depicts the results of the thrombin DNA ligand 60-18(38) (SEQ ID NO:278) in the clot inhibition assay.

Nitrocellulose filter binding was used to determine Kds. No additional improvement in binding was seen after 12 rounds of SELEX where the Kds for the 30N and 60N populations were both determined to be approximately 8 nM (FIG. 12). The Kds for the bulk 30N and 60N populations after 12 rounds of SELEX were approximately 8 μM and 5 μM, respectively. Double-stranded DNA from the 12th round was digested with restriction enzyme sites in the 5' and 3' fixed regions and ligated into the complementary sites of the *E. coli* cloning vector pUC18. Plasmid DNA was prepared and used for dideoxy sequencing by PCR. Twenty-eight clones from the 30N population were sequenced and 24 unique sequences were identified while thirty-two clones from 60N population were sequenced and 31 unique sequences were identified (Table XV). ssDNA from individual clones 6 (SEQ ID NO:219), 8 (SEQ ID NO:221), 14 (SEQ ID NO:224), 16 (SEQ ID NO:226), and 35 (SEQ ID NO:238) from the 30N population and 7 (SEQ ID NO:236), 18 (SEQ ID NO:256), and 27 (SEQ ID NO:264) from the 60N population was prepared and Kds were determined by nitrocellulose filter binding. Kds ranged from 0.4 nM to 9.4 nM for the 30N DNAs and from 0.9 to 2.5 nM for the 60N DNAs (Table XVI). Regions of homology between these DNA are indicated in bold and G-nucleotide residues that may be involved in quadruplex formation are also underlined. A truncated ligand of 38 nucleotides from the high affinity clone 60-18 (SEQ ID NO:278)(Kd=0.9 nM), designated 60-18(38) (SEQ ID NO:279) has been identified (Kd=1.9 nM; Table XVI) that retains high-affinity binding (FIG. 13) and inhibits clotting (FIG. 14).

TABLE I

OLIGONUCLEOTIDES USED IN SELEX EXPERIMENTS A AND B TO SELECT RNA LIGANDS TO bFGF.

| | SEQUENCE 5'-3' | SEQ ID NO. |
|---|---|---|
| EXPERIMENT A | | |
| Starting RNA | GGGAGCUCAGAAUAAACGCUCAANNNNNNNNNNNNNN NNNNNNNNNNNNNNNNUUCGACAUGAGGCCCGGAUCCGGC | SEQ ID NO:1 |
| PCR Primer 1 | <u>HindIII</u><br>CCGAAGCTT<u>AATACGACTCACTATA</u>GGGAG<br>T7 Promoter<br>CTCAGAATAAACGCTCAA | SEQ ID NO:2 |
| PCR Primer 2 | <u>BamH1</u><br>GCCGGATCCGGGCCTCATGTCGAA | SEQ ID NO:3 |
| EXPERIMENT B | | |
| Starting RNA | GGGAGAUGCCUGUCGAGCAUGCUGNNNNNNNNNNNNNNN NNNNNNNNNNNNNNNGUAGCUAAACAGCUUUGUCGACGGG | SEQ ID NO:4 |
| PCR Primer 1 | <u>HindIII</u><br>CCCGAAGCTT<u>AATACGACTCACTATA</u>GGGAG<br>T7 Promoter<br>ATGCCTGTCGAGCATGCTG | SEQ ID NO:5 |
| PCR Primer 2 | <u>Sal1</u><br>CCCGTCGACAAAGCTGTTTAGCTAC | SEQ ID NO:6 |

TABLE II

FAMILY 1 SEQUENCES FROM SELEX EXPERIMENTS A AND B.
CONSENSUS SEQUENCE
CUAACCAGG (SEQ ID NO: 7)
gggagcucagaauaaacgcucaa-[30N]-uucgacaugaggcccggauccggc (SEQ ID NO: 1)

| | | | SEQ ID NO. |
|---|---|---|---|
| FAMILY 1 | CLONE | (30N) | |
| | 4A | UGCUAUUCGCCUAACUCGGCGCUCCUACCU | SEQ ID NO:8 |
| | 5A | AUCUCCUCCCGUCGAAGCUAACCUGGCCAC | SEQ ID NO:9 |

TABLE II-continued

FAMILY 1 SEQUENCES FROM SELEX EXPERIMENTS A AND B.
CONSENSUS SEQUENCE
CUAACCAGG (SEQ ID NO: 7)

gggagcucagaauaaacgcucaa-[30N]-uucgacaugaggcccggauccggc (SEQ ID NO: 1)

|     |                                    | SEQ ID NO. |
|-----|------------------------------------|------------|
| 7A  | UCGGCGAGCUAACCAAGACACUCGCUGCAC     | SEQ ID NO:10 |
| 10A | GUAGCACUAUCGGCCUAACCCGGUAGCUCC     | SEQ ID NO:11 |
| 13A | ACCCGCGGCCUCCGAAGCUAACCAGGACAC     | SEQ ID NO:12 |
| 14A | UGGGUGCUAACCAGGACACACCCACGCUGU     | SEQ ID NO:13 |
| 16A | ACGCACAGCUAACCAAGCCACUGUGCCCC      | SEQ ID NO:14 |
| 18A | CUGCGUGGUAUAACCACAUGCCCUGGGCGA     | SEQ ID NO:15 |
| 21A | UGGGUGCUUAACCAGGCCACACCCUGCUGU     | SEQ ID NO:16 |
| 25A | CUAGGUGCUAUCCAGGACUCUCCCUGGUCC     | SEQ ID NO:17 |
| 29A | UGCUAUUCGCCUAGCUCGGCGCUCCUACCU     | SEQ ID NO:18 |
| 38A | AGCUAUUCGCCCAACCCGGCGCUCCCGACC     | SEQ ID NO:19 |
| 39A | ACCAGCUGCGUGCAACCGCACAUGCCUGG      | SEQ ID NO:20 |
| 56A | CAGGCCCCGUCGUAAGCUAACCUGGACCCU     | SEQ ID NO:21 |
| 61A | UGGGUGCUAACCACCACACACUCACGCUGU     | SEQ ID NO:22 |

TABLE III

FAMILY 2 SEQUENCES FROM SELEX EXPERIMENTS A AND B.
CONSENSUS SEQUENCE:
RRGGHIAACGYWNNGDCAAGNNCACYY
(SEQ ID NO: 23)

| FAMILY 2 | CLONE (30N) | SEQ ID NO. |
|----------|-------------|------------| gggagcucagaauaaacgcucaa-[30N]-uucgacaugaggcccggauccggc (SEQ ID NO:1)

| 11A | GGGUAACGUUGU  GACAAGUACACCUGCGUC  | SEQ ID NO:24 |
| 12A | GGGGCAACGCUACA  GACAAGUGCACCCAAC  | SEQ ID NO:25 |
| 26A | CGUCAGAAGGCAACGUAUA  GGCAAGCACAC  | SEQ ID NO:26 |
| 27A | CCUCUCGAAGACAACGCUGU  GACAAG ACAC | SEQ ID NO:27 |
| 47A | AGUGGGAAACGCUACUUGACAAG ACACCAC   | SEQ ID NO:28 |
| 65A | GGCUACGCUAAU  GACAAGUGCACUUGGGUG  | SEQ ID NO:29 | gggagaugccugucgagcaugcug-[30N]-guagcuaaacagcuuugucgacggg (SEQ ID NO:4)

| 1B  | CUCUGGUAACGCAAU  GUCAAGUGCACAUGA  | SEQ ID NO:30 |
| 2B  | AGCCGCAGGUAACGGACC  GGCGAGACCAUU  | SEQ ID NO:31 |
| 6B  | ACGAGCUUCGUAACGCUAUC  GACAAGUGCA  | SEQ ID NO:32 |
| 8B  | AAGGGGAAACGUUGA  GUCCGGUACACCCUG  | SEQ ID NO:33 |
| 9B  | AGGGUAACGUACU  GGCAAGCUCACCUCAGC  | SEQ ID NO:34 |
| 11B | GAGGUAACGUAC  GACAAGACCACUCCAACU  | SEQ ID NO:35 |
| 12B | AGGUAACGCUGA  GUCAAGUGCACUCGACAU  | SEQ ID NO:36 |
| 13B | GGGAAACGCUAUC  GACGAGUGCACCCGGCA  | SEQ ID NO:37 |
| 14B | CCGAGGGUAACGUUGG  GUCAAGCACACCUC  | SEQ ID NO:38 |

TABLE III-continued

FAMILY 2 SEQUENCES FROM SELEX EXPERIMENTS A AND B.
CONSENSUS SEQUENCE:
RRGGHIAACGYWNNGDCAAGNNCACYY
(SEQ ID NO: 23)

| FAMILY 2 | CLONE (30N) | | SEQ ID NO. |
|---|---|---|---|
| 15B | UCGGGGUAACGUAUU | GGCAAGGC ACCCGAC | SEQ ID NO:39 |
| 19B | GGUAACGCUGUG | GACAAGUGCACCAGCUGC | SEQ ID NO:40 |
| 22B | AGGGUAACGUACU | GGCAAGCUCACCUCAGC | SEQ ID NO:41 |
| 28B | AGGGUAACGUAUA | GUCAAGAC ACCUCAAGU | SEQ ID NO:42 |
| 29B | GGGUAACGCAUU | GGCAAGAC ACCCAGCCCC | SEQ ID NO:43 |
| 36B | GAGGAAACGUACC | GUCGAGCC ACUCCAUGC | SEQ ID NO:44 |
| 38B | AGGUAACGCUGA | GUCAAGUGCACUCGACAU | SEQ ID NO:45 |
| 48B | GGGUAACGUGU | GACAAGAUCACCCAGUUUG | SEQ ID NO:46 |
| 49B | CACAGGGCAACGCUGCU | GACAAGUGCACCU | SEQ ID NO:47 |

TABLE IV

OTHER SEQUENCES FROM SELEX EXPERIMENTS A AND B.

| NUMBER | CLONE (30N) | SEQ ID NO. |
|---|---|---|
| gggagcucagaauaaacgcucaa-[30N]-uucgacaugaggcccggauccggc (SEQ ID NO: 1) | | |
| 8A | ACGCCAAGUGAGUCAGCAACAGAGCGUCCG | SEQ ID NO:48 |
| 9A | CCAGUGAGUCCUGGUAAUCCGCAUCGGGCU | SEQ ID NO:49 |
| 24A | CUUCAGAACGGCAUAGUGGUCGGCCGCGCC | SEQ ID NO:50 |
| 33A | AGGUCACUGCGUCACCGUACAUGCCUGGCC | SEQ ID NO:51 |
| 34A | UCCAACGAACGGCCCUCGUAUUCAGCCACC | SEQ ID NO:52 |
| 36A | ACUGGAACCUGACGUAGUACAGCGACCCUC | SEQ ID NO:53 |
| 37A | UCUCGCUGCGCCUACACGGCAUGCCGGGA | SEQ ID NO:54 |
| 40A | GAUCACUGCGCAAUGCCUGCAUACCUGGUC | SEQ ID NO:55 |
| 43A | UCUCGCUGCGCCUACACGGCAUGCCCGGGA | SEQ ID NO:56 |
| 44A | UGACCAGCUGCAUCCGACGAUAUACCCUGG | SEQ ID NO:57 |
| 45A | GGCACACUCCAACGAGGUAACGUUACGGCG | SEQ ID NO:58 |
| 55A | AGCGGAACGCCACGUAGUACGCCGACCCUC | SEQ ID NO:59 |
| gggagaugccugucgagcaugcug-[30N]-guagcuaaacagcuuugucgacggg (SEQ ID NO: 4) | | |
| 4B | ACCCACGCCCGACAACCGAUGAGUUCUCGG | SEQ ID NO:60 |
| 5B | UGCUUUGAAGUCCUCCCCGCCUCUCGAGGU | SEQ ID NO:61 |
| 7B | AUGCUGAGGAUAUUGUGACCACUUCGGCGU | SEQ ID NO:62 |
| 16B | ACCCACGCCCGACAACCGAUGAGCUCGGA | SEQ ID NO:63 |
| 20B | AGUCCGGAUGCCCCACUGGGACUACAUUGU | SEQ ID NO:64 |
| 21B | AAGUCCGAAUGCCACUGGGACUACCACUGA | SEQ ID NO:65 |
| 23B | ACUCUCACUGCGAUUCGAAAUCAUGCCUGG | SEQ ID NO:66 |
| 40B | AGGCUGGGUCACCGACAACUGCCCGCCAGC | SEQ ID NO:67 |

TABLE IV-continued

OTHER SEQUENCES FROM SELEX EXPERIMENTS A AND B.

| NUMBER | CLONE (30N) | SEQ ID NO. |
|---|---|---|
| 42B | AGCCGCAGGUAACGGACCGGCGAGACCACU | SEQ ID NO:68 |
| 26B | GCAUGAAGCGGAACUGUAGUACGCGAUCCA | SEQ ID NO:69 |

TABLE V

REPEAT SEQUENCES FROM SELEX EXPERIMENTS A AND B.

| NUMBER | SEQ ID NO. | CLONE REPEATED |
|---|---|---|
| gggagcucagaauaaacgcucaa-[30N]-uucgacaugaggcccggauccggc (SEQ ID NO: 1) | | |
| 3A    GGGUAACGUUGUGACAAGUACACCUGCGUC | SEQ ID NO:70 | 11A |
| 15A   GGGUAACGUUGUGACAAGUACACCUGCGUC | SEQ ID NO:71 | 11A |
| 20A   GGGUAACGUUGUGACAAGUACACCUGCGUC | SEQ ID NO:72 | 11A |
| 48A   GGGUAACGUUGUGACAACUACACCUGCGUC | SEQ ID NO:73 | 11A |
| 58A   GGGUAACGUUGUGACAACUACACCUGCGUC | SEQ ID NO:74 | 11A |
| 64A   GGGUAACGUUGUGACAACUACACCUGCGUC | SEQ ID NO:75 | 11A |
| 28A   CGUCAGAAGGCAACGUAUAGGCAAGCACAC | SEQ ID NO:76 | 26A |
| 30A   GUAGCACUAUCGGCCUAACCCGGUAGCUCC | SEQ ID NO:77 | 10A |
| 23A   ACCCGCGGCCUCCGAAGCUAACCAGGACAC | SEQ ID NO:78 | 13A |
| 46A   AGGUCACUGCGUCACCGUACAUGCCUGGCC | SEQ ID NO:79 | 33A |
| 49A   AGGUCACUGCGUCACCGUACAUGCCUGGCC | SEQ ID NO:80 | 33A |
| 50A   GGCACACUCCAACGAGGUAACGUUACGGCG | SEQ ID NO:81 | 45A |
| 41A   GGGGCAACGCUACAGACAAGUGCACCCAAC | SEQ ID NO:82 | 12A |
| 51A   GGGGCAACGCUACAGACAAGUGCACCCAAC | SEQ ID NO:83 | 12A |
| 54A   GGGGCAACGCUACAGACAAGUGCACCCAAC | SEQ ID NO:84 | 12A |
| 35A   UGGGUGCUAACCAGGACACACCCACGCUGU | SEQ ID NO:85 | 14A |
| gggagaugccugucgagcaugcug-[30N]-guagcuaaacagcuuugucgacggg (SEQ ID NO: 4) | | |
| 18B   CCGAGGGUAACGUUGGGUCAAGCACACCUC | SEQ ID NO:86 | 14B |
| 24B   GGGAAACGCUAUCGACGAGUGCACCCGGCA | SEQ ID NO:87 | 13B |
| 39B   GGGAAACGCUAUCGACGAGUGCACCCGGCA | SEQ ID NO:88 | 13B |
| 37B   ACUCUCACUGCGAUUCGAAAUCAUGCCUGG | SEQ ID NO:89 | 23B |
| 43B   GCAUGAAGCGGAACUGUAGUACGCGAUCCA | SEQ ID NO:90 | 26B |
| 46B   GCAUGAAGCGGAACUGUAGUACGCGAUCCA | SEQ ID NO:91 | 26B |
| 25B   AGGGUAACGUACUGGCAAGCUCACCUCAGC | SEQ ID NO:92 | 9B |
| 33B   AGGGUAACGUACUGGCAAGCUCACCUCAGC | SEQ ID NO:93 | 9B |
| 31B   GGUAACGCUGUGGACAAGUGCACCAGCUGC | SEQ ID NO:94 | 19B |

TABLE VI

SECONDARY STRUCTURES AND DISSOCIATION CONSTANTS ($K_d$'s) FOR A REPRESENTATIVE SET OF HIGH-AFFINITY LIGANDS FROM FAMILY 1.

| LIGAND | STRUCTURE[a] | $K_d$, nM | SEQ ID NO: (PARENT SEQUENCE) |
|---|---|---|---|
| 5A-t[b] | <pre>        CC              AA<br>    CCUC  GUCGAA---GCU    C<br>    ggag  cagcuu   CGG    C<br>        ua      CAC    U</pre> | 23 ± 3 | 9 |
| 7A-t[b] | <pre>                    AA<br>    CGGCGAG---CU    C<br>    GUCGCUC    GA    C<br>          ACA    A</pre> | 5.0 ± 0.5 | 10 |
| 13A-t[b] | <pre>      C                       A<br>    CCG GGCCUC----CGAAG-----CU  A<br>    ggc-ccggag    gcuuC     GA  C<br>          uaca       ACAG    C</pre> | 3.2 ± 0.5 | 12 |
| 14A-t[b] | <pre>      cucaa             A<br>    aaacg     UGGGUG----CU  A<br>    uuUGU-    -ACCCAC    GA  C<br>         CGC       ACAG    C</pre> | 3.0 ± 0.5 | 13 |
| 21A-t[b] | <pre>                       A<br>    aaU----GGGU---GCUU  A<br>    uUG    CCCA   CGGA  C<br>         UCGU    CAC    C</pre> | 8.1 ± 0.8 | 16 |
| 25A-t[b] | <pre>                   A<br>    CUA-GGUG----CU  U<br>    GGU CCUC     GA  C<br>      C     UCAG    C</pre> | 5.9 ± 1.4 | 17 |
| 39A-t[b] | <pre>          CU         A<br>    AACCAG  GC--GUGC  A<br>    uuGGUC--CG  CACG  C<br>             UA      C</pre> | 8.5 ± 1.2 | 20 |

[a]Strongly conserved positions are shown in boldface symbols. Nucleotides in the constant region are in lowercase type.
[b]The letter "t" is used to designate truncated sequences derived from the corresponding parent sequences (FIG. XVII).

TABLE VII

SECONDARY STRUCTURES AND DISSOCIATION CONSTANTS ($K_d$'s) FOR A REPRESENTATIVE SET OF HIGH-AFFINITY LIGANDS FROM FAMILY 2.

| LIGAND | STRUCTURE[a] | $K_d$, nM | SEQ ID NO: (PARENT SEQUENCE) |
|---|---|---|---|
| 12A-t[b] | <pre>             CAACGCU<br>          G         A<br>                      C<br>    uc-aa---GGG      A<br>    ag uu   CCC      G<br>      c  CAA  A      A<br>             CGUGAAC</pre> | 0.9 ± 0.2 | 25 |
| 26A-t[b] | <pre>             CAACGUA<br>       A   G       U<br>     GUC GAAG      A<br>     cag-cuuC      G<br>           A     G<br>          CACGAAC</pre> | 0.4 ± 0.1 | 26 |

TABLE VII-continued

SECONDARY STRUCTURES AND DISSOCIATION CONSTANTS ($K_d$'s)
FOR A REPRESENTATIVE SET OF HIGH-AFFINITY
LIGANDS FROM FAMILY 2.

| LIGAND | STRUCTURE[a] | $K_d$, nM | SEQ ID NO: (PARENT SEQUENCE) |
|---|---|---|---|
| 65A-t[b] | ```
          CUACGUA
       G         A
                 A
aacgcucaaG       U
uuGUGGGUUC       G
       A         A
          CGUGAAC
``` | 0.6 ± 0.04 | 29 |
| 22B-t[b] | ```
           UAACGUA
        G         C
agc-augcugAGG     U
ucg ugCGACUCC     G
         A        G
           CAGAACU
``` | 1 ± 0.6 | 41 |
| 28B-t[b] | ```
         UAACGUA
       G        U
augc-ugAGG
ugUG ACUCC      A
     A    A  G
         CAGAACU
``` | 2 ± 1 | 42 |
| 38B-t[b] | ```
           UAACGCU
       c  G        G
gcaug ugAG         A
ugUAC GCUC         G
      A    A   U
           CGUGAAC
``` | 4 ± 1 | 45 |
| 2B-t[b] | ```
           UAACGCA
       C  G        C
AGC GCAG           C
ucg ugUU           G
      a   A    G
           CCAGAGC
``` | 170 ± 80 | 31 |

[a]Strongly conserved positions are shown in boldface symbols. Nucleotides in the constant region are in lowercase type.
[b]The letter "t" is used to designate truncated sequences derived from the corresponding patent sequences (FIG. XVIII).

TABLE VIII

2'-NH2RNA LIGANDS TO bFGFa.
5'-GGGAGACAAGAAUAACGCUCAA [-30N-] UUCGACAGGAGGCUCACAACAGGC-3' (SEQ ID NO:95)
5'-GGGAGGACGAUGCGG [-50N-] CAGACGACTCGCCCGA-3' (SEQ ID NO:98)

| | | CORRESPONDING CLONE | SEQ ID NO: |
|---|---|---|---|
| FAMILY 1A | | | |
| 14A | ACANGGAGUUGUGUGGAAGGCAGGGGGAGG | 30N | 101 |
| 15A | UGUGUGGAAGGCAGUGGGAGGUUCAGUGGU | 30N | 102 |
| 17A | AAAGUUGUGUGGAAGACAGUGGGAGGUGAA | 30N | 103 |
| 21A | GUAGACUAAUGUGUGGAAGACAGCGGGUGG | 30N | 104 |
| 29A | NNAGUUGUGUGGAAGACAGUGGGGGGUUGA | 30N | 105 |
| 38A | GGUGUGUNGAAGACAGUGGGUNGUUUAGNC | 30N | 106 |
| 49A | AUGGUGUGUGGAAGACAGUGGGUGGUUGCA | 30N | 107 |
| 54A | ACUGUUGUGUGGAAGACAGCGGGUGGUUGA | 30N | 108 |

TABLE VIII-continued

2'-NH2RNA LIGANDS TO bFGFa.
5'-GGGAGACAAGAAUAACGCUCAA [-3ON-] UUCGACAGGAGGCUCACAACAGGC-3' (SEQ ID NO:95)
5'-GGGAGGACGAUGCGG [-5ON-] CAGACGACUCGCCCGA-3' (SEQ ID NO:98)

| | | CORRESPONDING CLONE | SEQ ID NO: |
|---|---|---|---|
| 60A | AAUGUAGGCUGUGUGGUAGACAGUGGGUGG | 30N | 109 |
| 68A | GAUGUGUGGAGGGCAGUGGGGGGUACCAUA | 30N | 110 |
| 74A | GGGGUCAAGGACAGUGGGUGGUGGUGUGU | 30N | 111 |
| 16B | UGCUGCGGUGCGCAUGUGUGGAAGACAGAGGGAGGUUAGAAUCAUGACGU | 50N | 112 |
| 31B | ACAGACCGUGUGUGGAAGACAGUGGGAGGUUAUUAACGUAGUGAUGGCGC | 50N | 113 |
| 38B | GCUGCGGUGCGCAUGUGUGGAAGACAGAGGGAGGUUAGAAUCGUGCCGC | 50N | 114 |
| 39B | GAAAACUACGGUGUGUGGAAGACAGUGGGAGGUUGGCAGUCUGUGUCCGU | 50N | 115 |
| 62B | UCCAUCGUGGAAGACAGUGGGAGGUUAGAAUCAUGACGUCAGACGACUC | 50N | 116 |
| 79B | UGUGAUUUGUGUGGAAGGCAGUGGGAGGUGUCGAUGUAGAUCUGGCGAUG | 50N | 117 |
| | UGUGUGGAAGACAGUGGGWGGUU | ★ | 118 |
| FAMILY 1B | | | |
| 59A | UGUGUGGAAGGGUACCUGAGU----GGGGAUGGG | 30N | 119 |
| 82A | AAGACUGUGUGGAAGGGG---UGUA-----GGGGUUGGG | 30N | 120 |
| 3B | UAGGGCCGCAACUGUGUGGAAGGGAGGAUGCGUCAUGGGGGUUGGGCUG | 50N | 121 |
| | UGUGUGGAAGGGNNNNUGNGU----GGGGUUGGG | ★ | 122 |
| FAMILY 1C | | | |
| 1B | AUUGUGUGGGAUAG-GGCAUAGA-GGGUGU- GGGAAACCCCAGACCGGGGCGU | 50N | 123 |
| 43B | UGUGUGGGACAGCGG-AUC -AGGGGUGU-GGGAGCGCAUAACAUCCUACNUGCU | 50N | 124 |
| 30B | ANNNNUNUGCAUGUGUGGGACAG-GGUGCAUGUGGGUUGCGGGACCUUGGU | 50N | 125 |
| | UGUGUGGGACAG-GGNAUANANGGGUGU-GGGA | ★ | 126 |
| FAMILY 2 | | | |
| 51A | GCAGGAGGAUAGGGAUCGGAUGGGGUAGGA | 30N | 127 |
| 53A | UGAGGAUCGGAUGGGGAGCAGGCGGAGGAA | 30N | 128 |
| 67A | GUGGAUUGGAAGGGGUGCUGGAGGAGGACG | 30N | 129 |
| 15B | UAGGAAUGGAUGGGGUUGGAACAGAGUUCUAAUGUCGACCUCACAUGUGG | 50N | 130 |
| 77B | CAGGAAUGGAUGGGGUUGGAACAGAGUUCUAAUGUCGACCUCACAUGCGU | 50N | 131 |
| 48B | CAGGAUAGGAUGGGGUCGGAACCGUGUAUCAUAACGAGUCAUCUCCUGGU | 50N | 132 |
| | GGAUHGGAUGGGGU | ★ | 133 |
| FAMILY 3 | | | |
| 58A | UUAACGGCGUGGUCCGAGGGUGGCGAGUAC | 30N | 134 |
| 64A | GACUAGGCGCGGACCGUGGGUGGUGAGUGG | 30N | 135 |
| 50B | AGUGGCAUGGGCCGUGGGAGGUGAGUGUCGAGACUGGUGUUGGGCCU | 50N | 136 |
| 22B | CGUGGUUCCGUGGGUGGUGAGAUGAGACUUAAUCAGUUCGUAGACCGGU | 50N | 137 |
| | CCGUGGGUGGUGAGU | ★ | 138 |
| TWO-MEMBER FAMILIES | | | |
| 35B | NAAAUACGAGAGAGGANCAUANNUGACUGAACAUUGAUGUAUUAACGAGU | 50N | 139 |
| 49B | GAGGUACGAGAGAGGAGCGUAGGUGACUGAACAUUGAUGUAUUAACGUGU | 50N | 140 |
| 47B | AGGGUGGCUGGGAGGACCCGCGGUGAAUCGGUAGCACAGUGAUGUUCGGU | 50N | 141 |
| 73B | GAGGGUGGCAGGGAGGACCCGCGGUGAAUCGGUAGCACAGUGAGUUCGGU | 50N | 142 |

TABLE VIII-continued

2'-NH2RNA LIGANDS TO bFGFa.
5'-GGGAGACAAGAAUAACGCUCAA [-30N-] UUCGACAGGAGGCUCACAACAGGC-3' (SEQ ID NO:95)
5'-GGGAGGACGAUGCGG [-50N-] CAGACGACTCGCCCGA-3' (SEQ ID NO:98)

| | | CORRESPONDING CLONE | SEQ ID NO: |
|---|---|---|---|
| 6A | CGCGAGGGCUGGCGGGGUAGGAUGGGUAGA | 30N | 143 |
| 75B | CGCGAGUGCUACGAGGCGUGGGGGGUGGAAACUAGUUGUGCUCUGGCCG | 50N | 144 |
| 55A | GAUUGGAAGCAGGGUGUGGGUUAGGAGGGC | 30N | 145 |
| 21B | GACCACAGUUUAAACGCCCAUCAGUGGUAGGGUGUGGGUAAGGAGGGCUG | 50N | 146 |
| OTHER SEQUENCES | | | |
| 6A | CGCGAGGGCUGGCGGGGUAGGAUGGGUAGA | 30N | 147 |
| 9A | UGGGCCGCCGGUCUUGGGUGUAUGUGUGAA | 30N | 148 |
| 52A | AGUUGGGGCUCGUGCGGCGUGGGGCGUGC | 30N | 149 |
| 62A | GGGAUGGUUGGAGACCGGAGAUGGGAGGA | 30N | 150 |
| 69A | AAACGGGGCGAUGGAAAGUGUGGGGUACGA | 30N | 151 |
| 73A | GAGGAGGAUGGAGAGGAGCGGUGUGCAGGG | 30N | 152 |
| 83A | GAGAGGGUGAAGUGGGCAGGAUGGGGUAGG | 30N | 153 |
| 8B | CUGAAAUUGCGGGUGUGGAGGUAUGCUGGGAAAGGUGGAUGGUACACGU | 50N | 154 |
| 13B | CAAUGUUUGGAGCUCGCUAAUGUGGGUGGGUUAGACGUACCGAUGGUUGC | 50N | 155 |
| 14B | ACGGGGAAGUACGAGAGCGGACUGUAAGUCUAGUGGGUCAGUUCGGUG | 50N | 156 |
| 19B | UUCAGCGCGCAUUAGUGCAGCGGGUUCAACAAAAGAGGUGUUCGUGUGUG | 50N | 157 |
| 26B | CGGAUUGUGUGGUCGGGAGGGCAGUAGUUUACACUCACCCGUGGUCUGCU | 50N | 158 |
| 29B | GGUGUGUGACAAUGUGCGUGGGUUGGGCAGGUACAAAGCGUAUGGGCGUG | 50N | 159 |
| 34B | AACGGGAGGUACGAGAGCGGGAGCGCAUAAAUAGGAAACUCCUUGCACGU | 50N | 160 |
| 36B | AGGCAGUAUUGGGGGUGGUCAGCGCCUCCCCAAAACUCGCACCUUAGCCC | 50N | 161 |
| 44B | GGGUUGGGUGGCAAGCGGAGAGCAGGGUUAGGUGCGGACUCAUUGGUGUG | 50N | 162 |
| 52B | GGAGGGGCAGGUUCGAUGCGGGAGCGACUGACCACGAGAAAUGUGCGGGU | 50N | 163 |
| 72B | CUCAGCAUCCAGGAAGGGGACUUGGUAGGGCACCAUCGAGAUCUUGGCGU | 50N | 164 |
| 78B | ACCCUAGGCAUCCAGGUUGGGGAUAGCGGUUGGAGUGAAUGUGUUGUGCC | 50N | 165 |
| NITROCELLULOSE-BINDING FAMILY | | | |
| 5A | CACGGAGGAGGAGGUCAGACUUAGCGGUCA | 30N | 166 |
| 16A | UACAGGGGAAGGAGNGAAUUGCAAGAUGAA | 30N | 167 |
| 17A* | AAAGUUGUGUGGAAGACAGUGGGAGGUGAA | 30N | 168 |
| 19A | UGAUGGCGGUAGUGGAGGUAAUGAGCGUNA | 30N | 169 |
| 25A | UAGGAGGUUGGAGGAAAGCUUCACAGCCGA | 30N | 170 |
| 40A | UGAGGAGGAGGAGGACAGGAUUCAACGAGU | 30N | 171 |
| 65A | GUUAGGAGGGUGGAGGUUCGAGUGUGGCAA | 30N | 172 |
| 66A | CGUCGAGUGCGAUGGAGGAGGAGGGAUGCA | 30N | 173 |
| 74A* | GGGGUCAAGGACAGUGGGUGGUGGUGGUGU | 30N | 174 |
| 75A | GGAGGGAGGAGGGAUGAUGAGCUCAUCAGC | 30N | 175 |
| 76A | CAAACAGGAGGGAAUGGAGGGNG | 30N | 176 |
| 77A | AGGGGUGGUCGGUAAGCUCGGUGGUGGUGG | 30N | 177 |

TABLE VIII-continued

2'-NH2RNA LIGANDS TO bFGFa.
5'-GGGAGACAAGAAUAACGCUCAA [-30N-] UUCGACAGGAGGCUCACAACAGGC-3' (SEQ ID NO:95)
5'-GGGAGGACGAUGCGG [-50N-] CAGACGACTCGCCCGA-3' (SEQ ID NO:98)

| | | CORRESPONDING CLONE | SEQ ID NO: |
|---|---|---|---|
| 78A | AGGAGGGUUAAGGAGGGAGAUUAAGCGUUGG | 30N | 178 |
| 81A | GUGGAGGGUACGUGGAGGGGAGAGCGACA | 30N | 179 |
| 85A | AUAAUUCAAGGAGGUGGAGGACAGAUGCGC | 30N | 180 |
| 86A | GAUGAGGACUCGGGCGGAGGGUGGUACCA | 30N | 181 |
| 5B | AGGUCGUGGCUGGGAUUCGUCCUCGACAUGUACAUUGUGGCUCUGGUGCC | 50N | 182 |
| 6B | AAGUUAGUCAUCGUGCAAACUGCGAGUGCACUGCUCGGGAUCC | 50N | 183 |
| 21B | GACCACAGUUUAAACGCCCAUCAGUGGUAGGGUGUGGGUAAGGAGGGCUG | 50N | 184 |
| 75B | CGCGAGUGCUACGAGGCGUGGGGGGGUGGAAACUAGUUGUGCUCUGGCCG | 50N | 185 |

★ CONSENSUS SEQUENCE
[a] NUCLEOTIDE ABBREVIATIONS C AND U ACTUALLY DEPICT THE MODIFIED NUCLEOTIDES 2'-NH$_2$-C AND 2'-NH$_2$-U.

TABLE IX

DISSOCIATION CONSTANTS FOR A REPRESENTATIVE SET OF HIGH-AFFINITY 2'-NH$_2$ RNA LIGANDS TO bFGF.

| CLONE | Kd (nM) | SEQ ID. NO: |
|---|---|---|
| 21A | 1.3 ± 0.1 | 104 |
| 49A | 1.4 ± 0.3 | 107 |
| 53A | 1.5 ± 0.3 | 128 |
| 54A | 1.7 ± 0.3 | 108 |
| 58A | 1.4 ± 0.3 | 134 |
| 59A | 1.2 ± 0.2 | 119 |
| 22B | 2.8 ± 0.5 | 137 |
| 34B | 2.0 ± 0.4 | 160 |
| 47B | 2.9 ± 0.3 | 141 |
| 48B | 6.7 ± 1.1 | 132 |
| 52B | 2.3 ± 0.3 | 163 |
| 72B | 3.4 ± 0.5 | 164 | starting random RNA A 65 ± 11
starting random RNA B 240 ± 140

TABLE X

INHIBITION OF RAT CORNEAL VASCULAR INGROWTH BY RNA LIGAND 21A.

| Day | Group I (untreated) | Group II 21A | Group III (bFGF) | Group IV (21A + bFGF) |
|---|---|---|---|---|
| 7 | 367 ± 4 | 363 ± 3 | 972 ± 72 | 623 ± 122* |
| 14 | 470 ± 57 | 388 ± 11 | 1528 ± 167 | 900 ± 80* |

Data are mean ± STD. Err.
*$P < 0.05$ compared with Group III. (T-test, 2 Tailed)

TABLE XI

OLIGONUCLEOTIDES USED IN SELEX EXPERIMENTS A AND B TO SELECT 2'-NH$_2$ PYRIMIDINE RNA LIGANDS TO bFGF.

| | | SEQ ID NO. |
|---|---|---|
| SELEX EXPERIMENT A | | |
| Starting RNA* | 5'-GGGAGACAAGAAUAACGCUCAA[-30N-]UUCGACAGGAGGCUCACAACAGGC-3' | SEQ ID NO:95 |
| PCR Primer 1 | 5'-<u>TAATACGACTCACTATA</u>GGGAGACAAGAAUAACGCUCAA-3'<br>T7 Promoter | SEQ ID NO:96 |
| PCR Primer 2 | 5'-GCCTGTTGTGAGCCTCCTGTCGAA-3' | SEQ ID NO:97 |
| SELEX EXPERIMENT B | | |
| Starting RNA* | 5'-GGGAGGACGAUGCGG[-50N-]CAGACGACTCGCCCGA-3' | SEQ ID NO:98 |

TABLE XI-continued

OLIGONUCLEOTIDES USED IN SELEX EXPERIMENTS A AND B TO SELECT 2'-NH₂ PYRIMIDINE RNA LIGANDS TO bFGF.

| | | SEQ ID NO. |
|---|---|---|
| PCR Primer 1 | 5'-<u>TAATACGACTCACTATA</u>GGGAGGACGAUGCGG-3'<br>       T7 Promoter | SEQ ID NO:99 |
| PCR Primer 2 | 5'-TCGGGCGAGTCGTCTG-3' | SEQ ID NO:100 |

*In the randomized region; [-30N-] or [-50N-]; each pyrimidine contains an amino (—NH₂) functionality at the 2'-position.

TABLE XII

THROMBIN RNA BINDING SEQUENCES

| | 1 | 2 | 3 | SEQ ID NO: |
|---|---|---|---|---|
| CLASS I | | | | |
| #1 | AGAUGCCUGUCGAGCAUGCUG | AGGAUCGAAGUU<u>AGUAGG</u>CUUUGUGUGCUC | GUAGCUAAACAGCUUUGUCGACGGG | 192 |
| #6 | AGAUGCCUGUCGAGCAUGCUG | AGGAUCGAAGUU<u>AGUAGG</u>CUUUGUGUGCUC | GUAGCUAAACAGCUUUGUCGACGGG | 192 |
| #13 | AGAUGCCUGUCGAGCAUGCUG | AGGAUCGAAGUU<u>AGUAGG</u>CUUUGUGUGCUC | GUAGCUAAACAGCUUUGUCGACGGG | 192 |
| #19 | AGAUGCCUGUCGAGCAUGCUG | AGGAUCGAAGUU<u>AGUAGG</u>CUUUGUGUGCUC | GUAGCUAAACAGCUUUGUCGACGGG | 192 |
| #23 | AGAUGCCUGUCGAGCAUGCUG | AGGAUCGAAGUU<u>AGUAGG</u>CUUUGUGUGCUC | GUAGCUAAACAGCUUUGUCGACGGG | 192 |
| #24 | AGAUGCCUGUCGAGCAUGCUG | AGGAUCGAAGUU<u>AGUAGG</u>CUUUGUGUGCUC | GUAGCUMACAGCUUUGUCGACGGG | 192 |
| #25 | AGAUGCCUGUCGAGCAUGCUG | AGGAUCGAAGUU<u>AGUAGG</u>CUUUGUGUGCUC | GUAGCUAAACAGCUUUGUCGACGGG | 192 |
| #30 | AGAUGCCUGUCGAGCAUGCUG | AGGAUCGAAGUU<u>AGUAGG</u>CUUUGUGUGCUC | GUAGCUAAACAGCUUUGUCGACGGG | 192 |
| #2 | AGAUGCCUGUCGAGCAUGCUG | UACU<u>GGAUCGAAGG</u>U<u>AGUAGG</u>CAGUCAC | GUAGCUAAACAGCUUUGUCGACGGG | 193 |
| #5 | AGAUGCCUGUCGAGCAUGCUG | AUAUCAC<u>GGAUCGAAGG</u>A<u>AGUAGG</u>CGUG | GUAGCUAAACAGCUUUGUCGACGGG | 194 |
| #9 | AGAUGCCUGUCGAGCAUGCUG | CCUUUCCC<u>GGGUUCGAAG</u>UC<u>AGUAGG</u>CCGG | GUAGCUAAACAGCUUUGUCGACGGG | 195 |
| #10 | AGAUGCCUGUCGAGCAUGCUG | CACCC<u>GGAUCGAAG</u>UU<u>AGUAGG</u>CGUGAGU | GUAGCUAAACAGCUUUGUCGACGGG | 196 |
| #15 | AGAUGCCUGUCGAGCAUGCUG | UGUAC<u>GGAUCGAAGG</u>U<u>AGUAGG</u>CAGGUUAC | GUAGCUAAACAGCUUUGUCGACGGG | 197 |
| #16 | AGAUGCCUGUCGAGCAUGCUG | CAUCC<u>GGAUCGAAG</u>UU<u>AGUAGG</u>CCGAGGUG | GUAGCUAAACAGCUUUGUCGACGGG | 198 |
| #18 | AGAUGCCUGUCGAGCAUGCUG | AUUGUUGC<u>GGAUCGAAG</u>UG<u>AGUAGG</u>CGCUA | GUAGCUAAACAGCUUUGUCGACGGG | 199 |
| #21 | AGAUGCCUGUCGAGCAUGCUG | UGUACU<u>GGAUCGAAGG</u>U<u>AGUAGG</u>CAGUCAC | GUAGCUAAACAGCUUUGUCGACGGG | 200 |
| #22 | AGAUGCCUGUCGAGCAUGCUG | <u>AUCGAAG</u>UU<u>AGUAGG</u>AGCGUGUG | GUAGCUAAACAGCUUUGUCGACGGG | 201 |
| #26 | AGAUGCCUGUCGAGCAUGCUG | ACGCUGGAGUC<u>GGAUCGAAAGG</u>UA<u>AGUAGG</u>CGACU | GUAGCUAAACAGCUUUGUCGACGGG | 202 |
| #31 | AGAUGCCUGUCGAGCAUGCUG | GGGUC<u>GGAUCGAAAGG</u>UA<u>AGUAGG</u>CGACU | GUAGCUAAACAGCUUUGUCGACGGG | 203 |
| #33 | AGAUGCCUGUCGAGCAUGCUG | AUAUCA<u>CGGAUCGAAAGA</u><u>AGUAGG</u>CGU | GUAGCUAAACAGCUUUGUCGACGGG | 204 |
| #34 | AGAUGCCUGUCGAGCAUGCUG | UGUAC<u>UGGAUCGAAGG</u>U<u>AGUAGG</u>CAGGCAC | GUAGCUAAACAGCUUUGUCGACGGG | 205 |
| #37 | AGAUGCCUGUCGDGCAUGCUG | AUAUCA<u>CGGAUCGAAGG</u>AA<u>AGUAGG</u>CGUG | GUAGCUAAACAGCUUUGUCGACGGG | 206 |
| CLASS II | | | | |
| #3 | AGAUGCCUGUICGAGCAUGCUG | GU<u>GCGGCUUUGGGCGCCGUGCUU</u>GGC | GUAGCUAAACAGCUUUGUCGACGGG | 207 |
| #20 | AGAUGCCUGUCGAGCAUGCUG | GU<u>GCGGCUUUGGGCGCCGUGCUU</u>AC | GUAGCUAAACAGCUUUGUCGACGGG | 208 |
| #27 | AGAUGCCUGUCGAGCAUGCUG | GU<u>GCGGCUUUGGGCGCCGUGCUU</u>GAC | GUAGCUAAACAGCUUUGUCGACGGG | 209 |
| #35 | AGAUGCCUGUCGAGCAUGCUG | GGG<u>CGGCUUUGGGCGCCGUGCUU</u>GAC | GUAGCUAAACAGCUUUGUCGACGGG | 210 |

TABLE XII-continued

THROMBIN RNA BINDING SEQUENCES

| | SEQ ID NO: |
|---|---|
| #38 AGAUGCCUGUCGAGCAUGCUG GU<u>GCGGCUUUGGGCGCCGUGCUUG</u>AC GUAGCUAAACAGCUUUGUCGACGGG | 209 |
| #39 AGAUGCCUGUCGAGCAUGCUG GU<u>GCGGCUUUGGGCGCCGUGCUU</u>GAC GUAGCUAAACAGCUUUGUCGACGGG | 209 |

★THE CONSERVED SEQUENCE MOTIFS WITHIN THE 30N VARIABLE REGION ARE UNDERLINED.

TABLE XIII

LIGANDS USED IN BOUNDARY EXPERIMENTS

| CLONE* | RANDOM REGION | SEQ ID NO: |
|---|---|---|
| CLASS I | | |
| 6 | gggagaugccuguc[g[agcaugcug AGGAUCGAAGUUAGUAGGCUUUGUGUGCU]C guagcuaaacagcuuugucgacggg | 211 |
| 16 | gggagaugccugucgagcau[gcug C[AU[CCGGAUCGAAGUUAGUAGGCCGAG]GUG guagcuaaacagcuuugucgacggg | 212 |
| 18 | gggagaugccugucgagcaugcug AUUGU[UGCGGAUCGAAGUGAGUAGGCGCUA] guagcuaaacagcuuugucgacggg | 213 |
| CLASS II | | |
| 27 | gggagaugccuguc[g[agcaugcug GUGCGGCUUUGGGCGCCGUGCUU]GAC guagcuaaacagcuuugucgacggg | 214 |

*NUCLEOTIDES IN THE CONSTANT REGION ARE IN LOWER CASE TYPE
"[" DENOTES A 5' BOUNDARY AND "]" DENOTES A 3' BOUNDARY
THE PROPOSED 2° STRUCTURES ARE SHOWN IN TABLE XIII.

TABLE XIV

FUNCTIONAL ASSAYS THROMBIN ACTIVITY

A. Peptidase Activity-Cleavage of tripeptide p-nitroaniline substrate (S2238)

H-D-Phe-Pip-Arg-p-Nitroaniline + $H_2O$ $\xrightarrow{\text{Thrombin}}$ H-D-Phe-Pip-Arg-OH + p-Nitroaniline Measure the OD at 405 nM for release of p-Nitroaniline

| | [Thrombin] | [RNA] | Inhibition (decrease in $OD_{405}$) |
|---|---|---|---|
| Class I RNA 16 | $10^{-8}$ M | $10^{-8}$ M | — |
| (SEQ ID NO:198) | $10^{-8}$ M | $10^{-7}$ M | — |
| | $10^{-9}$ M | $10^{-8}$ M | — |
| Class II RNA 27 | $10^{-8}$ M | $10^{-8}$ M | — |
| (SEQ ID NO:209) | $10^{-8}$ M | $10^{-7}$ M | — |
| | $10^{-9}$ M | $10^{-8}$ M | — |

FUNCTIONAL ASSAYS THROMBIN ACTIVITY

B. Fibrinogen Clotting Assay

| Ligand plus purified human thrombin (2.5 nM) | Clotting time (sec) for purified fibrinogen (0.25 mg/ml) |
|---|---|
| No RNA/DNA | 65 |
| Class I RNA 16 (30 nM) | 117 |
| Class II RNA 27 (60 nM) | 115 |
| DNA 15mer G15D (SEQ ID NO:189) | 270–330 |

TABLE XV

HIGH-AFFINITY DNA LIGANDS TO THROMBIN

| | SEQ ID NO: |
|---|---|
| 11TH ROUND 30N SEQUENCES<br>5' AGATGCCTGTCGAGCATGCT(30N)GTAGCTAAACTGCTTTGTCGACGGG | 215 |
| CLONE(30N) | |
| #1    TCACTAGGCTAGGTGTGCATGATGCTAGTG | 216 |
| #2    GTCAGCTACCGTGGTAGGGAAGGTTGGAGT | 217 |

TABLE XV-continued
HIGH-AFFINITY DNA LIGANDS TO THROMBIN

| | | SEQ ID NO: |
|---|---|---|
| #3 | ACTAGCGGGGTAGTGGTGGGTTGGGGTCTA | 218 |
| #6 | ACACCCGTGGTAGGGTAGGATGGGGTGGTC | 219 |
| #7, 23 | GCAGTTGTGCTCGTGGTAGGGTAGGATGGG | 220 |
| #8, 9, 32 | GTGAATAGGTAGGGTCGGATGGGCTACGGT | 221 |
| #10 | GAGTTGAGGGTAGGCGTGGGATGGTGGAAC | 222 |
| #13 | ATGTGCTACCGTGGTAGGGAAGGATGGTGT | 223 |
| #14 | GTTGTGGTAGGGTTAGGGATGGTAGCGGTT | 224 |
| #15, 34 | GTTGGCGGGAGTGGTAGGCAGTAGGGTTGG | 225 |
| #16 | GCCGCTACGAGGGTAGGTGTGGATGCTGCC | 226 |
| #17 | GTTTTGGTATAGGCTAGGTGTGCATGATGCT | 227 |
| #18 | GTTTATCGGTAGGGTTGGTTGGGCTACAAT | 228 |
| #20 | ACGGACCGCGCGACGAACTGTGAAGGGCCG | 229 |
| #21 | GCGTTTAGCTCGGGGTAGTGGTGGGTTGGT | 230 |
| #25 | GAATCAGTTTAGGTGTGGTAGGGCAGGTTG | 231 |
| #26 | TAGCTGCTCGTGGTAGGGTAGGTTGGGGTA | 232 |
| #27 | GCGTAGTGCGCGCGACGAACTGTGAAGCAC | 233 |
| #28 | GTGACTACTCTCACTCCTATGGAACGGTCA | 243 |
| #29 | CGATGCGTGGTAGGGTAGGTTGGTGTCATT | 235 |
| #31 | GGTTATCGGTAGGTGTGGATGGGCTACTTT | 236 |
| #33 | GCGTTTAGTTCGGGGTAGTGGTGGGTTGGA | 237 |
| #35 | GGGAGTGGTAGGAGTAGGGTTGGAGCCGTA | 238 |
| #36 | GTGAATAGGTAGGGTCGGATAGGCTACGGT | 239 |
| 11TH ROUND 60N SEQUENCES | | |
| 5'AGATGCCTGTCGAGCATGCT(60N)GTAGCTAAACTGCTFTGTCGACGGG-3' | | 240 |
| CLONE (60N) | | |
| #1 | GCAAAGCCGGGAAGTCCCAGTGGTAGGCTGAGGGTTGGGGGATTGAAATCCCTGTGGAC | 241 |
| #2 | GACGGGCCAGGGAGGTGGCAGCAGGGATGGGTTAGTGGTAGGCGCTGCAACTCAGGATTG | 242 |
| #3 | AGCTGTCGTCGTGCCGCGTGGTGAGGGTTGATGCGTGGGTAGGCTAGTCCCATGGCGA | 243 |
| #4 | CTGCGGGTGGGACGGAGCGTGGTAGGGCAGGTTGGAGTCGTAGTCTCACGGGCCTGGGCA | 244 |
| #6 | TGGTCGTAGCTGCTAGGTGAAGGTATGGCCGGGGTAGTGGTGGGTTGGGGTGCGATGCAG | 245 |
| #7 | GGCGGCGTTGGTGTAGTGGCGCACTGTGGTTGGGCGGAGAGGCTAGGAGTGCATGATGCC | 246 |
| #8 | AAGGCCTGGAGCCGGTTGGTTGCGGGGGGTAGGCTAGGTGTGCATGATGCTACCCCACG | 247 |
| #9 | CCGTGCATCAACCGTGCGACGCTGGTTTGCTGTGGTAGGGGAGGATGGACCCAGGAGTGG | 248 |
| #10 | AGCCGATGTTGCGGTGGATACTCGGATTGGTAGGGCAGGTTGGGCTCGGATGAGCTCGGA | 249 |
| #11 | TGAGCAGGTGGTAGGGTTAGGGTTGGGTCGCTGAGGCGTCCTGATCACGCGCGGGTGAGG | 250 |
| #12 | GGCAGTGCGTCTTCTGGCAAGGTGTGTGTTGCGGAGAGGGTAGGTGTGGATGATGCCGGA | 251 |
| #13 | CTAGCGGCTGGTAGGGGAGGTTGGGAGTGGTGACTCCCGCTGGGCGTGATTCGTGCAGGG | 252 |
| #14 | CTGCGGGTGGGACGGAGCGTGGTAGGGCAGGTTGGAGTCGTAGTCTCACGGGCCCGGGCA | 253 |
| #15 | GCAGTAGGGAGCACGCGGGCCTAGGGTAGGTGTGGATGATGCGGGCAGGCGGTGCGACTT | 254 |

TABLE XV-continued

HIGH-AFFINITY DNA LIGANDS TO THROMBIN

| | | SEQ ID NO: |
|---|---|---|
| #16 | GGAAGCTGGGGCAGCGTAGGAGTAGGGATGGGCGAGTGGTAGGCGCGGTTCGCTGTGCA | 255 |
| #18 | CTTTGGAGACAGTCCGTGGTAGGGCAGGTTGGGGTGACTTCGTGGAAGAAGCGAGACGGT | 256 |
| #19 | GATGGATAACACGTGGCCGGGGAGCGTGGTAGGGTAGGATGGTGTCGATTGCGCCAGGTG | 257 |
| #20 | CGGAGCCGGGGTAGTGGTGGGATGGGGCGTAGGACATGGCAAGTGCGGTGTAGCCGTGG | 258 |
| #21 | GCAAGCGTTCGGTGTTGAGTGTAGGTAGGTCTTTGGTTGGGTCGTGTCGTCCACTGTTC | 259 |
| #22 | GGCGTCGCAGAGGTAGCGTTGGTAGGGTACGTTGGCTCTGAGGAGCCGCGCCTCGTCCG | 260 |
| #24 | CCTGTGAGGGACGGGGAGGAGTGAGGGTTGGGCGTGAGTCGCAGGGTGGTAGGCCACTCC | 261 |
| #25 | GACGGGTGCAGCGCGGGAGCGTGGTAGGGAAGGTTGGGGTCTTCAGCGCTGTGTTGGGCC | 262 |
| #26 | CAGCAATGAGGGCTGGCGGAGTGTGGTAGGGTAGGTTTGGTGTGGAGGGAGCACGGTGGT | 263 |
| #27, 32 | GGCGTCCGATGATTCAGGTCGTGGTAGGCATTGAGGGATGGGTCCTGTGGGACTGGCCT | 264 |
| #28 | GCAGTAGGGAGCATGCGGGCCTAGGGTAGGTGTGGATGATGCGGGCAGGCGGTGCGACTT | 265 |
| #29 | GATTGCAATCACTCTGGCGGAGTTGGTAGGGGAGGTTGGGCGCGGTAGGGCCGTAGCCAG | 266 |
| #30 | GAGACGTTGGTAGGGGTGGTTGGGCCTCGGTGGAGGTCGTCGAAGGCAGGGGAGTGTCGG | 267 |
| #31 | GGAACCGCGGAGGGCGTAGGGTFGGAGGCGTTGGCCGATGTGGTAGGCACGGACTCGGAT | 268 |
| #33 | TGTTUCGAGTTGGCGGCAGGTGGTAGGATCAGGGATGCGAGCCGAAGAATGTGTCGCCAC | 269 |
| #35 | CGGGTAGTCGGAGGTTCGCGCTAGGCCGTGGTAGGGTAGGTTGGGGCGCCTGAGCGGGCG | 270 |
| #36 | TGCTGTCGGCTGTFCGGACGGGCCTGGTAGGGGAGGTTGGGCATCGTAGGATGTGGCCCG | 271 |

TABLE XVI

STRUCTURE AND DISSOCIATION CONSTANTS (Kd's) FOR A REPRESENTATIVE
SET OF HIGH-AFFINITY DNA LIGANDS TO THROMBIN

| | | 5' | | | 3' | SEQ ID NO: |
|---|---|---|---|---|---|---|
| 30N3 | #6 | AGATGCCTGTCGAGCATGCT | ACACCCGTGGTAGGGTA...GGATGGGGTGGTC | GTAGCTAAACTGCTTTGTCGACGGG | | 272 |
| | #8 | AGATGCCTGTCGAGCATGCT | GTGAATAGTAGGGTC...GGATGGGCTACGGT | GTAGCTAAACTGCTTTGTCGACGGG | | 273 |
| | #16 | AGATGCCTGTCGAGCATGCT | GCCGCTACGAGGGTAGGTGT..GGATGCTGCC | GTAGCTAAACTGCTTTGTCGACGGG | | 274 |
| | #14 | AGATGCCTGTCGAGCATGCT | GTTGTGGTAGGGTTAGGGATGGTAGCGGTT | GTAGCTAAACTGCTTTGTCGACGGG | | 275 |
| | #35 | AGATGCCTGTCGAGCATGCT | GGGAGTGGTAGGAGTAGGGTTGG.AGCCGTA | GTAGCTAAACTGCTTTGTCGACGGG | | 276 |
| 60N3 | #7 | AGATGCCTGTCGAGCATGCT | GGCGGCGTTGGTGTAGTGGCACTGTGTTGGGCGGAGAGGCTAGGAGTGCATGATGCC | GTAGCTAAACTGCTTTGTCGACGGG | | 277 |
| | #18 | AGATGCCTGTCGAGCATGCT | CTTTGGAGA...CAGTCCGTGGTAGG....GCAGGTTGGGGTGACTTCGTGAAGAAGCGAGACGGT | GTAGCTAAACTGCTTTGTCGA | | 278 |
| | #18(38) | | CAGTCCGTGGTAGG....GCAGGTTGGGGTGACTTCGTGGAA | | | 279 |
| | #27 | AGATGCCTGTCGAGCATGCT | GGCGTCCCATGATTCAGGTCGTGTAGGCATTGAGGGATGGGTC..CT..GTGGGACTGGCCT | GTAGCTAAACTGCTTTGTCGACGGG | | 280 |

| Ligand | Kd |
|---|---|
| 30-6 | 1.2 nM |
| 30-8 | 0.4 nM |
| 30-14 | 1.0 nM |
| 30-16 | 9.4 nM |
| 30-35 | 1.4 nM |
| 60-7 | 2.5 nM |
| 60-18 | 0.92 nM |
| 60-18(38) | 1.90 nM |
| 60-27 | 0.96 nM |

TABLE XVII

| | FAMILY 1 RNA LIGANDS TO bFGF. | SEQ ID NO: |
|---|---|---|
| 4A | gggagcucagaauaaacgcucaaUGCUAUUCGCCUAACUCGGCGCUCCUACCUuucgacaugaggcccggauccggc | 281 |
| 5A | gggagcucagaauaaacgcucaaAUCUCCUCCCGUCGAAGCUAACCUGGCCACuucgacaugaggcccggauccggc | 282 |
| 7A | gggagcucagaauaaacgcucaaUCGGCGAGCUAACCAAGACACUCGCUGCACuucgacaugaggcccggauccggc | 283 |
| 10A | gggagcucagaauaaacgcucaaGUAGCACUAUCGGCCUAACCCGGUAGCUCCuucgacaugaggcccggauccggc | 284 |
| 13A | gggagcucagaauaaacgcucaaACCCGCGGCCUCCGAAGCUAACCAGGACACuucgacaugaggcccggauccggc | 285 |
| 14A | gggagcucagaauaaacgcucaaUGGGUGCUAACCAGGACACACCCACGCUGUuucgacaugaggcccggauccggc | 286 |
| 16A | gggagcucagaauaaacgcucaaCACGCACAGCUAACCAAGCCACUGUGCCCCuucgacaugaggcccggauccggc | 287 |
| 18A | gggagcucagaauaaacgcucaaCUGCGUGGUAUAACCACAUGCCCUGGGCGAuucgacaugaggcccggauccggc | 288 |
| 21A | gggagcucagaauaaacgcucaaUGGGUGCUUAACCAGGCCACACCCUGCUGUuucgacaugaggcccggauccggc | 289 |
| 25A | gggagcucagaauaaacgcucaaCUAGGUGCUAUCCAGGACUCUCCCUGGUCCuucgacaugaggcccggauccggc | 290 |
| 29A | gggagcucagaauaaacgcucaaUGCUAUUCGCCUAGCUCGGCGCUCCUACCUuucgacaugaggcccggauccggc | 291 |
| 38A | gggagcucagaauaaacgcucaaAGCUAUUCGCCCAACCCGGCGCUCCCGACCuucgacaugaggcccggauccggc | 292 |
| 39A | gggagcucagaauaaacgcucaaACCAGCUGCGUGCAACCGCACAUGCCUGGuucgacaugaggcccggauccggc | 293 |
| 56A | gggagcucagaauaaacgcucaaCAGGCCCCGUCGUAAGCUAACCUGGACCCUuucgacaugaggcccggauccggc | 294 |
| 61A | gggagcucagaauaaacgcucaaUGGGUGCUAACCACCACACACUCACGCUGUuucgacaugaggcccggauccggc | 295 |

*Arrows indicate the double stranded (stem) regions that flank the conserved loop.
Lower case symbols indicate nucleotides in the constant region.

TABLE XVIII

| | FAMILY 2 RNA LIGANDS TO bFGF. | SEQ ID NO: |
|---|---|---|
| 11A | gggagcucagaauaaacgcucaaGGGUAACGUUGU--GACAAGUACACCUGCGUCuucgacaugaggcccggauccggc | 296 |
| 12A | gggagcucagaauaaacgcucaaGGGGCAACGCUACA-GACAAGUGCACCCAACuucgacaugaggcccggauccggc | 297 |
| 26A | gggagcucagaauaaacgcucaaCGUCAGAAGGCAACGUAUA--GGCAAGCACACuucgacaugaggcccggauccggc | 298 |
| 27A | gggagcucagaauaaacgcucaaCCUCUCGAAGACAACGCUGU--GACAAGA-CACuucgacaugaggcccggauccggc | 299 |
| 47A | gggagcucagaauaaacgcucaaAGUGGGAAACGCUACUUGACAAGA-CACCACuucgacaugaggcccggauccggc | 300 |
| 65A | gggagcucagaauaaacgcucaaGGCUACGCUAAU-GACAAGUGCACUUGGGUGuucgacaugaggcccggauccggc | 301 |
| 1B | gggagaugccugucgagcaugcugCUCUGGUAACGCAAU--GUCAAGUGCACAUGAguagcuaaacagcuuugucgacggg | 302 |
| 2B | gggagaugccugucgagcaugcugAGCCGCAGGUAACGGACC--GGCGAGACCAUUguagcuaaacagcuuugucgacggg | 303 |

TABLE XVIII-continued

| FAMILY 2 RNA LIGANDS TO bFGF. | SEQ ID NO: |
|---|---|
| 6B gggagaugccugucgagcaugcugACGAGCUUCGUAACGCUAUC-GACAAGUGCAguagcuaaacagcuuugucgacggg | 304 |
| 8B gggagaugccugucgagcaugcugAAGGGGAAACGUUGA--GUCCGGUACACCCUGguagcuaaacagcuuugucgacggg | 305 |
| 9B gggagaugccugucgagcaugcugAGGGUAACGUACU--GGCAAGCUCACCUCAGCguagcuaaacagcuuugucgacggg | 306 |
| 11B gggagaugccugucgagcaugcugGAGGUAACGUAC---GACAAGACCACUCCAACUguagcuaaacagcuuugucgacggg | 307 |
| 12B gggagaugccugucgagcaugcugAGGUAACGCUGA--GUCAAGUGCACUCGACAUguagcuaaacagcuuugucgacggg | 308 |
| 13B gggagaugccugucgagcaugcugGGGAAACGCUAUC-GACGAGUGCACCCGGCAguagcuaaacagcuuugucgacggg | 309 |
| 14B gggagaugccugucgagcaugcugCCGAGGGUAACGUUGG--GUCAAGCACACCUCguagcuaaacagcuuugucgacggg | 310 |
| 15B gggagaugccugucgagcaugcugUCGGGGUAACGUAUU--GGCAAGG-CACCCGACguagcuaaacagcuuugucgacggg | 311 |
| 19B gggagaugccugucgagcaugcugGGUAACGCUGUG-GACAAGUGCACCAGCUGCguagcuaaacagcuuugucgacggg | 312 |
| 22B gggagaugccugucgagcaugcugAGGGUAACGUACU--GGCAAGCUCACCUCAGCguagcuaaacagcuuugucgacggg | 313 |
| 28B gggagaugccugucgagcaugcugAGGGUAACGUAUA--GUCAAGA-CACCUCAAGUguagcuaaacagcuuugucgacggg | 314 |
| 29B gggagaugccugucgagcaugcugGGGUAACGCAUU--GGCAAGA-CACCCAGCCCCguagcuaaacagcuuugucgacggg | 315 |
| 36B gggagaugccugucgagcaugcugGAGGAAACGUACC--GUCGAGC-CACUCCAUGCguagcuaaacagcuuugucgacggg | 316 |
| 38B gggagaugccugucgagcaugcugAGGUAACGCUCA--GUCAAGUGCACUCGACAUguagcuaaacagcuuugucgacggg | 317 |
| 48B gggagaugccugucgagcaugcugGGGUAACGUGU---GACAAGAUCACCCAGUUUGguagcuaaacagcuuugucgacggg | 318 |
| 49B gggagaugccugucgagcaugcugCACAGGGCAACGCUGCU-GACAAGUGCACCUguagcuaaacagcuuugucgacggg | 319 |

*Arrows indicate the double stranded (stem) regions that flank the conserved loop.
Lower Case symbols indicate nucleotides in constant region.

TABLE XIX

| OLIGONUCLEOTIDES USED IN SELEX EXPERIMENTS 1, 2 AND 3 TO SELECT DNA LIGANDS TO bFGF | | |
|---|---|---|
| | | SEQ ID NO: |
| EXPERIMENT 1 | | |
| 5p2 | ATCCGCCTGATTAGCGATACT | 321 |
| 40N2 | ATCCGCCTGATTAGCGATACT(40N)ACTTGAGCAAAATCACCTGCAGGGG | 322 |
| 3p2 | TGAACTCGTTTTAGTGGACGTCCCCJJJ | 323 |
| EXPERIMENT 2 | | |
| 5pBH1 | CTACCTACGATCTGACTAGC | 324 |
| 40NBH1 | CTACCTACGATCTGACTAGC(40N)TAGCTTACTCTCATGTATTCC | 325 |
| 3pBH1 | ATCGAATGAGAGTACATAAGGJAJA | 326 |
| EXPERIMENT 3 | | |
| 5p7.1PS | GGGAGGACGATGCGG | 327 |
| 30N7.1PS | GGGAGGACGATGCGG(30N)CAGACGACGACGGGGA | 328 |
| 3p7.1PS | GTCTGCTGCTGCCCCTJAJA | 329 |

J = BIOTIN

TABLE XX

AFFINITY OF DNA LIGANDS TO bFGF AFTER EACH ROUND OF SELEX
Experiment 3 DNA SELEX

| Round | % Bound to bFGF | % Bound to Nitrocellulose (Background) | [bFGF] nM | [DNA] nM | Kd nM |
|---|---|---|---|---|---|
| 0 | 10 | 59 | 500 | 1000 | ~300 nM |
| 1 | 4.8 | 14.5 | 250 | 1000 | |
| 2 | 5.9 | 32.5 | 250 | 1000 | |
| 3 | 5 | 8.9 | 100 | 500 | |
| 4 | 6 | 89 | 100 | 500 | |
| 5 | 1.1 | 19.2 | 33 | 167 | |
| 6 | 2.1 | 9.7 | 50 | 250 | |
| 7 | 2.8 | 3.2 | 33 | 167 | |
| 8 | 1.7 | 5.4 | 20 | 100 | 28 nM |
| 9 | 2.5 | 10.8 | 1 | 5 | |
| 10 | 1.6 | 6.9 | 1 | 5 | 2.5 nM Clone |
| 11 | 1.1 | 7 | 1 | 5 | 4 nM |

TABLE XXI

```
FAMILY 1
ALIGNED SEQUENCE GROUP: 30 SEQS, 0.52 AVG. IDENTITY

EXPERIMENT 1 Sequences                                                                                                                      SEQ ID NO:

D3       *    ATCCGCCTGATTAGCGATACTgtgcgatta  ggggctatgcaaat  ccgactatcagaaggctACTTGAGCAAAATCACCTGCAGGGG                                    330
D10      *    ATCCCCCTGATTAGCGATACTaaggcc     agggctatgcaaat  gcgggcgcctatgccattACTTGAGCAAAATCACCTGCAGGGG                                   331
D12      *    ATCCGCCTGATTAGCGATACTaggcc      agggctatgcaaat  gcgggcgcctatgccattACTTGAGCAAAATCACCTGCAGGGG                                   332
D22           ATCCGCCTGATTAGCGATACTcggc       agggctatgcaaat  gcgggcgcctatgccattGACTTGAGCAAAATCACCTGCAGGGG                                  333
D8            ATCCGCCTGATTAGCGATACTa          ggggctgtgcagac   catgggaccatcggatccgtgctACTTGAGCAAAATCACCTGCAGGGG                             334
D42           ATCCGCCTGATTAGCGATACTa          ggggctgtgcaaa    cggggaccatcggatccgtgctACTTGAGCAAAATCACCTGCAGGGG                              335
D5            ATCCGCCTGATTAGCGATACTgtctctc    ggggctttgcaaaa   atcngtagacgacgaggcagACTTGAGCAAAATCACCTGCAGGGG                                336
D19      *    ATCCCGCCTGATTAGCGATACTcgttgctcata ggggctttgcaaaa tcgtataactctactACTTGAGCAAAATCACCTGCAGGGG                                      337
D36           ATCCGCCTGATTAGCGATACTcaa        ggggctttgcaaaa   tgacaagcctaaagcttgacactACTTGAGCAAAATCACCTGCAGGGG                             338
D43           ATCCGCCTGATTAGCGATACTagt        ggggctatgcaaat   tatcgcctagtggctgatactacACTTGAGCAAAATCACCTGCAGGGG                             339
Consensus                                                                       RGGGCTNTGCAAAN                                             340
Truncation         (D12t2)                    AGGCC AGGGCTATGCAAAT  CCGGGCGCCTATGGCC                                                       341

EXPERIMENT 2 Sequences b22           CTACCTACGATCTGACTA     GCagggctttgtaaac  atgactacgtacactatgcaggcaaTAGCTTACTCTCATGTATTCC                                       342
b26           CTACCTACGATCTGACTAGCta gcgggctttgcaaaa   aacgagtgtgttctacgcaaTAGCTTACTCTCATGTATTCC                                            343
b28           CTACCTACGATCTGACTA     GCagggctttgtaaac  atgactacgtacactatgcaggcaaTAGCTTACTCTCATGTATTCC                                       344
b32           CTACCTACGATCTGACTA     GCagggctttgtaaac  atgactacgtacactatgcaggcaTAGCTTACTCTCATGTATTCC                                        345
b5            CTACCTACGATCTGACTA     GCgggctttgcaaag   actgaaatgaccacgccagtgcTAGCTTACTCTCATGTATTCC                                         346
b7            CTACCTACGATCTGACTA     GCagggctgtgtaaa   tggtgcTAGCTTACTCTCATGTATTCC                                                         347
b13           CTACCTACGATCTGACTA     GCagggctttgtaaa   atgactacgtacactatgcaggTAGCTTACTCTCATGTATTCC                                         348
b14           CTACCTACGATCTGACTAGCgcg gcggggctttggaaaa tcgacatactgactTAGCTTACTCTCATGTATTCC                                                  349
b15           CTACCTACGATCGACTA      GCagggctttgtaaac  atgactacgtacacactgcTAGCTTACTCTCATGTATTCC                                             350
Consensus                                             GCRGGCTNTGYAAAN                                                                      351

EXPERIMENT 3 Sequences

M17              GGGAGGACGATGC   GGgggctttgcaaaa  attgtaaatctacccCAGACGACGACGGGGA                                                            352
M19      *       GGGAGGACGAT     GCGGggctatgtaaat tactgctgtactacgcatCAGACGACGACGGGGA                                                        353
M23      *    GGGAGGACGACGATGCGG   CGggggctctgtaaag tctttcaactaccaCAGACGACGACGGGGA                                                          354
M24              GGGAGGACGATG    CGGgggctctcgcaaag tgaaatcccccactaccgCAGACGACGACGACGGGGA                                                    355
M210             GGGAGGACGATGC   GGggggctctgcaaaa  tttcgttaactacctgCAGACGACGACGACGGGGA                                                      356
M217          GGGAGGACGATGCGGgctacgta cggggctctgtaaaa  ccccgCAGACGACGACGGGA                                                                 357
M222             GGGAGGACGATG    CGGgggctatgcaaat  tttccaaactactgcatCAGACGACGACGGGGA                                                        358
M225     *    GGGAGGACGACGATGCGGggctacgta ccggggctttgtaaaa cccgCAGACGACGACGGGGA                                                             359
M235     *       GGGAGGACGAT     GCGGgggctctgcaaag gacacaggtcctacgcatCAGACGACGACGACGGGGA                                                    360
M236             GGGAGGACGAT     GCGGgggctctgcaaat cctcctcggaggctacgCAGACGACGACGGGGA                                                        361
M242             GGGAGGACGAT     GCGggggctcttgtaaaa tctcatctgagactactgtCAGACGACGACGACGGGGA                                                  362
Consensus                                          SSGGGCTNTGCAAAN                                                                         363
Truncation    (M225t3)    GCGGGCTACCTAC CGGGCTTTGTAAAA CCCCGC                                                                               364
Truncation    (m19t2)   G CGGGGCTATGTAAAT TACTGCTGTACTACCCATC                                                                               365

FAMILY 2
```

TABLE XXI-continued

```
                                                                                                                        SEQ ID NO:

ALIGNED SEQUENCE GROUP: 24 SEQS, 0.42 AVG. IDENTITY

EXPERIMENT 1 Sequences d2                      ATCCGCCTGATTAGCGATACTgcttc  ccgacgagcgtagtcgacacagcccaatgtgatACTTGAGCAAAATCACCTGCAGGGG         366
d14             ATCCGCCTGATTAGCGATACTgaccacgactg  atgcgtcgctcccgatcgcagttaccACTTGAGCAAATCACCTGCAGGGG                       367
d15             ATCCGCCTGATTAGCGATACTgaccacgactg  atgcgtcgctgcctccgaagcaggcagttactcACTTGAGCAAATCACCTGCAGGGG                368
d27         ATCCGCCTGATTAGCGATACTtaacacctgcaacacgactg  atgcgtcgctcccgaagctccgataqcACTTGAGCAAAATCACCTCGCAGGGG                369
d29             ATCCGCCTGATTAGCGATACTgaccacgactg  atgcgtcgctcccgatacgtcttaccACTTGAGCAAAATCACCTGCAGGG                       370
d30         ATCCGCCTGATTAGCGATACTttaacaccctcaactgcaacacgactg atgcgtcgctcccgaagctccgagtcACTTGAGCAAAATCACCTGCAGGGG                 371
d34             ATCCGCCTGATTAGCGATACTgaccacgactg  atgcgtcgctcccgataggcagtcagttccACTTGAGCAAATCACCTGCAGGGG                    372
d37       *     ATCCGCCTGATTAGCGATACTgaccacgactgnatgcgtcgctcccgatag  cagttccccACTTGAGCAAAATCACCTGCAGGGG                  373
d40             ATCCGCCTGATTAGCGATACTgcttc  ccgacgagcgtagtcgacacagcccaatggatACTTGAGCAAAATCACCTGCAGGGG                      374
d44       *     ATCCGCCTGATTAGCGATACTgaccacgactg  atgcgtcgctcccgataggcagttaccACTTGAGCAAATCACCTGCAGGGG                    375
d46       *     ATCCGCCTGATTAGCGATACTaaacacgtctg  ctgcgacccctgtactaa cggtaccagtACTTGAGCAAATCACCTGCAGGGG                 376
d50             ATCCCCCTGATTAGCGATACTggtgctcggggaagaattggctacggaccgcggttacctacACTTGAGCAAATCACCTGCAGGGG                        377
EXPERIMENT 2 Sequences b19    CTACCTACGATCTGACTAGCtgaggcgtt  cctggacagttctgagagTAGCTTACTCTCATGTATTCC                                            378
b23    CTACCTACGATCTGACTAGCtggaggcgtt  cctggacagttctgagagctctccaccaaTAGCTTACTCTCATGTATTCC                               379
b29    CTACCTACGATCTGACTAGCtggaggcgtt  cctggacagttctgagagctctccaccaTAGCTTACTCTCATGTATTCC                                380
b33    CTACCTACGATCTGACTAGCgagaaacttcagtgccaagccatccgttcgacgangtaTAGCTTACTCTCATGTATTCC                                    381
b25    CTACCTACGATCTGACTAGCacgaggag  tttttaacgcacagtgaaagcggttgacttaTAGCTTACTCTCATGTATTCC                                382
b3     CTACCTACGATCTGACTAGCtggaggcgtt  cctggacagttctgagaTAGCTTACTCTCATGTATTCC                                           383
EXPERIMENT 3 Sequences m2           GGGAGGACGATCGGacgatagacgtcgaggaatctttagtgccaCAGACGACGACGGGGA                                              384
m215               GGGAGGACGATGCGGacgagng  cagggcacaaatcggatcctcgtCAGACGACGACGGGGA                                        385
m228                 GGGAGGACGATGCGGgacgaggag  cttagcgccgacaaaccCAGACGACGACGGGGA                                       386
m234    *            GGGAGGACGATGCGGcccgaggag  cttagcgccacagttgtgCAGACGACGACGGGGA                                       387
m237                 GGGAGGACGATGCGGgagggag cttagcgccgcgccagggcaatCAGACGACGACGGGGA                                         388
m250                     GGGAGGACGATGCGGcc  actgtacgactagtcactcctgcttccCAGACGACGACGGGAA                                 389
43 Consensesus                                         CGAGGAR-YTTYARYGCCRCRG                                           390
44 Truncation                                          CGAGGAG-CTTTAGCGCCACAGGTT                                        391
                 (234t2)
FAMILY 3
ALIGNED SEQUENCE GROUP: 18 SEQS, 0.42 AVG. IDENTITY EXPERIMENT 1 Sequences d7       ATCCGCCTGATTAGCGATACTtgagtgactgcatcgtcacctacggtccagtgaatACTTGAGCAAAATCACCTGCAGGGG                                392
d13             ATCCGCCTGATTAGCGATACTgcaaaggcatcggccttgctgcttaaagttcgctgccacatACTTGAGCAAAATCACCTGCAGGGG                   393
d17                    ATCCGCCTGATTAGCGATACTacaaggcaaccggtacataggtcgcttaaactgacacgACTTGAGCAAAATCACCTGCAGGGG                 394
d21             ATCCGCCTGATTAGCGATACTctgactgt  gcgtcacctcgtcgaaaacccagtaaactcaAcTTGAGCAAAATCACCTGCAGGGG                    395
d25             ATCCGCCTGATTAGCGATACTctgactgt  gcgtcacctcggttgaaaacccagtaaactccACTTGAGCAAAATCACCTGCAGGGG                   396
d32             ATCCGCCTGATTAGCGATACTcagcatgcgcaagatctccggcgtatcccgtatcACTTGAGCAAATCACCTGCAGGGG                           397
d41             ATCCGCCTGATTAGCGATACTgcaaaggcacttgccgttaatggttcgctgccacatACTTGAGCAAAATCACCTGCAGGGG                        398
EXPERIMENT 2 Sequences b18                                                CTACCTACGATCTGACTAGCtactaccacatgtcgcaggcttccgcagcaactggtcgtTAGCTTACTTACTCTCATGTATTCC                                399
b31    CTACCTACGATCTGACTAGCctcactgactgcgtcgcgtcacgccgactgaaagtccagttTAGCTTACTCTCATGTATTCC                               400
```

TABLE XXI-continued

| | | | SEQ ID NO: |
|---|---|---|---|
| b35 | | CTACCTACGATCTGACTAGCcaactctgggaacacccagcaagtccctcgctcacttgTAGCTTACTCTCATGTATTCC | 401 |
| b1 | | CTACCTACGATCTGACTAGCactgcacaccgttatggaggcTAGCTTACTCTCATGTATTCC | 402 |
| b16 | | CTACCTACGATCTGACTAGCactgagtacccagatgccctcggccgctgaatcggaccaTAGCTTACTCTCATGTATTCC | 403 |
| EXPERIMENT 3 Sequences | | | |
| m202 | | GGGAGGACGATGCGGtcccgcggtataaggcctaggttcgttacCAGACGACGACGCGGGA | 404 |
| m203 | | GGGAGGACGATGCGGcctcggcggtttcttgcacttcagtcaaCAGACGACGACGCGGGA | 405 |
| m208 | | GGGAGGACGATGCGccgcggttgggacgtagggcacaacacatcCAGACGACGACGCGGGA | 406 |
| m219 | | GGGAGGACGATGCGGcgacgcggtacaaggcataggtaCAGACGACGACGCGGGA | 407 |
| m227 | * | GGGAGGACGATGCGGcgcacagtccacgtccaaggcctggtcCAGACGACGACGCGGGA | 408 |
| n233 | | GGGAGGACGATGCGGcaggcgcgttgttacaagtcggactccctcCAGACGACGACGACGGGGA | 409 |
| FAMILY 4 | | | |
| ALIGNED SEQUENCE GROUP: 13 SEQS, 0.47 AVG. IDENTITY | | | |
| EXPERIMENT 1 Sequences | | | |
| d33 | | ATCCGCCTGATTAGCGATACTtgagcaactcgcagttccacgcagatcgctaatccccACTTGAGCAAAATCACCTGCAGGGG | 410 |
| d49 | | ATCCGCCTGATTAGCGATACTagagcaactcggcagttccacgcagatcgctaatccccACTTGAGCAAAATCACCTGCAGGGG | 411 |
| EXPERIMENT 2 Sequences | | | |
| b17 | | CTACCTACGATCTGACTAGCaacgagtgtaacacctaccatgcaggtgccgccaaacagTAGCTTACTCTCATGTATTCC | 412 |
| b20 | | CTACCTACGATCTGACTAGCatacctgaccataagtccgaagat ctcgagtacgtatTAGCTTACTCTCATGTATTCC | 413 |
| b8 | | CTACCTACGATCTGACTAGCcacctgcatagagtaccgactccgattgtatgtTAGCTTACTCTCATGTATTCC | 414 |
| b10 | | CTACCTACGATCTGACTAGCcacctgcatagagtaccgactccgattgtatgtcaccTAGCTTACTCTCATGTATTCC | 415 |
| EXPERIMENT 3 Sequences | | | |
| m15 | | GGGAGGACGATGCGGaggactcgtaccgcacggtgacactctggCAGACGACGACGGGGA | 416 |
| m29 | | GGGAGGACGATGCGGccagctagcggaaggaagtctcgacgaacatCAGACGACGACGGGGA | 417 |
| m221 | | GGGAGGACGATGCGccagctagcggaaggaagtctcgacgaacatCAGACGACGACGGGGA | 418 |
| m48 | | GGGAGGACGATGCGGggggagcggagacacacccggaatatcaaCAGACGACGACGGGGA | 419 |
| m247 | | GGGAGGACGATGCGGCcagttgggagtcaaggggttttgtcgaCAGACGACGACGGGGA | 421 |
| m249 | | GGGAGGACGATGCGGccagtcagccggcggaagggaa tct gacgaacatCAGACGACGACGGGGA | 422 |
| FAMILY 5 | | | |
| ALIGNED SEQUENCE GROUP: 10 SEQS, 0.42 AVG. IDENTITY | | | |
| EXPERIMENT 1 Sequences | | | |
| d1 | * | ATCCGCCTGATTAGCGATACTacaccaaccccctaagatttagagcaactcggcgcaacACTTGAGCAAAATCACCTGCAGGGG | 423 |
| d9 | * | ATCCGCCTGATTAGCGATACTcgaaagatagaagcgatccgctccgtcctgtcacgtcacatagaACTTGAGCAAAATCACCTGCAGGGG | 424 |
| d28 | | ATCCGCCTGATTAGCGATACTacaccaaccccctaagatttagagcaactcggccgcaacACTTGAGCAAAATCACCTGCAGGGG | 425 |
| EXPERIMENT 2 Sequences | | | |
| b34 | | CTACCTACGATCTGACTAGCcaccgaaagttggatgaggtaggtcaaggtgcggtatccTAGCTTACTCTCATGTATTCC | 426 |
| b2 | * | CTACCTACGATCTGACTAGCgaccgactagtccaaaaggtcatagtaccgtgtcagtcTAGCTTACTCTCATGTATTCC | 427 |
| EXPERIMENT 3 Sequences | | | |
| m28 | | GGGAGGACGATGCGGacacggctagtcggagagagattcacttccgcccCAGACGACGACGGGA | 428 |
| m207 | | GGGAGGACGATGCGGcaggcgacctatataggtggtatccccgtaCAGACGACGACGGGGA | 429 |
| m224 | * | GGGAGGACGATGCCGcaccgagaataactgacgccaggctggcgCAGACGACGACGGGGA | 430 |
| m246 | | GGGAGGACGATGCGGcctcagcgatttctggcagtgagtaggagcgCAGACGACGACGGGGA | 431 |

TABLE XXI-continued

ORPHAN SEQUENCES: (46)
EXPERIMINET 1 Sequences

| | | SEQ ID NO: |
|---|---|---|
| d20 | ATCCGCCTGATTAGCGATACTaaggcaaacaacgtgaccgaggcgtagagggtggtcctagcACTTGAGCAAAATCACCTGCAGGGG | 432 |
| d31 | * ATCCGCCTGATTAGCGATACTacatgacgatccgccgatgggtgggtttcaagtccgACTTGAGCAAAATCACCTGCAGGGG | 433 |

EXPERIMENT 2 Sequences

| b4 | CTACCTACGATCTGACTAGCagctagtgcacttcgagtaaccgagtggttgggaatcaagtTAGCTTACTCTCCATGTATTCC | 434 |
| b24 | CTACCTACGATCTGACTAGCcctctagagtcgacctcgaggcatgcaagcttaccactatgcgTAGCTTACTCTCCATGTATTCC | 435 |

EXPERIMENT 3 Sequences

| m26 | GGGAGGACGATGCGGGGGGCTATGCGATACAGTCGCGATACAGTCCGCNTANGCTAGGCGCAGAGCGGGA | 436 |
| m204 | GGGAGGACGATGCGGgcctngatgcagcgtcgtaggcnaancccgaaagccnCAGACGACGACGGGGA | 437 |
| m206 | * GGGAGGACGATGCCGaactggtggctgcttatgtcccccatCAGACGACGACGGGGA | 438 |
| m209 | GGGAGGACGATGCGGgaggctgggtacatctcthagcaagcatCAGACGACGACGACGGGGA | 439 |
| m232 | GGGAGGACGATGCGGgcctgtgcctgtgcttatgtcctccacatCAGACGACGACGGGGA | 440 |
| m240 | GGGAGGACGATGCGGctactgtactgcttatgtctgtcccccgtCAGACGACGACGGGGA | 441 |
| m241 | GGGAGGACGATGCGGgggagtcaatcaccgcaccccactcctcgtCAGACGACGACGACGGGGA | 442 |

*Molecules tested for affinity to bFGF

TABLE XXII

| ISOLATES AND TRUNCATES WITH THE HIGHEST AFFINITY FOR BFGF | | |
|---|---|---|
| Ligand | $K_d$ nM | SEQ ID NO: |
| M17 | 6.9 | 352 |
| M19 | 0.3 | 353 |
| m26 | 1.6 | 436 |
| m206 | 1.8 | 438 |
| m224 | 1.5 | 430 |
| M225 | 0.1 | 359 |
| m234 | 0.7 | 387 |
| M235 | 0.2 | 360 |
| D12 | 0.3 | 432 |
| D19 | 0.1 | 437 |
| D3 | 0.3 | 430 |
| D10 | 0.3 | 431 |

| Truncations | | $K_d$ nM | SEQ ID NO: |
|---|---|---|---|
| M225T3 | GCGGGGCTACGTACCGGGGCTTTGTAAAACCCCGC | 0.7 | 364 |
| M19T2 | GCGGGGCTATGTAAATTACTGCTGTACTACGCATC | 1 | 365 |
| M235T2 | GCGGGGCTCTGCAAAGGACACAGGTCCTACGCATCAG | 1 | 420 |
| D12T2 | AGGCCAGGGCTATGCAAATCGCGGCGCCTATGGCC | 1 | 341 |
| m234T2 | CGAGGAGCTTTAGCGCCACAGGTT | 6 | 391 |
| M225t3GC | GGCGGGGCTACGTACCGGGGCTTTGTAAAACCCCGCC | 0.2 | 443 |

---

SEQUENCE LISTING (1) GENERAL INFORMATION:

(iii) NUMBER OF SEQUENCES: 445

(2) INFORMATION FOR SEQ ID NO:1:

(i) SEQUENCE CHARACTERISTICS:
      (A) LENGTH: 77 base pairs
      (B) TYPE: nucleic acid
      (C) STRANDEDNESS: single
      (D) TOPOLOGY: linear (xi) SEQUENCE DESCRIPTION: SEQ ID NO:1:

GGGAGCUCAG AAUAAACGCU CAANNNNNNN NNNNNNNNNN NNNNNNNNNN    50

NNNUUCGACA UGAGGCCCGG AUCCGGC    77

(2) INFORMATION FOR SEQ ID NO:2:

(i) SEQUENCE CHARACTERISTICS:
      (A) LENGTH: 48 base pairs
      (B) TYPE: nucleic acid
      (C) STRANDEDNESS: single
      (D) TOPOLOGY: linear (xi) SEQUENCE DESCRIPTION: SEQ ID NO:2:

CCGAAGCTTA ATACGACTCA CTATAGGGAG CTCAGAATAA ACGCTCAA    48

(2) INFORMATION FOR SEQ ID NO:3:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (xi) SEQUENCE DESCRIPTION: SEQ ID NO:3:

GCCGGATCCG GGCCTCATGT CGAA    24

(2) INFORMATION FOR SEQ ID NO:4:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:4:

```
GGGAGAUGCC UGUCGAGCAU GCUGNNNNNN NNNNNNNNNN NNNNNNNNNN        50

NNNNGUAGCU AAACAGCUUU GUCGACGGG                               79
```

(2) INFORMATION FOR SEQ ID NO:5:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:5:

```
CCCGAAGCTT AATACGACTC ACTATAGGGA GATGCCTGTC GAGCATGCTG        50
```

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:6:

```
CCCGTCGACA AAGCTGTTTA GCTAC                                   25
```

(2) INFORMATION FOR SEQ ID NO:7:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (xi) SEQUENCE DESCRIPTION: SEQ ID NO:7:

```
CUAACCAGG                                                      9
```

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:8:

```
UGCUAUUCGC CUAACUCGGC GCUCCUACCU                              30
```

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:9:

```
AUCUCCUCCC GUCGAAGCUA ACCUGGCCAC                              30
```

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:10:

UCGGCGAGCU AACCAAGACA CUCGCUGCAC                                            30

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:11:

GUAGCACUAU CGGCCUAACC CGGUAGCUCC                                            30

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:12:

ACCCGCGGCC UCCGAAGCUA ACCAGGACAC                                            30

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:13:

UGGGUGCUAA CCAGGACACA CCCACGCUGU                                            30

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:14:

CACGCACAGC UAACCAAGCC ACUGUGCCCC                                            30

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:15:

CUGCGUGGUA UAACCACAUG CCCUGGGCGA                                            30

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:16:

UGGGUGCUUA ACCAGGCCAC ACCCUGCUGU                              30

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:17:

CUAGGUGCUA UCCAGGACUC UCCCUGGUCC                              30

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:18:

UGCUAUUCGC CUAGCUCGGC GCUCCUACCU                              30

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:19:

AGCUAUUCGC CCAACCCGGC GCUCCCGACC                              30

(2) INFORMATION FOR SEQ ID NO:20:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:20:

ACCAGCUGCG UGCAACCGCA CAUGCCUGG                               29

(2) INFORMATION FOR SEQ ID NO:21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:21:

CAGGCCCCGU CGUAAGCUAA CCUGGACCCU                              30

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:22:

UGGGUGCUAA CCACCACACA CUCACGCUGU                      30

(2) INFORMATION FOR SEQ ID NO:23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:23:

RRGGHAACGY WNNGDCAAGN NCACYY                          26

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:24:

GGGUAACGUU GUGACAAGUA CACCUGCGUC                      30

(2) INFORMATION FOR SEQ ID NO:25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:25:

GGGGCAACGC UACAGACAAG UGCACCCAAC                      30

(2) INFORMATION FOR SEQ ID NO:26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:26:

CGUCAGAAGG CAACGUAUAG GCAAGCACAC                      30

(2) INFORMATION FOR SEQ ID NO:27:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:27:

CCUCUCGAAG ACAACGCUGU GACAAGACAC                      30

(2) INFORMATION FOR SEQ ID NO:28:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:28:

AGUGGGAAAC GCUACUUGAC AAGACACCAC                                     30

(2) INFORMATION FOR SEQ ID NO:29:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:29:

GGCUACGCUA AUGACAAGUG CACUUGGGUG                                     30

(2) INFORMATION FOR SEQ ID NO:30:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:30:

CUCUGGUAAC GCAAUGUCAA GUGCACAUGA                                     30

(2) INFORMATION FOR SEQ ID NO:31:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:31:

AGCCGCAGGU AACGGACCGG CGAGACCAUU                                     30

(2) INFORMATION FOR SEQ ID NO:32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:32:

ACGAGCUUCG UAACGCUAUC GACAAGUGCA                                     30

(2) INFORMATION FOR SEQ ID NO:33:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:33:

AAGGGGAAAC GUUGAGUCCG GUACACCCUG                                     30

(2) INFORMATION FOR SEQ ID NO:34:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO:34:

AGGGUAACGU ACUGGCAAGC UCACCUCAGC                                          30

(2) INFORMATION FOR SEQ ID NO:35:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO:35:

GAGGUAACGU ACGACAAGAC CACUCCAACU                                          30

(2) INFORMATION FOR SEQ ID NO:36:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO:36:

AGGUAACGCU GAGUCAAGUG CACUCGACAU                                          30

(2) INFORMATION FOR SEQ ID NO:37:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO:37:

GGGAAACGCU AUCGACGAGU GCACCCGGCA                                          30

(2) INFORMATION FOR SEQ ID NO:38:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO:38:

CCGAGGGUAA CGUUGGGUCA AGCACACCUC                                          30

(2) INFORMATION FOR SEQ ID NO:39:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (xi) SEQUENCE DESCRIPTION: SEQ ID NO:39:

UCGGGGUAAC GUAUUGGCAA GGCACCCGAC                                          30

(2) INFORMATION FOR SEQ ID NO:40:

(i) SEQUENCE CHARACTERISTICS:

(A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:40:

GGUAACGCUG UGGACAAGUG CACCAGCUGC                                        30

(2) INFORMATION FOR SEQ ID NO: 41:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:41:

AGGGUAACGU ACUGGCAAGC UCACCUCAGC                                        30

(2) INFORMATION FOR SEQ ID NO:42:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:42:

AGGGUAACGU AUAGUCAAGA CACCUCAAGU                                        30

(2) INFORMATION FOR SEQ ID NO:43:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:43:

GGGUAACGCA UUGGCAAGAC ACCCAGCCCC                                        30

(2) INFORMATION FOR SEQ ID NO:44:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:44:

GAGGAAACGU ACCGUCGAGC CACUCCAUGC                                        30

(2) INFORMATION FOR SEQ ID NO:45:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:45:

AGGUAACGCU GAGUCAAGUG CACUCGACAU                                        30

(2) INFORMATION FOR SEQ ID NO:46:

(i) SEQUENCE CHARACTERISTICS:
            (A) LENGTH: 30 base pairs (B) TYPE: nucleic acid
        (C) STRANDEDNESS: single
        (D) TOPOLOGY: linear (xi) SEQUENCE DESCRIPTION: SEQ ID NO:46:

GGGUAACGUG UGACAAGAUC ACCCAGUUUG                                    30

(2) INFORMATION FOR SEQ ID NO:47:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:47:

CACAGGGCAA CGCUGCUGAC AAGUGCACCU                                    30

(2) INFORMATION FOR SEQ ID NO:48:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:48:

ACGCCAAGUG AGUCAGCAAC AGAGCGUCCG                                    30

(2) INFORMATION FOR SEQ ID NO:49:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:49:

CCAGUGAGUC CUGGUAAUCC GCAUCGGGCU                                    30

(2) INFORMATION FOR SEQ ID NO:50:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:50:

CUUCAGAACG GCAUAGUGGU CGGCCGCGCC                                    30

(2) INFORMATION FOR SEQ ID NO:51:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:51:

AGGUCACUGC GUCACCGUAC AUGCCUGGCC                                    30

(2) INFORMATION FOR SEQ ID NO:52:

(i) SEQUENCE CHARACTERISTICS:
        (A) LENGTH: 30 base pairs
        (B) TYPE: nucleic acid (C) STRANDEDNESS: single
        (D) TOPOLOGY: linear (xi) SEQUENCE DESCRIPTION: SEQ ID NO:52:

UCCAACGAAC GGCCCUCGUA UUCAGCCACC                                              30

(2) INFORMATION FOR SEQ ID NO:53:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:53:

ACUGGAACCU GACGUAGUAC AGCGACCCUC                                              30

(2) INFORMATION FOR SEQ ID NO:54:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:54:

UCUCGCUGCG CCUACACGGC AUGCCGGGA                                               29

(2) INFORMATION FOR SEQ ID NO:55:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:55:

GAUCACUGCG CAAUGCCUGC AUACCUGGUC                                              30

(2) INFORMATION FOR SEQ ID NO:56:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:56:

UCUCGCUGCG CCUACACGGC AUGCCCGGGA                                              30

(2) INFORMATION FOR SEQ ID NO:57:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:57:

UGACCAGCUG CAUCCGACGA UAUACCCUGG                                              30

(2) INFORMATION FOR SEQ ID NO:58:

(i) SEQUENCE CHARACTERISTICS:
        (A) LENGTH: 30 base pairs
        (B) TYPE: nucleic acid
        (C) STRANDEDNESS: single (D) TOPOLOGY: linear (xi) SEQUENCE DESCRIPTION: SEQ ID NO:58:

GGCACACUCC AACGAGGUAA CGUUACGGCG                                    30

(2) INFORMATION FOR SEQ ID NO:59:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:59:

AGCGGAACGC CACGUAGUAC GCCGACCCUC                                    30

(2) INFORMATION FOR SEQ ID NO:60:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:60:

ACCCACGCCC GACAACCGAU GAGUUCUCGG                                    30

(2) INFORMATION FOR SEQ ID NO:61:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:61:

UGCUUUGAAG UCCUCCCCGC CUCUCGAGGU                                    30

(2) INFORMATION FOR SEQ ID NO:62:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:62:

AUGCUGAGGA UAUUGUGACC ACUUCGGCGU                                    30

(2) INFORMATION FOR SEQ ID NO:63:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:63:

ACCCACGCCC GACAACCGAU GAGCUCGGA                                     29

(2) INFORMATION FOR SEQ ID NO:64:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:64:

AGUCCGGAUG CCCCACUGGG ACUACAUUGU                                    30

(2) INFORMATION FOR SEQ ID NO:65:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:65:

AAGUCCGAAU GCCACUGGGA CUACCACUGA                                    30

(2) INFORMATION FOR SEQ ID NO:66:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:66:

ACUCUCACUG CGAUUCGAAA UCAUGCCUGG                                    30

(2) INFORMATION FOR SEQ ID NO:67:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:67:

AGGCUGGGUC ACCGACAACU GCCCGCCAGC                                    30

(2) INFORMATION FOR SEQ ID NO:68:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:68:

AGCCGCAGGU AACGGACCGG CGAGACCACU                                    30

(2) INFORMATION FOR SEQ ID NO:69:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:69:

GCAUGAAGCG GAACUGUAGU ACGCGAUCCA                                    30

(2) INFORMATION FOR SEQ ID NO:70:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:70:

GGGUAACGUU GUGACAAGUA CACCUGCGUU                                    30

(2) INFORMATION FOR SEQ ID NO:71:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:71:

GGGUAACGUU GUGACAAGUA CACCUGCGUC                                    30

(2) INFORMATION FOR SEQ ID NO:72:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:72:

GGGUAACGUU GUGACAAGUA CACCUGCGUC                                    30

(2) INFORMATION FOR SEQ ID NO:73:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:73:

GGGUAACGUU GUGACAACUA CACCUGCGUC                                    30

(2) INFORMATION FOR SEQ ID NO:74:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:74:

GGGUAACGUU GUGACAACUA CACCUGCGUC                                    30

(2) INFORMATION FOR SEQ ID NO:75:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:75:

GGGUAACGUU GUGACAACUA CACCUGCGUC                                    30

(2) INFORMATION FOR SEQ ID NO:76:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:76:

CGUCAGAAGG CAACGUAUAG GCAAGCACAC                                    30

(2) INFORMATION FOR SEQ ID NO:77:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:77:

GUAGCACUAU CGGCCUAACC CGGUAGCUCC                                    30

(2) INFORMATION FOR SEQ ID NO:78:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:78:

ACCCGCGGCC UCCGAAGCUA ACCAGGACAC                                    30

(2) INFORMATION FOR SEQ ID NO:79:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:79:

AGGUCACUGC GUCACCGUAC AUGCCUGGCC                                    30

(2) INFORMATION FOR SEQ ID NO:80:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:80:

AGGUCACUGC GUCACCGUAC AUGCCUGGCC                                    30

(2) INFORMATION FOR SEQ ID NO:81:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:81:

GGCACACUCC AACGAGGUAA CGUUACGGCG                                    30

(2) INFORMATION FOR SEQ ID NO:82:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:82:

GGGGCAACGC UACAGACAAG UGCACCCAAC                        30

(2) INFORMATION FOR SEQ ID NO:83:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:83:

GGGGCAACGC UACAGACAAG UGCACCCAAC                        30

(2) INFORMATION FOR SEQ ID NO:84:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:84:

GGGGCAACGC UACAGACAAG UGCACCCAAC                        30

(2) INFORMATION FOR SEQ ID NO:85:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:85:

UGGGUGCUAA CCAGGACACA CCCACGCUGU                        30

(2) INFORMATION FOR SEQ ID NO:86:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:86:

CCGAGGGUAA CGUUGGGUCA AGCACACCUC                        30

(2) INFORMATION FOR SEQ ID NO:87:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:87:

GGGAAACGCU AUCGACGAGU GCACCCGGCA                        30

(2) INFORMATION FOR SEQ ID NO:88:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:88:

GGGAAACGCU AUCGACGAGU GCACCCGGCA                        30

(2) INFORMATION FOR SEQ ID NO:89:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:89:

ACUCUCACUG CGAUUCGAAA UCAUGCCUGG                                      30

(2) INFORMATION FOR SEQ ID NO:90:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:90:

GCAUGAAGCG GAACUGUAGU ACGCGAUCCA                                      30

(2) INFORMATION FOR SEQ ID NO:91:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:91:

GCAUGAAGCG GAACUGUAGU ACGCGAUCCA                                      30

(2) INFORMATION FOR SEQ ID NO:92:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:92:

AGGGUAACGU ACUGGCAAGC UCACCUCAGC                                      30

(2) INFORMATION FOR SEQ ID NO:93:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:93:

AGGGUAACGU ACUGGCAAGC UCACCUCAGC                                      30

(2) INFORMATION FOR SEQ ID NO:94:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:94:

GGUAACGCUG UGGACAAGUG CACCAGCUGC                                      30

(2) INFORMATION FOR SEQ ID NO:95:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:95:

GGGAGACAAG AAUAACGCUC AANNNNNNNN NNNNNNNNNN NNNNNNNNNN     50

NNUUCGACAG GAGGCUCACA ACAGGC     76

(2) INFORMATION FOR SEQ ID NO:96:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:96:

TAATACGACT CACTATAGGG AGACAAGAAU AACGCUCAA     39

(2) INFORMATION FOR SEQ ID NO:97:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:97:

GCCTGTTGTG AGCCTCCTGT CGAA     24

(2) INFORMATION FOR SEQ ID NO:98:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:98:

GGGAGGACGA UGCGGNNNNN NNNNNNNNNN NNNNNNNNNN NNNNNNNNNN     50

NNNNNNNNNN NNNNNCAGAC GACTCGCCCG A     81

(2) INFORMATION FOR SEQ ID NO:99:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:99:

```
TAATACGACT CACTATAGGG AGGACGAUGC GG                              32

(2) INFORMATION FOR SEQ ID NO:100:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:100:

TCGGGCGAGT CGTCTG                                                16

(2) INFORMATION FOR SEQ ID NO:101:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION:  All C's are 2'-NH$_2$ cytosine (ix) FEATURE:
        (D) OTHER INFORMATION:  All U's are 2'-NH$_2$ uracil (xi) SEQUENCE DESCRIPTION: SEQ ID NO:101:

ACANGGAGUU GUGUGGAAGG CAGGGGGAGG                                 30

(2) INFORMATION FOR SEQ ID NO:102:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION:  All C's are 2'-NH$_2$ cytosine (ix) FEATURE:
        (D) OTHER INFORMATION:  All U's are 2'-NH$_2$ uracil (xi) SEQUENCE DESCRIPTION: SEQ ID NO:102:

UGUGUGGAAG GCAGUGGGAG GUUCAGUGGU                                 30

(2) INFORMATION FOR SEQ ID NO:103:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION:  All C's are 2'-NH$_2$ cytosine (ix) FEATURE:
        (D) OTHER INFORMATION:  All U's are 2'-NH$_2$ uracil (xi) SEQUENCE DESCRIPTION: SEQ ID NO:103:

AAAGUUGUGU GGAAGACAGU GGGAGGUGAA                                 30

(2) INFORMATION FOR SEQ ID NO:104:

(i) SEQUENCE CHARACTERISTICS:
        (A) LENGTH: 30 base pairs
        (B) TYPE: nucleic acid
        (C) STRANDEDNESS: single
```

(D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:104:

GUAGACUAAU GUGUGGAAGA CAGCGGGUGG                                           30

(2) INFORMATION FOR SEQ ID NO:105:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:105:

NNAGUUGUGU GGAAGACAGU GGGGGGUUGA                                           30

(2) INFORMATION FOR SEQ ID NO:106:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:106:

GGUGUGUNGA AGACAGUGGG UNGUUUAGNC                                           30

(2) INFORMATION FOR SEQ ID NO:107:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:107:

AUGGUGUGUG GAAGACAGUG GGUGGUUGCA                                           30

(2) INFORMATION FOR SEQ ID NO:108:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:

(D) OTHER INFORMATION: All C's are 2'-NH$_2$ cytosine (ix) FEATURE:
            (D) OTHER INFORMATION: All U's are 2'-NH$_2$ uracil (xi) SEQUENCE DESCRIPTION: SEQ ID NO:108:

ACUGUUGUGU GGAAGACAGC GGGUGGUUGA                                          30

(2) INFORMATION FOR SEQ ID NO:109:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ix) FEATURE:
            (D) OTHER INFORMATION: All C's are 2'-NH$_2$ cytosine (ix) FEATURE:
            (D) OTHER INFORMATION: All U's are 2'-NH$_2$ uracil (xi) SEQUENCE DESCRIPTION: SEQ ID NO:109:

AAUGUAGGCU GUGUGGUAGA CAGUGGGUGG                                          30

(2) INFORMATION FOR SEQ ID NO:110:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ix) FEATURE:
            (D) OTHER INFORMATION: All C's are 2'-NH$_2$ cytosine (ix) FEATURE:
            (D) OTHER INFORMATION: All U's are 2'-NH$_2$ uracil (xi) SEQUENCE DESCRIPTION: SEQ ID NO:110:

GAUGUGUGGA GGGCAGUGGG GGGUACCAUA                                          30

(2) INFORMATION FOR SEQ ID NO:111:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ix) FEATURE:
            (D) OTHER INFORMATION: All C's are 2'-NH$_2$ cytosine (ix) FEATURE:
            (D) OTHER INFORMATION: All U's are 2'-NH$_2$ uracil (xi) SEQUENCE DESCRIPTION: SEQ ID NO:111:

GGGGUCAAGG ACAGUGGGUG GUGGUGGUGU                                          30

(2) INFORMATION FOR SEQ ID NO:112:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ix) FEATURE:
            (D) OTHER INFORMATION: All C's are 2'-NH$_2$ cytosine (ix) FEATURE:

(D) OTHER INFORMATION: All U's are 2'-NH$_2$ uracil (xi) SEQUENCE DESCRIPTION: SEQ ID NO:112:

UGCUGCGGUG CGCAUGUGUG GAAGACAGAG GGAGGUUAGA AUCAUGACGU           50

(2) INFORMATION FOR SEQ ID NO:113:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ix) FEATURE:
            (D) OTHER INFORMATION: All C's are 2'-NH$_2$ cytosine (ix) FEATURE:
            (D) OTHER INFORMATION: All U's are 2'-NH$_2$ uracil (xi) SEQUENCE DESCRIPTION: SEQ ID NO:113:

ACAGACCGUG UGUGGAAGAC AGUGGGAGGU UAUUAACGUA GUGAUGGCGC           50

(2) INFORMATION FOR SEQ ID NO:114:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ix) FEATURE:
            (D) OTHER INFORMATION: All C's are 2'-NH$_2$ cytosine (ix) FEATURE:
            (D) OTHER INFORMATION: All U's are 2'-NH$_2$ uracil (xi) SEQUENCE DESCRIPTION: SEQ ID NO:114:

GCUGCGGUGC GCAUGUGUGG AAGACAGAGG GAGGUUAGAA UCGUGCCGC            49

(2) INFORMATION FOR SEQ ID NO:115:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ix) FEATURE:
            (D) OTHER INFORMATION: All C's are 2'-NH$_2$ cytosine (ix) FEATURE:
            (D) OTHER INFORMATION: All U's are 2'-NH$_2$ uracil (xi) SEQUENCE DESCRIPTION: SEQ ID NO:115:

GAAAACUACG GUGUGUGGAA GACAGUGGGA GGUUGGCAGU CUGUGUCCGU           50

(2) INFORMATION FOR SEQ ID NO:116:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ix) FEATURE:
            (D) OTHER INFORMATION: All C's are 2'-NH$_2$ cytosine (ix) FEATURE:
            (D) OTHER INFORMATION: All U's are 2'-NH$_2$ uracil (xi) SEQUENCE DESCRIPTION: SEQ ID NO:116:

UCCAUCGUGG AAGACAGUGG GAGGUUAGAA UCAUGACGUC AGACGACUC            49

(2) INFORMATION FOR SEQ ID NO:117:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ix) FEATURE:
        (D) OTHER INFORMATION:  All C's are 2'-$NH_2$ cytosine (ix) FEATURE:
        (D) OTHER INFORMATION:  All U's are 2'-$NH_2$ uracil (xi) SEQUENCE DESCRIPTION: SEQ ID NO:117:

UGUGAUUUGU GUGGAAGGCA GUGGGAGGUG UCGAUGUAGA UCUGGCGAUG            50

(2) INFORMATION FOR SEQ ID NO:118:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (D) OTHER INFORMATION:  All C's are 2'-$NH_2$ cytosine (ix) FEATURE:
        (D) OTHER INFORMATION:  All U's are 2'-$NH_2$ uracil (xi) SEQUENCE DESCRIPTION: SEQ ID NO:118:

UGUGUGGAAG ACAGUGGGWG GUU                                        23

(2) INFORMATION FOR SEQ ID NO:119:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION:  All C's are 2'-$NH_2$ cytosine (ix) FEATURE:
        (D) OTHER INFORMATION:  All U's are 2'-$NH_2$ uracil (xi) SEQUENCE DESCRIPTION: SEQ ID NO:119:

UGUGUGGAAG GGUACCUGAG UGGGGAUGGG                                  30

(2) INFORMATION FOR SEQ ID NO:120:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ix) FEATURE:
        (D) OTHER INFORMATION:  All C's are 2'-$NH_2$ cytosine (ix) FEATURE:
        (D) OTHER INFORMATION:  All U's are 2'-$NH_2$ uracil (xi) SEQUENCE DESCRIPTION: SEQ ID NO:120:

AAGACUGUGU GGAAGGGGUG UAGGGGUUGG G                                31

(2) INFORMATION FOR SEQ ID NO:121:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:121:

UAGGGCCGCA ACUGUGUGGA AGGGAGGAUG CGUCAUGGGG GUUGGGCUG        49

(2) INFORMATION FOR SEQ ID NO:122:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:122:

UGUGUGGAAG GGNNNNUGNG UGGGGUUGGG        30

(2) INFORMATION FOR SEQ ID NO:123:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:123:

AUUGUGUGGG AUAGGGCAUA GAGGGUGUGG GAAACCCCAG ACCGGGCGU        50

(2) INFORMATION FOR SEQ ID NO:124:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:124:

UGUGUGGGAC AGCGGAUCAG GGGUGUGGGA GCGCAUAACA UCCUACNUGC        50
U        51

(2) INFORMATION FOR SEQ ID NO:125:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:125:

ANNNNUNUGC AUGUGUGGGA CAGGGUGCAU GUGGGUUGCG GGACCUUGGU      50

(2) INFORMATION FOR SEQ ID NO:126:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:126:

UGUGUGGGAC AGGGNAUANA NGGGUGUGGG A      31

(2) INFORMATION FOR SEQ ID NO:127:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:127:

GCAGGAGGAU AGGGAUCGGA UGGGGUAGGA      30

(2) INFORMATION FOR SEQ ID NO:128:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:128:

UGAGGAUCGG AUGGGAGCA GGCGGAGGAA      30

(2) INFORMATION FOR SEQ ID NO:129:

(i) SEQUENCE CHARACTERISTICS:

(A) LENGTH: 30 base pairs
                (B) TYPE: nucleic acid
                (C) STRANDEDNESS: single
                (D) TOPOLOGY: linear (ix) FEATURE:
                (D) OTHER INFORMATION:  All C's are 2'-NH₂ cytosine (ix) FEATURE:
                (D) OTHER INFORMATION:  All U's are 2'-NH₂ uracil (xi) SEQUENCE DESCRIPTION: SEQ ID NO:129:

GUGGAUUGGA AGGGGUGCUG GAGGAGGACG                                          30

(2) INFORMATION FOR SEQ ID NO:130:

(i) SEQUENCE CHARACTERISTICS:
                (A) LENGTH: 50 base pairs
                (B) TYPE: nucleic acid
                (C) STRANDEDNESS: single
                (D) TOPOLOGY: linear (ix) FEATURE:
                (D) OTHER INFORMATION:  All C's are 2'-NH₂ cytosine (ix) FEATURE:
                (D) OTHER INFORMATION:  All U's are 2'-NH₂ uracil (xi) SEQUENCE DESCRIPTION: SEQ ID NO:130:

UAGGAAUGGA UGGGGUUGGA ACAGAGUUCU AAUGUCGACC UCACAUGUGG                    50

(2) INFORMATION FOR SEQ ID NO:131:

(i) SEQUENCE CHARACTERISTICS:
                (A) LENGTH: 50 base pairs
                (B) TYPE: nucleic acid
                (C) STRANDEDNESS: single
                (D) TOPOLOGY: linear (ix) FEATURE:
                (D) OTHER INFORMATION:  All C's are 2'-NH₂ cytosine (ix) FEATURE:
                (D) OTHER INFORMATION:  All U's are 2'-NH₂ uracil (xi) SEQUENCE DESCRIPTION: SEQ ID NO:131:

CAGGAAUGGA UGGGGUUGGA ACAGAGUUCU AAUGUCGACC UCACAUGCGU                    50

(2) INFORMATION FOR SEQ ID NO:132:

(i) SEQUENCE CHARACTERISTICS:
                (A) LENGTH: 50 base pairs
                (B) TYPE: nucleic acid
                (C) STRANDEDNESS: single
                (D) TOPOLOGY: linear (ix) FEATURE:
                (D) OTHER INFORMATION:  All C's are 2'-NH₂ cytosine (ix) FEATURE:
                (D) OTHER INFORMATION:  All U's are 2'-NH₂ uracil (xi) SEQUENCE DESCRIPTION: SEQ ID NO:132:

CAGGAUAGGA UGGGGUCGGA ACCGUGUAUC AUAACGAGUC AUCUCCUGGU                    50

(2) INFORMATION FOR SEQ ID NO:133:

(i) SEQUENCE CHARACTERISTICS:
                (A) LENGTH: 14 base pairs
                (B) TYPE: nucleic acid
                (C) STRANDEDNESS: single (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:133:

GGAUHGGAUG GGGU                                                              14

(2) INFORMATION FOR SEQ ID NO:134:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:134:

UUAACGGCGU GGUCCGAGGG UGGCGAGUAC                                              30

(2) INFORMATION FOR SEQ ID NO:135:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:135:

GACUAGGCGC GGACCGUGGG UGGUGAGUGG                                              30

(2) INFORMATION FOR SEQ ID NO:136:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:136:

AGUGGCAUGG GCCGUGGGAG GUGAGUGUCG AGACUGGUGU UGGGCCU                           47

(2) INFORMATION FOR SEQ ID NO:137:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ix) FEATURE:

(D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:137:

CGUGGUUCCG UGGGUGGUGA GAUGAGACUU AAUCAGUUCG UAGACCGGU         49

(2) INFORMATION FOR SEQ ID NO:138:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:138:

CCGUGGGUGG UGAGU         15

(2) INFORMATION FOR SEQ ID NO:139:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:139:

NAAAUACGAG AGAGGANCAU ANNUGACUGA ACAUUGAUGU AUUAACGAGU         50

(2) INFORMATION FOR SEQ ID NO:140:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:140:

GAGGUACGAG AGAGGAGCGU AGGUGACUGA ACAUUGAUGU AUUAACGUGU         50

C         51

(2) INFORMATION FOR SEQ ID NO:141:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
              (D) OTHER INFORMATION:  All U's are 2'-NH₂ uracil (xi) SEQUENCE DESCRIPTION: SEQ ID NO:141:

AGGGUGGCUG GGAGGACCCG CGGUGAAUCG GUAGCACAGU GAUGUUCGGU                50

(2) INFORMATION FOR SEQ ID NO:142:

(i) SEQUENCE CHARACTERISTICS:
              (A) LENGTH: 50 base pairs
              (B) TYPE: nucleic acid
              (C) STRANDEDNESS: single
              (D) TOPOLOGY: linear (ix) FEATURE:
              (D) OTHER INFORMATION:  All C's are 2'-NH₂ cytosine (ix) FEATURE:
              (D) OTHER INFORMATION:  All U's are 2'-NH₂ uracil (xi) SEQUENCE DESCRIPTION: SEQ ID NO:142:

GAGGGUGGCA GGGAGGACCC GCGGUGAAUC GGUAGCACAG UGAGUUCGGU                50

(2) INFORMATION FOR SEQ ID NO:143:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ix) FEATURE:
              (D) OTHER INFORMATION:  All C's are 2'-NH₂ cytosine (ix) FEATURE:
              (D) OTHER INFORMATION:  All U's are 2'-NH₂ uracil (xi) SEQUENCE DESCRIPTION: SEQ ID NO:143:

CGCGAGGGCU GGCGGGGUAG GAUGGGUAGA                                       30

(2) INFORMATION FOR SEQ ID NO:144:

(i) SEQUENCE CHARACTERISTICS:
              (A) LENGTH: 50 base pairs
              (B) TYPE: nucleic acid
              (C) STRANDEDNESS: single
              (D) TOPOLOGY: linear (ix) FEATURE:
              (D) OTHER INFORMATION:  All C's are 2'-NH₂ cytosine (ix) FEATURE:
              (D) OTHER INFORMATION:  All U's are 2'-NH₂ uracil (xi) SEQUENCE DESCRIPTION: SEQ ID NO:144:

CGCGAGUGCU ACGAGGCGUG GGGGGGUGGA AACUAGUUGU GCUCUGGCCG                 50

(2) INFORMATION FOR SEQ ID NO:145:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ix) FEATURE:
              (D) OTHER INFORMATION:  All C's are 2'-NH₂ cytosine (ix) FEATURE:
              (D) OTHER INFORMATION:  All U's are 2'-NH₂ uracil (xi) SEQUENCE DESCRIPTION: SEQ ID NO:145:

GAUUGGAAGC AGGGUGUGGG UUAGGAGGGC                                30

(2) INFORMATION FOR SEQ ID NO:146:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:146:

GACCACAGUU UAAACGCCCA UCAGUGGUAG GGUGUGGGUA AGGAGGGCUG          50

(2) INFORMATION FOR SEQ ID NO:147:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:147:

CGCGAGGGCU GGCGGGGUAG GAUGGGUAGA                                30

(2) INFORMATION FOR SEQ ID NO:148:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:148:

UGGGCCGCCG GUCUUGGGUG UAUGUGUGAA                                30

(2) INFORMATION FOR SEQ ID NO:149:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:149:

```
AGUUGGGGGC UCGUGCGGCG UGGGGCGUGC                                              30
```

(2) INFORMATION FOR SEQ ID NO:150:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:150:

```
GGGAUGGUUG GAGACCGGGA GAUGGGAGGA                                              30
```

(2) INFORMATION FOR SEQ ID NO:151:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:151:

```
AAACGGGCG AUGGAAAGUG UGGGGUACGA                                               30
```

(2) INFORMATION FOR SEQ ID NO:152:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:152:

```
GAGGAGGAUG GAGAGGAGCG GUGUGCAGGG                                              30
```

(2) INFORMATION FOR SEQ ID NO:153:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:153:

```
GAGAGGGUGA AGUGGGCAGG AUGGGGUAGG                                              30
```

(2) INFORMATION FOR SEQ ID NO:154:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:154:

CUGAAAUUGC GGGUGUGGAG GUAUGCUGGG AAAGGUGGAU GGUACACGU          49

(2) INFORMATION FOR SEQ ID NO:155:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:155:

CAAUGUUUGG AGUCUGCUAA UGUGGGUGGG UUAGACGUAC CGAUGGUUGC          50

(2) INFORMATION FOR SEQ ID NO:156:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:156:

ACGGGGAAGU ACGAGAGCGG ACUGUAAGUC UAGUGGGUCA GUUCGGUG          48

(2) INFORMATION FOR SEQ ID NO:157:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:157:

UUCAGCGCGC AUUAGUGCAG CGGGUUCAAC AAAAGAGGUG UUCGUGUGUG          50

(2) INFORMATION FOR SEQ ID NO:158:

(i) SEQUENCE CHARACTERISTICS:

(A) LENGTH: 50 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:158:

CGGAUUGUGU GGUCGGGAGG GCAGUAGUUU ACACUCACCC GUGGUCUGCU           50

(2) INFORMATION FOR SEQ ID NO:159:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:159:

GGUGUGUGAC AAUGUGCGUG GGUUGGGCAG GUACAAAGCG UAUGGGCGUG           50

(2) INFORMATION FOR SEQ ID NO:160:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:160:

AACGGGAGGU ACGAGAGCGG GAGCGCAUAA AUAGGAAACU CCUUGCACGU           50

(2) INFORMATION FOR SEQ ID NO:161:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:161:

AGGCAGUAUU GGGGGUGGUC AGCGCCUCCC CAAAACUCGC ACCUUAGCCC           50

(2) INFORMATION FOR SEQ ID NO:162:

(i) SEQUENCE CHARACTERISTICS:
        (A) LENGTH: 50 base pairs
        (B) TYPE: nucleic acid
        (C) STRANDEDNESS: single (D) TOPOLOGY: linear (ix) FEATURE:
            (D) OTHER INFORMATION: All C's are 2'-NH$_2$ cytosine (ix) FEATURE:
            (D) OTHER INFORMATION: All U's are 2'-NH$_2$ uracil (xi) SEQUENCE DESCRIPTION: SEQ ID NO:162:

GGGUUGGGUG GCAAGCGGAG AGCAGGGUUA GGUGCGGACU CAUUGGUGUG                50

(2) INFORMATION FOR SEQ ID NO:163:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ix) FEATURE:
            (D) OTHER INFORMATION: All C's are 2'-NH$_2$ cytosine (ix) FEATURE:
            (D) OTHER INFORMATION: All U's are 2'-NH$_2$ uracil (xi) SEQUENCE DESCRIPTION: SEQ ID NO:163:

GGAGGGGCAG GUUCGAUGCG GGAGCGACUG ACCACGAGAA AUGUGCGGGU                50

(2) INFORMATION FOR SEQ ID NO:164:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ix) FEATURE:
            (D) OTHER INFORMATION: All C's are 2'-NH$_2$ cytosine (ix) FEATURE:
            (D) OTHER INFORMATION: All U's are 2'-NH$_2$ uracil (xi) SEQUENCE DESCRIPTION: SEQ ID NO:164:

CUCAGCAUCC AGGAAGGGGA CUUGGUAGGG CACCAUCGAG AUCUUGGCGU                50

(2) INFORMATION FOR SEQ ID NO:165:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ix) FEATURE:
            (D) OTHER INFORMATION: All C's are 2'-NH$_2$ cytosine (ix) FEATURE:
            (D) OTHER INFORMATION: All U's are 2'-NH$_2$ uracil (xi) SEQUENCE DESCRIPTION: SEQ ID NO:165:

ACCCUAGGCA UCCAGGUUGG GGAUAGCGGU UGGAGUGAAU GUGUUGUGCC                50

(2) INFORMATION FOR SEQ ID NO:166:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ix) FEATURE:

(D) OTHER INFORMATION:  All C's are 2'-NH₂ cytosine (ix) FEATURE:
            (D) OTHER INFORMATION:  All U's are 2'-NH₂ uracil (xi) SEQUENCE DESCRIPTION: SEQ ID NO:166:

CACGGAGGAG GAGGUCAGAC UUAGCGGUCA                                           30

(2) INFORMATION FOR SEQ ID NO:167:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ix) FEATURE:
            (D) OTHER INFORMATION:  All C's are 2'-NH₂ cytosine (ix) FEATURE:
            (D) OTHER INFORMATION:  All U's are 2'-NH₂ uracil (xi) SEQUENCE DESCRIPTION: SEQ ID NO:167:

UACAGGGGAA GGAGNGAAUU GCAAGAUGAA                                           30

(2) INFORMATION FOR SEQ ID NO:168:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ix) FEATURE:
            (D) OTHER INFORMATION:  All C's are 2'-NH₂ cytosine (ix) FEATURE:
            (D) OTHER INFORMATION:  All U's are 2'-NH₂ uracil (xi) SEQUENCE DESCRIPTION: SEQ ID NO:168:

AAAGUUGUGU GGAAGACAGU GGGAGGUGAA                                           30

(2) INFORMATION FOR SEQ ID NO:169:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ix) FEATURE:
            (D) OTHER INFORMATION:  All C's are 2'-NH₂ cytosine (ix) FEATURE:
            (D) OTHER INFORMATION:  All U's are 2'-NH₂ uracil (xi) SEQUENCE DESCRIPTION: SEQ ID NO:169:

UGAUGGCGGU AGUGGAGGUA AUGAGCGUNA                                           30

(2) INFORMATION FOR SEQ ID NO:170:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ix) FEATURE:
            (D) OTHER INFORMATION:  All C's are 2'-NH₂ cytosine (ix) FEATURE:

(D) OTHER INFORMATION: All U's are 2'-NH$_2$ uracil (xi) SEQUENCE DESCRIPTION: SEQ ID NO:170:

UAGGAGGUUG GAGGAAAGCU UCACAGCCGA                              30

(2) INFORMATION FOR SEQ ID NO:171:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ix) FEATURE:
      (D) OTHER INFORMATION: All C's are 2'-NH$_2$ cytosine (ix) FEATURE:
      (D) OTHER INFORMATION: All U's are 2'-NH$_2$ uracil (xi) SEQUENCE DESCRIPTION: SEQ ID NO:171:

UGAGGAGGAG GAGGACAGGA UUCAACGAGU                              30

(2) INFORMATION FOR SEQ ID NO:172:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ix) FEATURE:
      (D) OTHER INFORMATION: All C's are 2'-NH$_2$ cytosine (ix) FEATURE:
      (D) OTHER INFORMATION: All U's are 2'-NH$_2$ uracil (xi) SEQUENCE DESCRIPTION: SEQ ID NO:172:

GUUAGGAGGG UGGAGGUUCG AGUGUGGCAA                              30

(2) INFORMATION FOR SEQ ID NO:173:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ix) FEATURE:
      (D) OTHER INFORMATION: All C's are 2'-NH$_2$ cytosine (ix) FEATURE:
      (D) OTHER INFORMATION: All U's are 2'-NH$_2$ uracil (xi) SEQUENCE DESCRIPTION: SEQ ID NO:173:

CGUCGAGUGC GAUGGAGGAG GAGGGAUGCA                              30

(2) INFORMATION FOR SEQ ID NO:174:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ix) FEATURE:
      (D) OTHER INFORMATION: All C's are 2'-NH$_2$ cytosine (ix) FEATURE:
      (D) OTHER INFORMATION: All U's are 2'-NH$_2$ uracil (xi) SEQUENCE DESCRIPTION: SEQ ID NO:174:

GGGGUCAAGG ACAGUGGGUG GUGGUGGUGU                                      30

(2) INFORMATION FOR SEQ ID NO:175:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:175:

GGAGGGAGGA GGGAUGAUGA GCUCAUCAGC                                      30

(2) INFORMATION FOR SEQ ID NO:176:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:176:

CAAACAGGAG GGAAUGGAGG GNG                                             23

(2) INFORMATION FOR SEQ ID NO:177:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:177:

AGGGGUGGUC GGUAAGCUCG GUGGUGGUGG                                      30

(2) INFORMATION FOR SEQ ID NO:178:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:178:

AGGAGGGUUA AGGAGGGAGA UUAAGCGUUG G                                    31

(2) INFORMATION FOR SEQ ID NO:179:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:179:

GUGGAGGGUA CGUGGAGGGG AGAGCGACA                                               29

(2) INFORMATION FOR SEQ ID NO:180:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:180:

AUAAUUCAAG GAGGUGGAGG ACAGAUGCGC                                             30

(2) INFORMATION FOR SEQ ID NO:181:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:181:

GAUGAGGACU CGGGGCGGAG GGUGGUACCA                                             30

(2) INFORMATION FOR SEQ ID NO:182:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:182:

AGGUCGUGGC UGGGAUUCGU CCUCGACAUG UACAUUGUGG CUCUGGUGCC         50

(2) INFORMATION FOR SEQ ID NO:183:

(i) SEQUENCE CHARACTERISTICS:
    (A) LENGTH: 43 base pairs
    (B) TYPE: nucleic acid
    (C) STRANDEDNESS: single
    (D) TOPOLOGY: linear (ix) FEATURE:
    (D) OTHER INFORMATION: All C's are 2'-NH$_2$ cytosine (ix) FEATURE:
    (D) OTHER INFORMATION: All U's are 2'-NH$_2$ uracil (xi) SEQUENCE DESCRIPTION: SEQ ID NO:183:

AAGUUAGUCA UCGUGCAAAC UGCGAGUGCA CUGCUCGGGA UCC                43

(2) INFORMATION FOR SEQ ID NO:184:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:184:

GACCACAGUU UAAACGCCCA UCAGUGGUAG GGUGUGGGUA AGGAGGGCUG          50

(2) INFORMATION FOR SEQ ID NO:185:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ix) FEATURE:
        (D) OTHER INFORMATION: All C's are 2'-NH$_2$ cytosine (ix) FEATURE:
        (D) OTHER INFORMATION: All U's are 2'-NH$_2$ uracil (xi) SEQUENCE DESCRIPTION: SEQ ID NO:185:

CGCGAGUGCU ACGAGGCGUG GGGGGGUGGA AACUAGUUGU GCUCUGGCCG          50

(2) INFORMATION FOR SEQ ID NO:186:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:186:

GGUGUGUGGA AGACAGCGGG UGGUUC                                   26

(2) INFORMATION FOR SEQ ID NO:187:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:187:

GGACGGCGUG GUCCGAGGGU GGCGAGU                                  27

(2) INFORMATION FOR SEQ ID NO:188:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:188:

GGAGGACGAU GCGGAACGGG AGGUACGAGA GCGGGAGC                                      38

(2) INFORMATION FOR SEQ ID NO:189:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:189:

GGTTGGTGTG GTTGG                                                                        15

(2) INFORMATION FOR SEQ ID NO:190:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:190:

GGAUCGAAGN NAGUAGGC                                                                 18

(2) INFORMATION FOR SEQ ID NO:191:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:191:

GCGGCUUUGG GCGCCGUGCU U                                                   21

(2) INFORMATION FOR SEQ ID NO:192:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (xi) SEQUENCE DESCRIPTION: SEQ ID NO:192:

AGAUGCCUGU CGAGCAUGCU GAGGAUCGAA GUUAGUAGGC UUUGUGUGCU          50

CGUAGCUAAA CAGCUUUGUC GACGGG                                          76

(2) INFORMATION FOR SEQ ID NO:193:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (xi) SEQUENCE DESCRIPTION: SEQ ID NO:193:

```
AGAUGCCUGU CGAGCAUGCU GUACUGGAUC GAAGGUAGUA GGCAGUCACG            50

UAGCUAAACA GCUUUGUCGA CGGG                                       74
```

(2) INFORMATION FOR SEQ ID NO:194:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:194:

```
AGAUGCCUGU CGAGCAUGCU GAUAUCACGG AUCGAAGGAA GUAGGCGUGG            50

GUAGCUAAAC AGCUUUGUCG ACGGG                                      75
```

(2) INFORMATION FOR SEQ ID NO:195:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (xi) SEQUENCE DESCRIPTION: SEQ ID NO:195:

```
AGAUGCCUGU CGAGCAUGCU GCCUUUCCCG GGUUCGAAGU CAGUAGGCCG            50

GGUAGCUAAA CAGCUUUGUC GACGGG                                     76
```

(2) INFORMATION FOR SEQ ID NO:196:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:196:

```
AGAUGCCUGU CGAGCAUGCU GCACCCGGAU CGAAGUUAGU AGGCGUGAGU            50

GUAGCUAAAC AGCUUUGUCG ACGGG                                      75
```

(2) INFORMATION FOR SEQ ID NO:197:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (xi) SEQUENCE DESCRIPTION: SEQ ID NO:197:

```
AGAUGCCUGU CGAGCAUGCU GUGUACGGAU CGAAGGUAGU AGGCAGGUUA            50

CGUAGCUAAA CAGCUUUGUC GACGGG                                     76
```

(2) INFORMATION FOR SEQ ID NO:198:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (xi) SEQUENCE DESCRIPTION: SEQ ID NO:198:

```
AGAUGCCUGU CGAGCAUGCU GCAUCCGGAU CGAAGUUAGU AGGCCGAGGU            50

GGUAGCUAAA CAGCUUUGUC GACGGG                                     76
```

(2) INFORMATION FOR SEQ ID NO:199:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (xi) SEQUENCE DESCRIPTION: SEQ ID NO:199:

```
AGAUGCCUGU CGAGCAUGCU GAUUGUUGCG GAUCGAAGUG AGUAGGCGCU        50

AGUAGCUAAA CAGCUUUGUC GACGGG                                 76
```

(2) INFORMATION FOR SEQ ID NO:200:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (xi) SEQUENCE DESCRIPTION: SEQ ID NO:200:

```
AGAUGCCUGU CGAGCAUGCU GUGUACUGGA UCGAAGGUAG UAGGCAGUCA        50

CGUAGCUAAA CAGCUUUGUC GACGGG                                 76
```

(2) INFORMATION FOR SEQ ID NO:201:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:201:

```
AGAUGCCUGU CGAGCAUGCU GAUCGAAGUU AGUAGGAGCG UGUGGUAGCU        50

AAACAGCUUU GUCGACGGG                                         69
```

(2) INFORMATION FOR SEQ ID NO:202:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:202:

```
AGAUGCCUGU CGAGCAUGCU GACGCUGGAG UCGGAUCGAA AGGUAAGUAG        50

GCGACUGUAG CUAAACAGCU UUGUCGACGG G                           81
```

(2) INFORMATION FOR SEQ ID NO:203:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:203:

```
AGAUGCCUGU CGAGCAUGCU GGGGUCGGAU CGAAAGGUAA GUAGGCGACU        50

GUAGCUAAAC AGCUUUGUCG ACGGG                                  75
```

(2) INFORMATION FOR SEQ ID NO:204:

(i) SEQUENCE CHARACTERISTICS:

(A) LENGTH: 74 base pairs
                (B) TYPE: nucleic acid
                (C) STRANDEDNESS: single
                (D) TOPOLOGY: linear (xi) SEQUENCE DESCRIPTION: SEQ ID NO:204:

AGAUGCCUGU CGAGCAUGCU GAUAUCACGG AUCGAAAGAG AGUAGGCGUG           50

UAGCUAAACA GCUUUGUCGA CGGG                                       74

(2) INFORMATION FOR SEQ ID NO:205:

(i) SEQUENCE CHARACTERISTICS:
                (A) LENGTH: 76 base pairs
                (B) TYPE: nucleic acid
                (C) STRANDEDNESS: single
                (D) TOPOLOGY: linear (xi) SEQUENCE DESCRIPTION: SEQ ID NO:205:

AGAUGCCUGU CGAGCAUGCU GUGUACUGGA UCGAAGGUAG UAGGCAGGCA           50

CGUAGCUAAA CAGCUUUGUC GACGGG                                     76

(2) INFORMATION FOR SEQ ID NO:206:

(i) SEQUENCE CHARACTERISTICS:
                (A) LENGTH: 75 base pairs
                (B) TYPE: nucleic acid
                (C) STRANDEDNESS: single
                (D) TOPOLOGY: linear (xi) SEQUENCE DESCRIPTION: SEQ ID NO:206:

AGAUGCCUGU CGAGCAUGCU GAUAUCACGG AUCGAAGGAA AGUAGGCGUG           50

GUAGCUAAAC AGCUUUGUCG ACGGG                                      75

(2) INFORMATION FOR SEQ ID NO:207:

(i) SEQUENCE CHARACTERISTICS:
                (A) LENGTH: 72 base pairs
                (B) TYPE: nucleic acid
                (C) STRANDEDNESS: single
                (D) TOPOLOGY: linear (xi) SEQUENCE DESCRIPTION: SEQ ID NO:207:

AGAUGCCUGU CGAGCAUGCU GGUGCGGCUU UGGGCGCCGU GCUUGGCGUA           50

GCUAAACAGC UUUGUCGACG GG                                         72

(2) INFORMATION FOR SEQ ID NO:208:

(i) SEQUENCE CHARACTERISTICS:
                (A) LENGTH: 71 base pairs
                (B) TYPE: nucleic acid
                (C) STRANDEDNESS: single
                (D) TOPOLOGY: linear (xi) SEQUENCE DESCRIPTION: SEQ ID NO:208:

AGAUGCCUGU CGAGCAUGCU GGUGCGGCUU UGGGCGCCGU GCUUACGUAG           50

CUAAACAGCU UUGUCGACGG G                                          71

(2) INFORMATION FOR SEQ ID NO:209:

(i) SEQUENCE CHARACTERISTICS:
                (A) LENGTH: 72 base pairs
                (B) TYPE: nucleic acid
                (C) STRANDEDNESS: single
                (D) TOPOLOGY: linear (xi) SEQUENCE DESCRIPTION: SEQ ID NO:209:

AGAUGCCUGU CGAGCAUGCU GGUGCGGCUU UGGGCGCCGU GCUUGACGUA       50

GCUAAACAGC UUUGUCGACG GG       72

(2) INFORMATION FOR SEQ ID NO:210:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:210:

AGAUGCCUGU CGAGCAUGCU GGGGCGGCUU UGGGCGCCGU GCUUGACGUA       50

GCUAAACAGC UUUGUCGACG GG       72

(2) INFORMATION FOR SEQ ID NO:211:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:211:

GGGAGAUGCC UGUCGAGCAU GCUGAGGAUC GAAGUUAGUA GGCUUUGUGU       50

GCUCGUAGCU AAACAGCUUU GUCGACGGG       79

(2) INFORMATION FOR SEQ ID NO:212:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:212:

GGGAGAUGCC UGUCGAGCAU GCUGCAUCCG GAUCGAAGUU AGUAGGCCGA       50

GGUGGUAGCU AAACAGCUUU GUCGACGGG       79

(2) INFORMATION FOR SEQ ID NO:213:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:213:

GGGAGAUGCC UGUCGAGCAU GCUGAUUGUU GCGGAUCGAA GUGAGUAGGC       50

GCUAGUAGCU AAACAGCUUU GUCGACGGG       79

(2) INFORMATION FOR SEQ ID NO:214:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:214:

GGGAGAUGCC UGUCGAGCAU GCUGGUGCGG CUUUGGGCGC CGUGCUUGAC       50

GUAGCUAAAC AGCUUUGUCG ACGGG                                                  75

(2) INFORMATION FOR SEQ ID NO:215:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:215:

AGATGCCTGT CGAGCATGCT NNNNNNNNNN NNNNNNNNNN NNNNNNNNNN                        50

GTAGCTAAAC TGCTTTGTCG ACGGG                                                  75

(2) INFORMATION FOR SEQ ID NO:216:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:216:

TCACTAGGCT AGGTGTGCAT GATGCTAGTG                                             30

(2) INFORMATION FOR SEQ ID NO:217:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:217:

GTCAGCTACC GTGGTAGGGA AGGTTGGAGT                                             30

(2) INFORMATION FOR SEQ ID NO:218:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:218:

ACTAGCGGGG TAGTGGTGGG TTGGGGTCTA                                             30

(2) INFORMATION FOR SEQ ID NO:219:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:219:

ACACCCGTGG TAGGGTAGGA TGGGGTGGTC                                             30

(2) INFORMATION FOR SEQ ID NO:220:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:220:

GCAGTTGTGC TCGTGGTAGG GTAGGATGGG                                    30

(2) INFORMATION FOR SEQ ID NO:221:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:221:

GTGAATAGGT AGGGTCGGAT GGGCTACGGT                                    30

(2) INFORMATION FOR SEQ ID NO:222:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:222:

GAGTTGAGGG TAGGCGTGGG ATGGTGGAAC                                    30

(2) INFORMATION FOR SEQ ID NO:223:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:223:

ATGTGCTACC GTGGTAGGGA AGGATGGTGT                                    30

(2) INFORMATION FOR SEQ ID NO:224:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:224:

GTTGTGGTAG GGTTAGGGAT GGTAGCGGTT                                    30

(2) INFORMATION FOR SEQ ID NO:225:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:225:

GTTGGCGGGA GTGGTAGGCA GTAGGGTTGG                                    30

(2) INFORMATION FOR SEQ ID NO:226:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:226:

```
GCCGCTACGA GGGTAGGTGT GGATGCTGCC                                30
```

(2) INFORMATION FOR SEQ ID NO:227:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:227:

```
GTTTTGGTAT AGGCTAGGTG TGCATGATGC T                              31
```

(2) INFORMATION FOR SEQ ID NO:228:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:228:

```
GTTTATCGGT AGGGTTGGTT GGGCTACAAT                                30
```

(2) INFORMATION FOR SEQ ID NO:229:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:229:

```
ACGGACCGCG CGACGAACTG TGAAGGGCCG                                30
```

(2) INFORMATION FOR SEQ ID NO:230:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:230:

```
GCGTTTAGCT CGGGGTAGTG GTGGGTTGGT                                30
```

(2) INFORMATION FOR SEQ ID NO:231:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:231:

```
GAATCAGTTT AGGTGTGGTA GGGCAGGTTG                                30
```

(2) INFORMATION FOR SEQ ID NO:232:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:232:

```
TAGCTGCTCG TGGTAGGGTA GGTTGGGGTA                                  30
```

(2) INFORMATION FOR SEQ ID NO:233:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:233:

```
GCGTAGTGCG CGCGACGAAC TGTGAAGCAC                                  30
```

(2) INFORMATION FOR SEQ ID NO:234:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:234:

```
GTGACTACTC TCACTCCTAT GGAACGGTCA                                  30
```

(2) INFORMATION FOR SEQ ID NO:235:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:235:

```
CGATGCGTGG TAGGGTAGGT TGGTGTCATT                                  30
```

(2) INFORMATION FOR SEQ ID NO:236:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:236:

```
GGTTATCGGT AGGTGTGGAT GGGCTACTTT                                  30
```

(2) INFORMATION FOR SEQ ID NO:237:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:237:

```
GCGTTTAGTT CGGGGTAGTG GTGGGTTGGA                                  30
```

(2) INFORMATION FOR SEQ ID NO:238:

(i) SEQUENCE CHARACTERISTICS:
        (A) LENGTH:  30 base pairs
        (B) TYPE: nucleic acid
        (C) STRANDEDNESS: single
        (D) TOPOLOGY: linear (xi) SEQUENCE DESCRIPTION: SEQ ID NO:238:

```
GGGAGTGGTA GGAGTAGGGT TGGAGCCGTA                                  30
```

(2) INFORMATION FOR SEQ ID NO:239:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:239:

```
GTGAATAGGT AGGGTCGGAT AGGCTACGGT                                    30
```

(2) INFORMATION FOR SEQ ID NO:240:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (xi) SEQUENCE DESCRIPTION: SEQ ID NO:240:

```
AGATGCCTGT CGAGCATGCT NNNNNNNNNN NNNNNNNNNN NNNNNNNNNN              50

NNNNNNNNNN NNNNNNNNNN NNNNNNNNNN GTAGCTAAAC TGCTTTGTCG             100

ACGGG                                                              105
```

(2) INFORMATION FOR SEQ ID NO:241:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:241:

```
GCAAAGCCGG GGAAGTCCCA GTGGTAGGCT GAGGGTTGGG GGATTGAAAT              50

CCCTGTGGAC                                                          60
```

(2) INFORMATION FOR SEQ ID NO:242:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:242:

```
GACGGGCCAG GGAGGTGGCA GCAGGGATGG GTTAGTGGTA GGCGCTGCAA              50

CTCAGGATTG                                                          60
```

(2) INFORMATION FOR SEQ ID NO:243:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (xi) SEQUENCE DESCRIPTION: SEQ ID NO:243:

```
AGCTGTCGTC GTGCCGCGTG GTGAGGGTTG ATGCGTGGGT AGGCTAGTCC              50

CATGGCGA                                                            58
```

(2) INFORMATION FOR SEQ ID NO:244:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (xi) SEQUENCE DESCRIPTION: SEQ ID NO:244:

CTGCGGGTGG GACGGAGCGT GGTAGGGCAG GTTGGAGTCG TAGTCTCACG        50

GGCCTGGGCA                                                   60

(2) INFORMATION FOR SEQ ID NO:245:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (xi) SEQUENCE DESCRIPTION: SEQ ID NO:245:

TGGTCGTAGC TGCTAGGTGA AGGTATGGCC GGGGTAGTGG TGGGTTGGGG        50

TGCGATGCAG                                                   60

(2) INFORMATION FOR SEQ ID NO:246:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (xi) SEQUENCE DESCRIPTION: SEQ ID NO:246:

GGCGGCGTTG GTGTAGTGGC GCACTGTGGT TGGGCGGAGA GGCTAGGAGT        50

GCATGATGCC                                                   60

(2) INFORMATION FOR SEQ ID NO:247:

(i) SEQUENCE CHARACTERISTICS:
            (A) LENGTH: 59 base pairs
            (B) TYPE: nucleic acid
            (C) STRANDEDNESS: single
            (D) TOPOLOGY: linear (xi) SEQUENCE DESCRIPTION: SEQ ID NO:247:

AAGGCCTGGA GCCGGTTGGT TGCGGGGGGT AGGCTAGGTG TGCATGATGC        50

TACCCCACG                                                    59

(2) INFORMATION FOR SEQ ID NO:248:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (xi) SEQUENCE DESCRIPTION: SEQ ID NO:248:

CCGTGCATCA ACCGTGCGAC GCTGGTTTGC TGTGGTAGGG GAGGATGGAC        50

CCAGGAGTGG                                                   60

(2) INFORMATION FOR SEQ ID NO:249:

(i) SEQUENCE CHARACTERISTICS:
            (A) LENGTH: 60 base pairs
            (B) TYPE: nucleic acid
            (C) STRANDEDNESS: single (D) TOPOLOGY: linear (xi) SEQUENCE DESCRIPTION: SEQ ID NO:249:

AGCCGATGTT GCGGTGGATA CTCGGATTGG TAGGGCAGGT TGGGCTCGGA         50

TGAGCTCGGA                                                    60

(2) INFORMATION FOR SEQ ID NO:250:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:250:

TGAGCAGGTG GTAGGGTTAG GGTTGGGTCG CTGAGGCGTC CTGATCACGC         50

GCGGGTGAGG                                                    60

(2) INFORMATION FOR SEQ ID NO:251:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:251:

GGCAGTGCGT CTTCTGGCAA GGTGTGTGTT GCGGAGAGGG TAGGTGTGGA         50

TGATGCCGGA                                                    60

(2) INFORMATION FOR SEQ ID NO:252:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:252:

CTAGCGGCTG GTAGGGGAGG TTGGGAGTGG TGACTCCCGC TGGGCGTGAT         50

TCGTGCAGGG                                                    60

(2) INFORMATION FOR SEQ ID NO:253:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:253:

CTGCGGGTGG GACGGAGCGT GGTAGGGCAG GTTGGAGTCG TAGTCTCACG         50

GGCCCGGGCA                                                    60

(2) INFORMATION FOR SEQ ID NO:254:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:254:

```
GCAGTAGGGA GCACGCGGGC CTAGGGTAGG TGTGGATGAT GCGGGCAGGC          50

GGTGCGACTT                                                       60

(2) INFORMATION FOR SEQ ID NO:255:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO:255:

GGAAGCTGGG GCAGCGTAGG AGTAGGGATG GGCGAGTGGT AGGCGCGGTT          50

CGCTGTGCA                                                        59

(2) INFORMATION FOR SEQ ID NO:256:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:256:

CTTTGGAGAC AGTCCGTGGT AGGGCAGGTT GGGGTGACTT CGTGGAAGAA          50

GCGAGACGGT                                                       60

(2) INFORMATION FOR SEQ ID NO:257:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:257:

GATGGATAAC ACGTGGCCGG GGAGCGTGGT AGGGTAGGAT GGTGTCGATT          50

GCGCCAGGTG                                                       60

(2) INFORMATION FOR SEQ ID NO:258:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:258:

CGGAGCCGGG GTAGTGGTGG GATGGGGGCG TAGGACATGG CAAGTGCGGT          50

GTAGCCGTGG                                                       60

(2) INFORMATION FOR SEQ ID NO:259:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO:259:

GCAAGCGTTC GGTGTTGAGT GTAGGTAGGT CTTTGGTTGG GTCGTGTCGT          50

CCACTGTTC                                                        59
```

(2) INFORMATION FOR SEQ ID NO:260:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO:260:

```
GGCGTCGCAG AGGTAGCGTT GGTAGGGTAC GTTGGCTCTG AGGAGCCGCG          50

CCTCGTCCG                                                        59
```

(2) INFORMATION FOR SEQ ID NO:261:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:261:

```
CCTGTGAGGG ACGGGGAGGA GTGAGGGTTG GGCGTGAGTC GCAGGGTGGT          50

AGGCCACTCC                                                       60
```

(2) INFORMATION FOR SEQ ID NO:262:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:262:

```
GACGGGTGCA GCGCGGGAGC GTGGTAGGGA AGGTTGGGGT CTTCAGCGCT          50

GTGTTGGGCC                                                       60
```

(2) INFORMATION FOR SEQ ID NO:263:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO:263:

```
CAGCAATGAG GGCTGGCGGA GTGTGGTAGG GTAGGTTGGT GTGGAGGGAG          50

CACGGTGGT                                                        59
```

(2) INFORMATION FOR SEQ ID NO:264:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:264:

```
GGCGTCCGAT GATTCAGGTC GTGGTAGGCA TTGAGGGATG GGGTCCTGTG          50

GGACTGGCCT                                                       60
```

(2) INFORMATION FOR SEQ ID NO:265:

(i) SEQUENCE CHARACTERISTICS:

(A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:265:

GCAGTAGGGA GCATGCGGGC CTAGGGTAGG TGTGGATGAT GCGGGCAGGC          50

GGTGCGACTT                                                    60

(2) INFORMATION FOR SEQ ID NO:266:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:266:

GATTGCAATC ACTCTGGCGG AGTTGGTAGG GGAGGTTGGG CGCGGTAGGG          50

CCGTAGCCAG                                                    60

(2) INFORMATION FOR SEQ ID NO:267:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:267:

GAGACGTTGG TAGGGGTGGT TGGGCCTCGG TGGAGGTCGT CGAAGGCAGG          50

GGAGTGTCGG                                                    60

(2) INFORMATION FOR SEQ ID NO:268:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:268:

GGAACCGCGG AGGGCGTAGG GTTGGAGGCG TTGGCCGATG TGGTAGGCAC          50

GGACTCGGAT                                                    60

(2) INFORMATION FOR SEQ ID NO:269:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:269:

TGTTTCGAGT TGGCGGCAGG TGGTAGGATC AGGGATGCGA GCCGAAGAAT          50

GTGTCGCCAC                                                    60

(2) INFORMATION FOR SEQ ID NO:270:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:270:

CGGGTAGTCG GAGGTTCGCG CTAGGCCGTG GTAGGGTAGG TTGGGGCGCC    50

TGAGCGGGCG    60

(2) INFORMATION FOR SEQ ID NO:271:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:271:

TGCTGTCGGC TGTTCGGACG GGCCTGGTAG GGGAGGTTGG GCATCGTAGG    50

ATGTGGCCCG    60

(2) INFORMATION FOR SEQ ID NO:272:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:272:

AGATGCCTGT CGAGCATGCT ACACCCGTGG TAGGGTAGGA TGGGGTGGTC    50

GTAGCTAAAC TGCTTTGTCG ACGGG    75

(2) INFORMATION FOR SEQ ID NO:273:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:273:

AGATGCCTGT CGAGCATGCT GTGAATAGGT AGGGTCGGAT GGGCTACGGT    50

GTAGCTAAAC TGCTTTGTCG ACGGG    75

(2) INFORMATION FOR SEQ ID NO:274:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:274:

AGATGCCTGT CGAGCATGCT GCCGCTACGA GGGTAGGTGT GGATGCTGCC    50

GTAGCTAAAC TGCTTTGTCG ACGGG    75

(2) INFORMATION FOR SEQ ID NO:275:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:275:

AGATGCCTGT CGAGCATGCT GTTGTGGTAG GGTTAGGGAT GGTAGCGGTT    50

```
GTAGCTAAAC TGCTTTGTCG ACGGG                                               75

(2) INFORMATION FOR SEQ ID NO:276:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:276:

AGATGCCTGT CGAGCATGCT GGGAGTGGTA GGAGTAGGGT TGGAGCCGTA                    50

GTAGCTAAAC TGCTTTGTCG ACGGG                                               75

(2) INFORMATION FOR SEQ ID NO:277:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (xi) SEQUENCE DESCRIPTION: SEQ ID NO:277:

AGATGCCTGT CGAGCATGCT GGCGGCGTTG GTGTAGTGGC GCACTGTGGT                    50

TGGGCGGAGA GGCTAGGAGT GCATGATGCC GTAGCTAAAC TGCTTTGTCG                   100

ACGGG                                                                   105

(2) INFORMATION FOR SEQ ID NO:278:

(i) SEQUENCE CHARACTERISTICS:
        (A) LENGTH: 101 base pairs
        (B) TYPE: nucleic acid
        (C) STRANDEDNESS: single
        (D) TOPOLOGY: linear (xi) SEQUENCE DESCRIPTION: SEQ ID NO:278:

AGATGCCTGT CGAGCATGCT CTTTGGAGAC AGTCCGTGGT AGGGCAGGTT                    50

GGGGTGACTT CGTGGAAGAA GCGAGACGGT GTAGCTAAAC TGCTTTGTCG                   100

A                                                                       101

(2) INFORMATION FOR SEQ ID NO:279:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:279:

CAGTCCGTGG TAGGGCAGGT TGGGGTGACT TCGTGGAA                                 38

(2) INFORMATION FOR SEQ ID NO:280:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (xi) SEQUENCE DESCRIPTION: SEQ ID NO:280:

AGATGCCTGT CGAGCATGCT GGCGTCCGAT GATTCAGGTC GTGGTAGGCA                    50

TTGAGGGATG GGTCCTGTG GGACTGGCCT GTAGCTAAAC TGCTTTGTCG                    100
```

ACGGG                                                             105

(2) INFORMATION FOR SEQ ID NO:281:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:281:

GGGAGCUCAG AAUAAACGCU CAAUGCUAUU CGCCUAACUC GGCGCUCCUA            50

CCUUUCGACA UGAGGCCCGG AUCCGGC                                     77

(2) INFORMATION FOR SEQ ID NO:282:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:282:

GGGAGCUCAG AAUAAACGCU CAAAUCUCCU CCCGUCGAAG CUAACCUGGC            50

CACUUCGACA UGAGGCCCGG AUCCGGC                                     77

(2) INFORMATION FOR SEQ ID NO:283:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:283:

GGGAGCUCAG AAUAAACGCU CAAUCGGCGA GCUAACCAAG ACACUCGCUG            50

CACUUCGACA UGAGGCCCGG AUCCGGC                                     77

(2) INFORMATION FOR SEQ ID NO:284:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:284:

GGGAGCUCAG AAUAAACGCU CAAGUAGCAC UAUCGGCCUA ACCCGGUAGC            50

UCCUUCGACA UGAGGCCCGG AUCCGGC                                     77

(2) INFORMATION FOR SEQ ID NO:285:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:285:

GGGAGCUCAG AAUAAACGCU CAAACCCGCG GCCUCCGAAG CUAACCAGGA            50

CACUUCGACA UGAGGCCCGG AUCCGGC                                     77

(2) INFORMATION FOR SEQ ID NO:286:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:286:

GGGAGCUCAG AAUAAACGCU CAAUGGGUGC UAACCAGGAC ACACCCACGC           50

UGUUUCGACA UGAGGCCCGG AUCCGGC                                   77

(2) INFORMATION FOR SEQ ID NO:287:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:287:

GGGAGCUCAG AAUAAACGCU CAACACGCAC AGCUAACCAA GCCACUGUGC           50

CCCUUCGACA UGAGGCCCGG AUCCGGC                                   77

(2) INFORMATION FOR SEQ ID NO:288:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:288:

GGGAGCUCAG AAUAAACGCU CAACUGCGUG GUAUAACCAC AUGCCCUGGG           50

CGAUUCGACA UGAGGCCCGG AUCCGGC                                   77

(2) INFORMATION FOR SEQ ID NO:289:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:289:

GGGAGCUCAG AAUAAACGCU CAAUGGGUGC UUAACCAGGC CACACCCUGC           50

UGUUUCGACA UGAGGCCCGG AUCCGGC                                   77

(2) INFORMATION FOR SEQ ID NO:290:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:290:

GGGAGCUCAG AAUAAACGCU CAACUAGGUG CUAUCCAGGA CUCUCCCUGG           50

UCCUUCGACA UGAGGCCCGG AUCCGGC                                   77

(2) INFORMATION FOR SEQ ID NO:291:

(i) SEQUENCE CHARACTERISTICS:
        (A) LENGTH: 77 base pairs (B) TYPE: nucleic acid
              (C) STRANDEDNESS: single
              (D) TOPOLOGY: linear (xi) SEQUENCE DESCRIPTION: SEQ ID NO:291:

GGGAGCUCAG AAUAAACGCU CAAUGCUAUU CGCCUAGCUC GGCGCUCCUA          50

CCUUUCGACA UGAGGCCCGG AUCCGGC                                  77

(2) INFORMATION FOR SEQ ID NO:292:

(i) SEQUENCE CHARACTERISTICS:
              (A) LENGTH: 77 base pairs
              (B) TYPE: nucleic acid
              (C) STRANDEDNESS: single
              (D) TOPOLOGY: linear (xi) SEQUENCE DESCRIPTION: SEQ ID NO:292:

GGGAGCUCAG AAUAAACGCU CAAAGCUAUU CGCCCAACCC GGCGCUCCCG          50

ACCUUCGACA UGAGGCCCGG AUCCGGC                                  77

(2) INFORMATION FOR SEQ ID NO:293:

(i) SEQUENCE CHARACTERISTICS:
              (A) LENGTH: 76 base pairs
              (B) TYPE: nucleic acid
              (C) STRANDEDNESS: single
              (D) TOPOLOGY: linear (xi) SEQUENCE DESCRIPTION: SEQ ID NO:293:

GGGAGCUCAG AAUAAACGCU CAAACCAGCU GCGUGCAACC GCACAUGCCU          50

GGUUCGACAU GAGGCCCGGA UCCGGC                                   76

(2) INFORMATION FOR SEQ ID NO:294:

(i) SEQUENCE CHARACTERISTICS:
              (A) LENGTH: 77 base pairs
              (B) TYPE: nucleic acid
              (C) STRANDEDNESS: single
              (D) TOPOLOGY: linear (xi) SEQUENCE DESCRIPTION: SEQ ID NO:294:

GGGAGCUCAG AAUAAACGCU CAACAGGCCC CGUCGUAAGC UAACCUGGAC          50

CCUUUCGACA UGAGGCCCGG AUCCGGC                                  77

(2) INFORMATION FOR SEQ ID NO:295:

(i) SEQUENCE CHARACTERISTICS:
              (A) LENGTH: 77 base pairs
              (B) TYPE: nucleic acid
              (C) STRANDEDNESS: single
              (D) TOPOLOGY: linear (xi) SEQUENCE DESCRIPTION: SEQ ID NO:295:

GGGAGCUCAG AAUAAACGCU CAAGGGUAAC GUUGUGACAA GUACACCUGC          50

GUCUUCGACA UGAGGCCCGG AUCCGGC                                  77

(2) INFORMATION FOR SEQ ID NO:296:

(i) SEQUENCE CHARACTERISTICS:
              (A) LENGTH: 77 base pairs
              (B) TYPE: nucleic acid
              (C) STRANDEDNESS: single
              (D) TOPOLOGY: linear (xi) SEQUENCE DESCRIPTION: SEQ ID NO:296:

GGGAGCUCAG AAUAAACGCU CAAGGGGCAA CGCUACAGAC AAGUGCACCC          50

AACUUCGACA UGAGGCCCGG AUCCGGC                                   77

(2) INFORMATION FOR SEQ ID NO:297:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:297:

GGGAGCUCAG AAUAAACGCU CAACGUCAGA AGGCAACGUA UAGGCAAGCA          50

CACUUCGACA UGAGGCCCGG AUCCGGC                                   77

(2) INFORMATION FOR SEQ ID NO:298:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:298:

GGGAGCUCAG AAUAAACGCU CAACCUCUCG AAGACAACGC UGUGACAAGA          50

CACUUCGACA UGAGGCCCGG AUCCGGC                                   77

(2) INFORMATION FOR SEQ ID NO:299:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:299:

GGGAGCUCAG AAUAAACGCU CAAAGUGGGA AACGCUACUU GACAAGACAC          50

CACUUCGACA UGAGGCCCGG AUCCGGC                                   77

(2) INFORMATION FOR SEQ ID NO:300:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:300:

GGGAGCUCAG AAUAAACGCU CAAGGCUACG CUAAUGACAA GUGCACUUGG          50

GUGUUCGACA UGAGGCCCGG AUCCGGC                                   77

(2) INFORMATION FOR SEQ ID NO:301:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:301:

GGGAGAUGCC UGUCGAGCAU GCUGCUCUGG UAACGCAAUG UCAAGUGCAC          50

```
AUGAGUAGCU AAACAGCUUU GUCGACGGG                                        79

(2) INFORMATION FOR SEQ ID NO:302:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:302:

GGGAGAUGCC UGUCGAGCAU GCUGAGCCGC AGGUAACGGA CCGGCGAGAC               50

CAUUGUAGCU AAACAGCUUU GUCGACGGG                                        79

(2) INFORMATION FOR SEQ ID NO:303:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:303:

GGGAGAUGCC UGUCGAGCAU GCUGACGAGC UUCGUAACGC UAUCGACAAG               50

UGCAGUAGCU AAACAGCUUU GUCGACGGG                                        79

(2) INFORMATION FOR SEQ ID NO:304:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:304:

GGGAGAUGCC UGUCGAGCAU GCUGAAGGGG AAACGUUGAG UCCGGUACAC               50

CCUGGUAGCU AAACAGCUUU GUCGACGGG                                        79

(2) INFORMATION FOR SEQ ID NO:305:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:305:

GGGAGAUGCC UGUCGAGCAU GCUGAGGGUA ACGUACUGGC AAGCUCACCU               50

CAGCGUAGCU AAACAGCUUU GUCGACGGG                                        79

(2) INFORMATION FOR SEQ ID NO:306:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:306:

GGGAGAUGCC UGUCGAGCAU GCUGGAGGUA ACGUACGACA AGACCACUCC               50

AACUGUAGCU AAACAGCUUU GUCGACGGG                                        79

(2) INFORMATION FOR SEQ ID NO:307:
```

(i) SEQUENCE CHARACTERISTICS:
    (A) LENGTH: 79 base pairs
    (B) TYPE: nucleic acid
    (C) STRANDEDNESS: single
    (D) TOPOLOGY: linear (xi) SEQUENCE DESCRIPTION: SEQ ID NO:307:

GGGAGAUGCC UGUCGAGCAU GCUGAGGUAA CGCUGAGUCA AGUGCACUCG        50

ACAUGUAGCU AAACAGCUUU GUCGACGGG                              79

(2) INFORMATION FOR SEQ ID NO:308:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:308:

GGGAGAUGCC UGUCGAGCAU GCUGGGGAAA CGCUAUCGAC GAGUGCACCC        50

GGCAGUAGCU AAACAGCUUU GUCGACGGG                              79

(2) INFORMATION FOR SEQ ID NO:309:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:309:

GGGAGAUGCC UGUCGAGCAU GCUGCCGAGG GUAACGUUGG GUCAAGCACA        50

CCUCGUAGCU AAACAGCUUU GUCGACGGG                              79

(2) INFORMATION FOR SEQ ID NO:310:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:310:

GGGAGAUGCC UGUCGAGCAU GCUGUCGGGG UAACGUAUUG GCAAGGCACC        50

CGACGUAGCU AAACAGCUUU GUCGACGGG                              79

(2) INFORMATION FOR SEQ ID NO:311:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:311:

GGGAGAUGCC UGUCGAGCAU GCUGGGUAAC GCUGUGGACA AGUGCACCAG        50

CUGCGUAGCU AAACAGCUUU GUCGACGGG                              79

(2) INFORMATION FOR SEQ ID NO:312:

(i) SEQUENCE CHARACTERISTICS:
        (A) LENGTH: 79 base pairs
        (B) TYPE: nucleic acid

```
            (C) STRANDEDNESS: single
            (D) TOPOLOGY: linear (xi) SEQUENCE DESCRIPTION: SEQ ID NO:312:

GGGAGAUGCC UGUCGAGCAU GCUGAGGGUA ACGUACUGGC AAGCUCACCU           50

CAGCGUAGCU AAACAGCUUU GUCGACGGG                                  79

(2) INFORMATION FOR SEQ ID NO:313:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:313:

GGGAGAUGCC UGUCGAGCAU GCUGAGGGUA ACGUAUAGUC AAGACACCUC           50

AAGUGUAGCU AAACAGCUUU GUCGACGGG                                  79

(2) INFORMATION FOR SEQ ID NO:314:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:314:

GGGAGAUGCC UGUCGAGCAU GCUGGGGUAA CGCAUUGGCA AGACACCCAG           50

CCCCGUAGCU AAACAGCUUU GUCGACGGG                                  79

(2) INFORMATION FOR SEQ ID NO:315:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:315:

GGGAGAUGCC UGUCGAGCAU GCUGGAGGAA ACGUACCGUC GAGCCACUCC           50

AUGCGUAGCU AAACAGCUUU GUCGACGGG                                  79

(2) INFORMATION FOR SEQ ID NO:316:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:316:

GGGAGAUGCC UGUCGAGCAU GCUGAGGUAA CGCUGAGUCA AGUGCACUCG           50

ACAUGUAGCU AAACAGCUUU GUCGACGGG                                  79

(2) INFORMATION FOR SEQ ID NO:317:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:317:
```

```
GGGAGAUGCC UGUCGAGCAU GCUGGGGUAA CGUGUGACAA GAUCACCCAG        50

UUUGGUAGCU AAACAGCUUU GUCGACGGG                               79

(2) INFORMATION FOR SEQ ID NO:318:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:318:

GGGAGAUGCC UGUCGAGCAU GCUGCACAGG GCAACGCUGC UGACAAGUGC        50

ACCUGUAGCU AAACAGCUUU GUCGACGGG                               79

(2) INFORMATION FOR SEQ ID NO:319:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:319:

GGGAGCUCAG AAUAAACGCU CAAUGGGUGC UAACCACCAC ACACUCACGC        50

UGUUUCGACA UGAGGCCCGG AUCCGGC                                 77

(2) INFORMATION FOR SEQ ID NO:320:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO:320:

CGAGCAUGCU GNNNNNNNNN NNNNNNNNNN NNNNNNNNNN NGUAGCUAAA        50

CAGCUUUGUC GACGGG                                             66

(2) INFORMATION FOR SEQ ID NO:321:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:321:

ATCCGCCTGA TTAGCGATAC T                                       21

(2) INFORMATION FOR SEQ ID NO:322:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:322:

ATCCGCCTGA TTAGCGATAC TNNNNNNNNN NNNNNNNNNN NNNNNNNNNN        50

NNNNNNNNNN NACTTGAGCA AAATCACCTG CAGGGG                       86
```

(2) INFORMATION FOR SEQ ID NO:323:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ix) FEATURE:
        (A) NAME/KEY: N
        (B) LOCATION: 26-28
        (D) OTHER INFORMATION: The N = biotin (xi) SEQUENCE DESCRIPTION: SEQ ID NO:323:

TGAACTCGTT TTAGTGGACG TCCCCNNN                                28

(2) INFORMATION FOR SEQ ID NO:324:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:324:

CTACCTACGA TCTGACTAGC                                         20

(2) INFORMATION FOR SEQ ID NO:325:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (xi) SEQUENCE DESCRIPTION: SEQ ID NO:325:

CTACCTACGA TCTGACTAGC NNNNNNNNNN NNNNNNNNNN NNNNNNNNNN         50

NNNNNNNNNN NNTAGCTTAC TCTCATGTAT TCC                           83

(2) INFORMATION FOR SEQ ID NO:326:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ix) FEATURE:
        (A) NAME/KEY: N
        (B) LOCATION: 22 and 24
        (D) OTHER INFORMATION: The N = biotin (xi) SEQUENCE DESCRIPTION: SEQ ID NO:326:

ATCGAATGAG AGTACATAAG GNANA                                   25

(2) INFORMATION FOR SEQ ID NO:327:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:327:

GGGAGGACGA TGCGG                                              15

(2) INFORMATION FOR SEQ ID NO:328:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:328:

GGGAGGACGA TGCGGNNNNN NNNNNNNNNN NNNNNNNNNN NNNNNCAGAC         50

GACGACGGGG A                                                   61

(2) INFORMATION FOR SEQ ID NO:329:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: N
        (B) LOCATION: 17 and 19
        (D) OTHER INFORMATION: The N = biotin (xi) SEQUENCE DESCRIPTION: SEQ ID NO:329:

GTCTGCTGCT GCCCCTNANA                                          20

(2) INFORMATION FOR SEQ ID NO:330:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:330:

ATCCGCCTGA TTAGCGATAC TGTGCGATTA GGGGCTATGC AAATCCGACT         50

ATCAGAAGGC TACTTGAGCA AAATCACCTG CAGGGG                        86

(2) INFORMATION FOR SEQ ID NO:331:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO:331:

ATCCGCCTGA TTAGCGATAC TAAGGCCAGG GCTATGCAAA TCGCGGCGCC         50

TATGGCCATT ACTTGAGCAA AATCACCTGC AGGGG                         85

(2) INFORMATION FOR SEQ ID NO:332:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (xi) SEQUENCE DESCRIPTION: SEQ ID NO:332:

ATCCGCCTGA TTAGCGATAC TAGGCCAGGG CTATGCAAAT CGCGGCGCCT         50

ATGGCCATTA CTTGAGCAAA ATCACCTGCA GGGG                          84

(2) INFORMATION FOR SEQ ID NO:333:

(i) SEQUENCE CHARACTERISTICS:

```
        (A) LENGTH: 84 base pairs
        (B) TYPE: nucleic acid
        (C) STRANDEDNESS: single
        (D) TOPOLOGY: linear (xi) SEQUENCE DESCRIPTION: SEQ ID NO:333:

ATCCGCCTGA TTAGCGATAC TCGGCAGGGC TATGCAAATC GCGGCGCCTA            50

TGGCCATTGA CTTGAGCAAA ATCACCTGCA GGGG                             84

(2) INFORMATION FOR SEQ ID NO:334:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:334:

ATCCGCCTGA TTAGCGATAC TAGGGGCTGT GCAGACCATG GCGACCATCG            50

GGATCCGTGC TACTTGAGCA AAATCACCTG CAGGGG                           86

(2) INFORMATION FOR SEQ ID NO:335:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:335:

ATCCGCCTGA TTAGCGATAC TAGGGGCTGT GCAAACCATG GCGACCATCG            50

GGATCCGTGC TACTTGAGCA AAATCACCTG CAGGGG                           86

(2) INFORMATION FOR SEQ ID NO:336:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (xi) SEQUENCE DESCRIPTION: SEQ ID NO:336:

ATCCGCCTGA TTAGCGATAC TGCTCTCGGG GCTTTTGCAA AATCNGTAGA            50

CCTACGAGGC AGACTTGAGC AAAATCACCT GCAGGGG                          87

(2) INFORMATION FOR SEQ ID NO:337:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (xi) SEQUENCE DESCRIPTION: SEQ ID NO:337:

ATCCGCCTGA TTAGCGATAC TCGTTGCTCA TAGGGGCTTT GCAAAATCGT            50

ATAACTCGTA CTACTTGAGC AAAATCACCT GCAGGGG                          87

(2) INFORMATION FOR SEQ ID NO:338:

(i) SEQUENCE CHARACTERISTICS:
        (A) LENGTH: 86 base pairs
        (B) TYPE: nucleic acid
        (C) STRANDEDNESS: single
        (D) TOPOLOGY: linear
```

(xi) SEQUENCE DESCRIPTION: SEQ ID NO:338:

ATCCGCCTGA TTAGCGATAC TCAAGGGGCT TTGCAAAATG ACAAGCCTAA          50

AGCTTGACAC TACTTGAGCA AAATCACCTG CAGGGG                         86

(2) INFORMATION FOR SEQ ID NO:339:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:339:

ATCCGCCTGA TTAGCGATAC TAGTGGGGCT ATGCAAATTA TCGCCTAGTG          50

GCTGATACTA CACTTGAGCA AAATCACCTG CAGGGG                         86

(2) INFORMATION FOR SEQ ID NO:340:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:340:

RGGGCTNTGC AAAN                                                 14

(2) INFORMATION FOR SEQ ID NO:341:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:341:

AGGCCAGGGC TATGCAAATC GCGGCGCCTA TGGCC                          35

(2) INFORMATION FOR SEQ ID NO:342:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:342:

CTACCTACGA TCTGACTAGC AGGGCTTTGT AAACATGGAC TACGTACACT          50

ATGCAGGCAA TAGCTTACTC TCATGTATTC C                              81

(2) INFORMATION FOR SEQ ID NO:343:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:343:

CTACCTACGA TCTGACTAGC TAGCGGGGCT TTGCAAAAAA CGAGTTGTAG          50

TTCTACGCAA TAGCTTACTC TCATGTATTC C                              81

(2) INFORMATION FOR SEQ ID NO:344:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:344:

```
CTACCTACGA TCTGACTAGC AGGGCTTTGT AAACATGGAC TACGTACACT        50

ATGCAGGCAA TAGCTTACTC TCATGTATTC C                           81
```

(2) INFORMATION FOR SEQ ID NO:345:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (xi) SEQUENCE DESCRIPTION: SEQ ID NO:345:

```
CTACCTACGA TCTGACTAGC AGGGCTTTGT AAACATGGAC TACGTACACT        50

ATGCAGGCAT AGCTTACTCT CATGTATTCC                             80
```

(2) INFORMATION FOR SEQ ID NO:346:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (xi) SEQUENCE DESCRIPTION: SEQ ID NO:346:

```
CTACCTACGA TCTGACTAGC GGGGCTCTGC AAAGTCTGAA ATGACCACGC        50

CAGTCGCTAG CTTACTCTCA TGTATTCC                               78
```

(2) INFORMATION FOR SEQ ID NO:347:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:347:

```
CTACCTACGA TCTGACTAGC AGGGCTGTGT AAACTGGTGC TAGCTTACTC        50

TCATGTATTC C                                                 61
```

(2) INFORMATION FOR SEQ ID NO:348:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (xi) SEQUENCE DESCRIPTION: SEQ ID NO:348:

```
CTACCTACGA TCTGACTAGC AGGGCTTTGT AAACATGGAC TACGTACACT        50

ATGCAGGTAG CTTACTCTCA TGTATTCC                               78
```

(2) INFORMATION FOR SEQ ID NO:349:

(i) SEQUENCE CHARACTERISTICS:
        (A) LENGTH: 75 base pairs (B) TYPE: nucleic acid
        (C) STRANDEDNESS: single
        (D) TOPOLOGY: linear (xi) SEQUENCE DESCRIPTION: SEQ ID NO:349:

CTACCTACGA TCTGACTAGC GCGGCGGGGC TTTGGAAAAT CGACATACTC          50

GACTTAGCTT ACTCTCATGT ATTCC                                    75

(2) INFORMATION FOR SEQ ID NO:350:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:350:

CTACCTACGA TCTGACTAGC AGGGCTTTGT AAACATGGAC TACGTACACT          50

ATGCTAGCTT ACTCTCATGT ATTCC                                    75

(2) INFORMATION FOR SEQ ID NO:351:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:351:

GCRGGGCTNT GYAAAN                                              16

(2) INFORMATION FOR SEQ ID NO:352:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:352:

GGGAGGACGA TGCGGGGGGC TTTGCAAAAA TTGTTAAATC TACCCCAGAC          50

GACGACGGGG A                                                   61

(2) INFORMATION FOR SEQ ID NO:353:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:353:

GGGAGGACGA TGCGGGGCTA TGTAAATTAC TGCTGTACTA CGCATCAGAC          50

GACGACGGGG A                                                   61

(2) INFORMATION FOR SEQ ID NO:354:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO:354:

GGGAGGACGA TGCGGGGGGG GCTCTGTAAA GTCTTTCAAC TACCACCAGA        50

CGACGACGGG GA        62

(2) INFORMATION FOR SEQ ID NO:355:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:355:

GGGAGGACGA TGCGGGGGCT CTGCAAAGTG AAATCCCCAC TACCGCAGAC        50

GACGACGGGG A        61

(2) INFORMATION FOR SEQ ID NO:356:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:356:

GGGAGGACGA TGCGGGGGGC TCTGCAAAGT TTCGTTAACT ACCTGCAGAC        50

GACGACGGGG A        61

(2) INFORMATION FOR SEQ ID NO:357:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:357:

GGGAGGACGA TGCGGGGCTA CGTACGGGGG CTTTGTAAAA CCCCGCAGAC        50

GACGACGGGG A        61

(2) INFORMATION FOR SEQ ID NO:358:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:358:

GGGAGGACGA TGCGGGGGCT ATGCAAATTT TCCAAACTAC TGCATCAGAC        50

GACGACGGGG A        61

(2) INFORMATION FOR SEQ ID NO:359:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:359:

GGGAGGACGA TGCGGGGCTA CGTACCGGGG CTTTGTAAAA CCCCGCAGAC        50

GACGACGGGG A        61

(2) INFORMATION FOR SEQ ID NO:360:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:360:

```
GGGAGGACGA TGCGGGGCTC TGCAAAGGAC ACAGGTCCTA CGCATCAGAC        50

GACGACGGGG A                                                  61
```

(2) INFORMATION FOR SEQ ID NO:361:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:361:

```
GGGAGGACGA TGCGGGGCTC TGCAAATCCT CCTCGGGAGG CTACGCAGAC        50

GACGACGGGG A                                                  61
```

(2) INFORMATION FOR SEQ ID NO:362:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:362:

```
GGGAGGACGA TGCGGGGCTT TGTAAAATCT CATCTGAGAC TACGTCAGAC        50

GACGACGGGG A                                                  61
```

(2) INFORMATION FOR SEQ ID NO:363:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:363:

```
SSGGGGCTNT GCAAAN                                             16
```

(2) INFORMATION FOR SEQ ID NO:364:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:364:

```
GCGGGGCTAC GTACCGGGGC TTTGTAAAAC CCCGC                        35
```

(2) INFORMATION FOR SEQ ID NO:365:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:365:

GCGGGGCTAT GTAAATTACT GCTGTACTAC GCATC    35

(2) INFORMATION FOR SEQ ID NO:366:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:366:

ATCCGCCTGA TTAGCGATAC TGCTTCCCGA CGGAGCGTAG TCGACACAGC    50

CCCAATGTGA TACTTGAGCA AAATCACCTG CAGGGG    86

(2) INFORMATION FOR SEQ ID NO:367:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:367:

ATCCGCCTGA TTAGCGATAC TGACCACGAC TGATGCGTCG CCTCCCGATC    50

GGCAGTTACC CACTTGAGCA AAATCACCTG CAGGGG    86

(2) INFORMATION FOR SEQ ID NO:368:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:368:

ATCCGCCTGA TTAGCGATAC TGACCACGAC TGATGCGTCG CCTCCCGATA    50

GGCAGTTACT CACTTGAGCA AAATCACCTG CAGGGG    86

(2) INFORMATION FOR SEQ ID NO:369:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO:369:

ATCCGCCTGA TTAGCGATAC TTTAACACCT CAACTGGCAA CGTCCCGAAG    50

CTCCCGAGTC ACTTGAGCAA AATCACCTGC AGGGG    85

(2) INFORMATION FOR SEQ ID NO:370:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO:370:

ATCCGCCTGA TTAGCGATAC TGACCACGAC TGATGCGTCG CCTCCCGATA    50

GCTGTTACCC ACTTGAGCAA AATCACCTGC AGGGG    85

(2) INFORMATION FOR SEQ ID NO:371:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO:371:

```
ATCCGCCTGA TTAGCGATAC TTTAACACCT CAACTGGCAA CGTCCCGAAG          50

CTCCCGAGTC ACTTGAGCAA AATCACCTGC AGGGG                          85
```

(2) INFORMATION FOR SEQ ID NO:372:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:372:

```
ATCCGCCTGA TTAGCGATAC TGACCACGAC TGATGCGTCG CCTCCCGATA          50

GGCAGTTACC CACTTGAGCA AAATCACCTG CAGGGG                         86
```

(2) INFORMATION FOR SEQ ID NO:373:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO:373:

```
ATCCGCCTGA TTAGCGATAC TGACCACGAC TGNATGCGTC GCCTCCCGAT          50

AGCAGTTCCC ACTTGAGCAA AATCACCTGC AGGGG                          85
```

(2) INFORMATION FOR SEQ ID NO:374:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:374:

```
ATCCGCCTGA TTAGCGATAC TGCTTCCCGA CGGAGCGTAG TCGACACAGC          50

CCCAATGGGA TACTTGAGCA AAATCACCTG CAGGGG                         86
```

(2) INFORMATION FOR SEQ ID NO:375:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:375:

```
ATCCGCCTGA TTAGCGATAC TGACCACGAC TGATGCGTCG CCTCCCGATA          50

GGCAGTTACC CACTTGAGCA AAATCACCTG CAGGGG                         86
```

(2) INFORMATION FOR SEQ ID NO:376:

(i) SEQUENCE CHARACTERISTICS:
    (A) LENGTH: 86 base pairs
    (B) TYPE: nucleic acid
    (C) STRANDEDNESS: single
    (D) TOPOLOGY: linear (xi) SEQUENCE DESCRIPTION: SEQ ID NO:376:

ATCCGCCTGA TTAGCGATAC TAACACGGTC TGCTGCGACC CCTCGTACTA        50

ACGGTACCAG TACTTGAGCA AAATCACCTG CAGGGG                       86

(2) INFORMATION FOR SEQ ID NO:377:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (xi) SEQUENCE DESCRIPTION: SEQ ID NO:377:

ATCCGCCTGA TTAGCGATAC TTGGTGCTCG GGGAGAATTG GCTACGGACC        50

GCGGTTACCT ACACTTGAGC AAAATCACCT GCAGGGG                      87

(2) INFORMATION FOR SEQ ID NO:378:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:378:

CTACCTACGA TCTGACTAGC TGGAGGCGTT CCTGGACAGT TTCTGAGAGT        50

AGCTTACTCT CATGTATTCC                                         70

(2) INFORMATION FOR SEQ ID NO:379:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:379:

CTACCTACGA TCTGACTAGC TGGAGGCGTT CCTGGACAGT TTCTGAGAGC        50

TCTCCACCAA TAGCTTACTC TCATGTATTC C                            81

(2) INFORMATION FOR SEQ ID NO:380:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:380:

CTACCTACGA TCTGACTAGC TGGAGGCGTT CCTGGACAGT TTCTGAGAGC        50

TCTCCACCAA TAGCTTACTC TCATGTATTC C                            81

(2) INFORMATION FOR SEQ ID NO:381:

(i) SEQUENCE CHARACTERISTICS:
        (A) LENGTH: 81 base pairs
        (B) TYPE: nucleic acid
        (C) STRANDEDNESS: single (D) TOPOLOGY: linear (xi) SEQUENCE DESCRIPTION: SEQ ID NO:381:

CTACCTACGA TCTGACTAGC GAGGAAACTT CAGTGCCACA GCCATCCGTT            50

CGACGANGTA TAGCTTACTC TCATGTATTC C                               81

(2) INFORMATION FOR SEQ ID NO:382:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:382:

CTACCTACGA TCTGACTAGC ACGAGGAGTT TTAACGCCAC AGTGAAAGCG            50

GTTGACTTAT TAGCTTACTC TCATGTATTC C                               81

(2) INFORMATION FOR SEQ ID NO:383:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:383:

CTACCTACGA TCTGACTAGC TGGAGGCGTT CCTGGACAGT TTCTGAGATA            50

GCTTACTCTC ATGTATTCC                                             69

(2) INFORMATION FOR SEQ ID NO:384:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:384:

GGGAGGACGA TGCGGACGAT AGACGTCGAG GAATCTTTAG TGCCACAGAC            50

GACGACGGGG A                                                     61

(2) INFORMATION FOR SEQ ID NO:385:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:385:

GGGAGGACGA TGCGGCAGAG NGCAGGGCAC AAATCGGATC CTCGTCAGAC            50

GACGACGGGG A                                                     61

(2) INFORMATION FOR SEQ ID NO:386:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:386:

-continued

```
GGGAGGACGA TGCGGGACGA GGAGCTTTAG CGCCGCAGAA CAAACCAGAC        50

GACGACGGGG A                                                  61
```

(2) INFORMATION FOR SEQ ID NO:387:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:387:

```
GGGAGGACGA TGCGGCCCGA GGAGCTTTAG CGCCACAGGT TTGTGCAGAC        50

GACGACGGGG A                                                  61
```

(2) INFORMATION FOR SEQ ID NO:388:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:388:

```
GGGAGGACGA TGCGGGAGGA GCTTTAGCGC CGCGCCAGGG GCAATCAGAC        50

GACGACGGGG A                                                  61
```

(2) INFORMATION FOR SEQ ID NO:389:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:389:

```
GGGAGGACGA TGCGGCCACT GTACAGCTTA GTCACTCCTG CTTCCCAGAC        50

GACGACGGGG A                                                  61
```

(2) INFORMATION FOR SEQ ID NO:390:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:390:

```
CGAGGARYTT YARYGCCRCR G                                       21
```

(2) INFORMATION FOR SEQ ID NO:391:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:391:

```
CGAGGAGCTT TAGCGCCACA GGTT                                    24
```

(2) INFORMATION FOR SEQ ID NO:392:

(i) SEQUENCE CHARACTERISTICS:

(A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO:392:

ATCCGCCTGA TTAGCGATAC TTGAGTGCAT CGTCACCTCG ACCTACGGTC         50

CAGTTGGAAT ACTTGAGCAA AATCACCTGC AGGGG                         85

(2) INFORMATION FOR SEQ ID NO:393:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:393:

ATCCGCCTGA TTAGCGATAC TGCAAAGGCA CTTGGCCTGG TTAATAGGTT         50

CGCTGCCACA TACTTGAGCA AAATCACCTG CAGGGG                        86

(2) INFORMATION FOR SEQ ID NO:394:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:394:

ATCCGCCTGA TTAGCGATAC TACAAGGCAA CCCGGTACAT AGGTTCGCTT         50

AAACTGACAC GACTTGAGCA AAATCACCTG CAGGGG                        86

(2) INFORMATION FOR SEQ ID NO:395:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:395:

ATCCGCCTGA TTAGCGATAC TCTGACTGTG CGTCACCTCG GTCGAAAACC         50

CAGTAAACTC AACTTGAGCA AAATCACCTG CAGGGG                        86

(2) INFORMATION FOR SEQ ID NO:396:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:396:

ATCCGCCTGA TTAGCGATAC TCTGACTGTG CGTCACCTCG GTTGAAAACC         50

CAGTAAACTC AACTTGAGCA AAATCACCTG CAGGGG                        86

(2) INFORMATION FOR SEQ ID NO:397:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:397:

ATCCGCCTGA TTAGCGATAC TCAGCATGGC AAGATCTCCG GCGCGTGGTA          50

TCCCGTATCG TACTTGAGCA AAATCACCTG CAGGGG                         86

(2) INFORMATION FOR SEQ ID NO:398:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:398:

ATCCGCCTGA TTAGCGATAC TGCAAAGGCA CTTGGCCTGG TTAATAGGTT          50

CGCTGCCACA TACTTGAGCA AAATCACCTG CAGGGG                         86

(2) INFORMATION FOR SEQ ID NO:399:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:399:

CTACCTACGA TCTGACTAGC TACCACCATG TGCAGGCTTT CGCAGCCAAC          50

TGGGTCGTTA GCTTACTCTC ATGTATTCC                                 79

(2) INFORMATION FOR SEQ ID NO:400:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:400:

CTACCTACGA TCTGACTAGC CTCACTGACT GTCGCGTCAC CTCGACTGAA          50

AGTCCAGTTT TAGCTTACTC TCATGTATTC C                              81

(2) INFORMATION FOR SEQ ID NO:401:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:401:

CTACCTACGA TCTGACTAGC CAACTCTGGG AACACCCAGC AAGGTCCCTC          50

GCGTCACTTG TAGCTTACTC TCATGTATTC C                              81

(2) INFORMATION FOR SEQ ID NO:402:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO:402:

CTACCTACGA TCTGACTAGC ACTGCACACC GTTATGGAGG CTAGCTTACT          50

```
CTCATGTATT CC                                                           62

(2) INFORMATION FOR SEQ ID NO:403:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:403:

CTACCTACGA TCTGACTAGC ACTGAGTACC CAGAGTGCCC TCGGCCGCTG                  50

AATCGGACCA TAGCTTACTC TCATGTATTC C                                     81

(2) INFORMATION FOR SEQ ID NO:404:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:404:

GGGAGGACGA TGCGGTCCGC GGTATAAGGC CTAGGGTTTC GTTACCAGAC                  50

GACGACGGGG A                                                           61

(2) INFORMATION FOR SEQ ID NO:405:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:405:

GGGAGGACGA TGCGGCCTCG GCGGATTTCT TGGCACTCTC AGTAACAGAC                  50

GACGACGGGG A                                                           61

(2) INFORMATION FOR SEQ ID NO:406:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:406:

GGGAGGACGA TGCGGCCGCG GTTTGGGGCA TAGGGGCAAC ACATACAGAC                  50

GACGACGGGG A                                                           61

(2) INFORMATION FOR SEQ ID NO:407:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:407:

GGGAGGACGA TGCGGGCAGC GACCGCGGTA CAAGGCATAG GGTACAGACG                  50

ACGACGGGGA                                                             60
```

(2) INFORMATION FOR SEQ ID NO:408:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:408:

```
GGGAGGACGA TGCGGCGCAC AGTCCACGGT GCAAGGCCTG GGTCCAGACG            50

ACGACGGGGA                                                        60
```

(2) INFORMATION FOR SEQ ID NO:409:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:409:

```
GGGAGGACGA TGCGGCAGGG CGTTGTTACA AGTCGGACTC CCTCCAGACG            50

ACGACGGGGA T                                                      61
```

(2) INFORMATION FOR SEQ ID NO:410:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:410:

```
ATCCGCCTGA TTAGCGATAC TTGAGCAACT CGGCAGTTCC ACGGCAGATC            50

GCGTAATCCC CACTTGAGCA AAATCACCTG CAGGGG                           86
```

(2) INFORMATION FOR SEQ ID NO:411:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:411:

```
ATCCGCCTGA TTAGCGATAC TAGAGCAACT CGGCAGTTCC ACGGCAGATC            50

GCGTAATCCC CACTTGAGCA AAATCACCTG CAGGGG                           86
```

(2) INFORMATION FOR SEQ ID NO:412:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:412:

```
CTACCTACGA TCTGACTAGC AACGGATGTA ACACCTACCA TGCAGGTGCC            50

GCCCAAACAG                                                        60
```

(2) INFORMATION FOR SEQ ID NO:413:

(i) SEQUENCE CHARACTERISTICS:
        (A) LENGTH: 81 base pairs (B) TYPE: nucleic acid
        (C) STRANDEDNESS: single
        (D) TOPOLOGY: linear (xi) SEQUENCE DESCRIPTION: SEQ ID NO:413:

CTACCTACGA TCTGACTAGC ATACCTGACC ATAAGGTCCG AAGATCTCGC        50

GAGTACGTAT TAGCTTACTC TCATGTATTC C                           81

(2) INFORMATION FOR SEQ ID NO:414:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:414:

CTACCTACGA TCTGACTAGC CACCTGCATA GGAGTACCGA CTCCGATTGT        50

ATGTTAGCTT ACTCTCATGT ATTCC                                  75

(2) INFORMATION FOR SEQ ID NO:415:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:415:

CTACCTACGA TCTGACTAGC CACCTGCATA GGAGTACCGA CTCCGATTGT        50

ATGTCACCTA GCTTACTCTC ATGTATTCC                              79

(2) INFORMATION FOR SEQ ID NO:416:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:416:

GGGAGGACGA TGCGGAGGAC TCGTACCGCA CGGGTGACAC TCTGGCAGAC        50

GACGACGGGG A                                                 61

(2) INFORMATION FOR SEQ ID NO:417:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:417:

GGGAGGACGA TGCGGGGCAC GGAGACCACG GGAATTCCCA CAGCGCAGAC        50

GACGACGGGG A                                                 61

(2) INFORMATION FOR SEQ ID NO:418:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (xi) SEQUENCE DESCRIPTION: SEQ ID NO:418:

GGGAGGACGA TGCGGCCAGC TAGCGGAAGG GAAGTCTCGA CGAACATCAG            50

ACGACGACGG GGA                                                    63

(2) INFORMATION FOR SEQ ID NO:419:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:419:

GGGAGGACGA TGCGGGGGGG AGCGGAGACA CACCGGAATA TTCAACAGAC            50

GACGACGGGG A                                                      61

(2) INFORMATION FOR SEQ ID NO:420:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:420:

GCGGGGCTCT GCAAAGGACA CAGGTCCTAC GCATCAG                          37

(2) INFORMATION FOR SEQ ID NO:421:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO:421:

GGGAGGACGA TGCGGCCAGG TGGGGGATC ATCAGGGGTT TGTCGACAGA             50

CGACGACGGG GA                                                     62

(2) INFORMATION FOR SEQ ID NO:422:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:422:

GGGAGGACGA TGCGGCCAGC TAGCGGAAGG GAATCTGACG AACATCAGAC            50

GACGACGGGG A                                                      61

(2) INFORMATION FOR SEQ ID NO:423:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:423:

ATCCGCCTGA TTAGCGATAC TACACCCAAC CCCCTAAGAT TTTAGAGCAA            50

CTCGGCGCAA CACTTGAGCA AAATCACCTG CAGGGG                           86

(2) INFORMATION FOR SEQ ID NO:424:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (xi) SEQUENCE DESCRIPTION: SEQ ID NO:424:

```
ATCCGCCTGA TTAGCGATAC TCGAAGAGTA GGAGGCGATC CGCTCCGTAT          50

CAGGTCACAT AGGACTTGAG CAAAATCACC TGCAGGGG                       88
```

(2) INFORMATION FOR SEQ ID NO:425:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:425:

```
ATCCGCCTGA TTAGCGATAC TACACCCAAC CCCCTAAGAT TTTAGAGCAA          50

CTCGGCGCAA CACTTGAGCA AAATCACCTG CAGGGG                         86
```

(2) INFORMATION FOR SEQ ID NO:426:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:426:

```
CTACCTACGA TCTGACTAGC CACCGAAGGT TGGATGAGGG TAGGTCAAGG          50

TGCGGTATCC TAGCTTACTC TCATGTATTC C                              81
```

(2) INFORMATION FOR SEQ ID NO:427:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:427:

```
CTACCTACGA TCTGACTAGC GACCGACGTA GTCCAAAAGG CTCATAGTAC          50

CGTGTCAGTC TAGCTTACTC TCATGTATTC C                              81
```

(2) INFORMATION FOR SEQ ID NO:428:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:428:

```
GGGAGGACGA TGCGGACACG GCTAGTCGGA GGATTCACTT CCGCCCAGAC          50

GACGACGGGG A                                                    61
```

(2) INFORMATION FOR SEQ ID NO:429:

(i) SEQUENCE CHARACTERISTICS:

(A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:429:

GGGAGGACGA TGCGGCAGGC GACCTATATA GGTGGTATCC CCGTACAGAC        50

GACGACGGGG A        61

(2) INFORMATION FOR SEQ ID NO:430:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:430:

GGGAGGACGA TGCGGCACCG AGGAATAACT GACGCCAGGC TGGCGCAGAC        50

GACGACGGGG A        61

(2) INFORMATION FOR SEQ ID NO:431:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:431:

GGGAGGACGA TGCGGCCTCA GCGGATTTCT TGGCGAGTAG GAGCGCAGAC        50

GACGACGGGG A        61

(2) INFORMATION FOR SEQ ID NO:432:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (xi) SEQUENCE DESCRIPTION: SEQ ID NO:432:

ATCCGCCTGA TTAGCGATAC TAAGGCAAAC AACGTGACCG AGGCGTAGAG        50

GGTGGTCCTA GCACTTGAGC AAAATCACCT GCAGGGG        87

(2) INFORMATION FOR SEQ ID NO:433:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO:433:

ATCCGCCTGA TTAGCGATAC TACATGACGA TCCGGCCGAG TGGGTGGGTT        50

TCAAGGTCCG GACTTGAGCA AAATCACCTG CAGGGG        86

(2) INFORMATION FOR SEQ ID NO:434:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:434:

CTACCTACGA TCTGACTAGC AGCTAGTGCA CTTCGAGTAA CCGAGTGGTT      50

GGGAATCAAG TAGCTTACTC TCATGTATTC C      81

(2) INFORMATION FOR SEQ ID NO:435:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (xi) SEQUENCE DESCRIPTION: SEQ ID NO:435:

CTACCTACGA TCTGACTAGC CCTCTAGAGT CGACCTGCAG GCATGCAAGC      50

TTACCACTAT GCGTAGCTTA CTCTCATGTA TTCC      84

(2) INFORMATION FOR SEQ ID NO:436:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO:436:

GGGAGGACGA TGCGGGGGGC TATGCGATAC AGTCGCGNTA NGCTAGGCGC      50

AGACGAGCGG GA      62

(2) INFORMATION FOR SEQ ID NO:437:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:437:

GGGAGGACGA TGCGGGCCTN GATGCAGCGT CGGTAGGCNA ANCCCGAAAG      50

CCNCAGACGA CGACGGGGA      69

(2) INFORMATION FOR SEQ ID NO:438:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:438:

GGGAGGACGA TGCGGACCTG GTGGCTGTGC TTATGTCCCC CTCATCAGAC      50

GACGACGGGG A      61

(2) INFORMATION FOR SEQ ID NO:439:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:439:

GGGAGGACGA TGCGGGAGGC TGGGGTACAT CTCTNAGCAA GCATCAGACG      50

```
ACGACGGGGA                                                    60

(2) INFORMATION FOR SEQ ID NO:440:

(i) SEQUENCE CHARACTERISTICS:
         (A) LENGTH: 61 base pairs
         (B) TYPE: nucleic acid
         (C) STRANDEDNESS: single
         (D) TOPOLOGY: linear (xi) SEQUENCE DESCRIPTION: SEQ ID NO:440:

GGGAGGACGA TGCGGGCCCT GTGACTGTGC TTATGTCCTC CACATCAGAC         50

GACGACGGGG A                                                  61

(2) INFORMATION FOR SEQ ID NO:441:

(i) SEQUENCE CHARACTERISTICS:
         (A) LENGTH: 61 base pairs
         (B) TYPE: nucleic acid
         (C) STRANDEDNESS: single
         (D) TOPOLOGY: linear (xi) SEQUENCE DESCRIPTION: SEQ ID NO:441:

GGGAGGACGA TGCGGCTACT GTACTGCTTA TGTCTGTCCC CTCGTCAGAC         50

GACGACGGGG A                                                  61

(2) INFORMATION FOR SEQ ID NO:442:

(i) SEQUENCE CHARACTERISTICS:
         (A) LENGTH: 61 base pairs
         (B) TYPE: nucleic acid
         (C) STRANDEDNESS: single
         (D) TOPOLOGY: linear (xi) SEQUENCE DESCRIPTION: SEQ ID NO:442:

GGGAGGACGA TGCGGGGGGA GTCAATCACC GCACCCACTC CTCGTCAGAC         50

GACGACGGGG A                                                  61

(2) INFORMATION FOR SEQ ID NO:443:

(i) SEQUENCE CHARACTERISTICS:
         (A) LENGTH: 37 base pairs
         (B) TYPE: nucleic acid
         (C) STRANDEDNESS: single
         (D) TOPOLOGY: linear (xi) SEQUENCE DESCRIPTION: SEQ ID NO:443:

GGCGGGGCTA CGTACCGGGG CTTTGTAAAA CCCCGCC                       37

(2) INFORMATION FOR SEQ ID NO:444:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ix) FEATURE:
         (D) OTHER INFORMATION:  All C's are 2'-NH$_2$ cytosine (ix) FEATURE:
         (D) OTHER INFORMATION:  All U's are 2'-NH$_2$ uracil (ix) FEATURE:
         (A) NAME/KEY: C
         (B) LOCATION: 26
```

-continued

```
        (D) OTHER INFORMATION:  The C at location 26 is
            deoxycytidine (xi) SEQUENCE DESCRIPTION: SEQ ID NO:444:

GGUGUGUGGA AGACAGCGGG UGGUUDC                                             27

(2) INFORMATION FOR SEQ ID NO:445:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:445:

GGTGTGTGGA AGACAGCGGG TGGTTC                                              26
```

What is claimed is:

1. A purified and isolated non-naturally occurring DNA ligand to bFGF wherein the nucleic acid sequence of said ligand is selected from the group consisting of SEQ ID NOS: 330–444.

2. A purified and isolated non-naturally occurring nucleic acid ligand to bFGF wherein the nucleic acid sequence of said ligand is substantially homologous to and has substantially the same ability to bind bFGF as a ligand selected from the group consisting of SEQ ID NOS: 7–69, 101–185, 281–319 and 330–444.

3. A purified and isolated non-naturally occurring nucleic acid ligand to bFGF wherein said ligand has substantially the same structure and substantially the same ability to bind bFGF as a ligand selected from the group consisting of SEQ ID NOS: 7–69, 101–185, 281–319 and 330–444.

* * * * *